US012251385B2

(12) United States Patent
Butler et al.

(10) Patent No.: US 12,251,385 B2
(45) Date of Patent: Mar. 18, 2025

(54) COVALENT INHIBITORS OF MENIN-MLL INTERACTION FOR DIABETES MELLITUS

(71) Applicant: BIOMEA FUSION, INC., Redwood City, CA (US)

(72) Inventors: Thomas Butler, Redwood City, CA (US); James T. Palmer, Warrandyte (AU)

(73) Assignee: BIOMEA FUSION, INC., Redwood City, CA (US)

( * ) Notice: Subject to any disclaimer, the term of this patent is extended or adjusted under 35 U.S.C. 154(b) by 127 days.

(21) Appl. No.: 17/885,493

(22) Filed: Aug. 10, 2022

(65) Prior Publication Data
US 2023/0120115 A1 Apr. 20, 2023

Related U.S. Application Data

(60) Provisional application No. 63/317,518, filed on Mar. 7, 2022, provisional application No. 63/249,568, filed on Sep. 28, 2021, provisional application No. 63/232,154, filed on Aug. 11, 2021.

(51) Int. Cl.
*A61K 31/5377* (2006.01)
*A61P 3/10* (2006.01)

(52) U.S. Cl.
CPC ............ *A61K 31/5377* (2013.01); *A61P 3/10* (2018.01)

(58) Field of Classification Search
CPC ........................................................ A61P 3/10
See application file for complete search history.

(56) References Cited

U.S. PATENT DOCUMENTS

| | | | |
|---|---|---|---|
| 7,034,049 B1 | 4/2006 | Pevarello et al. | |
| 7,514,448 B2 | 4/2009 | Green et al. | |
| 11,084,825 B2 * | 8/2021 | Butler ................. | C07D 401/06 |
| 11,174,263 B2 | 11/2021 | Butler et al. | |
| 11,702,421 B2 | 7/2023 | Butler et al. | |
| 2002/0019526 A1 | 2/2002 | Blumenkopf et al. | |
| 2005/0209297 A1 | 9/2005 | Sanner et al. | |
| 2005/0282814 A1 | 12/2005 | Wrasidlo et al. | |
| 2006/0293336 A1 | 12/2006 | Green et al. | |
| 2009/0163545 A1 | 6/2009 | Goldfarb | |
| 2009/0215742 A1 | 8/2009 | Funk et al. | |
| 2010/0168084 A1 | 7/2010 | Huber et al. | |
| 2010/0256171 A1 | 10/2010 | Taunton et al. | |
| 2012/0263708 A1 | 10/2012 | Bader et al. | |
| 2013/0143926 A1 | 6/2013 | Donald et al. | |
| 2015/0376189 A1 | 12/2015 | Zorn et al. | |
| 2016/0185785 A1 | 6/2016 | Loannidis et al. | |
| 2017/0119769 A1 | 5/2017 | Hua et al. | |
| 2018/0244654 A1 | 8/2018 | Schlitz et al. | |
| 2020/0216471 A1 | 7/2020 | Wu et al. | |
| 2020/0223853 A1 | 7/2020 | Butler et al. | |
| 2020/0255434 A1 | 8/2020 | Butler et al. | |
| 2022/0024936 A1 | 1/2022 | Butler et al. | |
| 2022/0169627 A1 | 6/2022 | Butler et al. | |
| 2023/0086137 A1 | 3/2023 | Somanath et al. | |
| 2023/0120115 A1 | 4/2023 | Butler et al. | |
| 2023/0150991 A1 | 5/2023 | Sands et al. | |
| 2023/0391784 A1 | 12/2023 | Butler et al. | |

FOREIGN PATENT DOCUMENTS

| | | |
|---|---|---|
| CN | 102266341 A | 12/2011 |
| CN | 105997965 A | 10/2016 |
| CN | 107176951 A | 9/2017 |
| CN | 108727295 A | 11/2018 |
| DE | 10219294 A1 | 11/2003 |
| DE | 102004048877 A1 | 4/2006 |
| EP | 2 924 039 A1 | 9/2015 |
| FR | 2878849 A1 | 6/2006 |
| JP | H09157392 A | 6/1997 |
| JP | 2014/166961 A | 9/2014 |
| JP | 2015/183128 A | 10/2015 |
| KR | 2014/125117 A | 10/2014 |
| RU | 2364597 C1 | 8/2009 |
| WO | WO 2001/012189 A1 | 2/2001 |
| WO | WO 2002/018346 A1 | 3/2002 |
| WO | WO 2002/048114 A1 | 6/2002 |
| WO | WO 2002/083648 A1 | 10/2002 |
| WO | WO 2003/000688 A1 | 1/2003 |
| WO | WO 2003/035065 A1 | 5/2003 |
| WO | WO 2003/035644 A1 | 5/2003 |
| WO | WO 2004/089415 A2 | 10/2004 |
| WO | WO 2004/089416 A2 | 10/2004 |
| WO | WO 2004/089470 A2 | 10/2004 |
| WO | WO 2005/002552 A2 | 1/2005 |
| WO | WO 2005/030206 A1 | 4/2005 |
| WO | WO 2005/041879 A2 | 5/2005 |
| WO | WO 2005/042495 A1 | 5/2005 |
| WO | WO 2005/095400 A1 | 10/2005 |
| WO | WO 2005/103050 A2 | 11/2005 |
| WO | WO 2005/121147 A1 | 12/2005 |
| WO | WO 2006/040279 A1 | 4/2006 |
| WO | WO 2006/058210 A1 | 6/2006 |

(Continued)

OTHER PUBLICATIONS

Menin and PRMT5 suppress GLP1 receptor transcript and PKA-mediatedphosphorylation of FOXO1 and CREB Muhammad et al. Am J Physiol Endocrinol Metab313: E148-E166, 2017 (Year: 2017).*

(Continued)

*Primary Examiner* — Jeffrey S Lundgren
*Assistant Examiner* — Eric Tran
(74) *Attorney, Agent, or Firm* — Squire Patton Boggs (US) LLP

(57) ABSTRACT

Disclosed herein are heterocyclic compounds that inhibit the binding of menin and MLL or MLL fusion proteins for the treatment of diabetes mellitus. Also described are specific covalent inhibitors of menin-MLL interaction. Also disclosed are pharmaceutical compositions that include the described compounds. Methods of using the menin-MLL covalent inhibitors are disclosed, alone or in combination with other therapeutic agents, for the treatment of diabetes mellitus.

17 Claims, 26 Drawing Sheets

(56) References Cited

FOREIGN PATENT DOCUMENTS

| | | | |
|---|---|---|---|
| WO | WO 2006/061493 A1 | 6/2006 | |
| WO | WO 2006/091671 A1 | 8/2006 | |
| WO | WO 2006/108640 A1 | 10/2006 | |
| WO | WO 2006/123061 A2 | 11/2006 | |
| WO | WO 2007/019416 A1 | 1/2007 | |
| WO | WO 2007/017083 A1 | 2/2007 | |
| WO | WO 2007/019344 A1 | 2/2007 | |
| WO | WO 2007/019345 A1 | 2/2007 | |
| WO | WO 2007/019346 A1 | 2/2007 | |
| WO | WO 2007/019417 A1 | 2/2007 | |
| WO | WO 2007/064902 A2 | 6/2007 | |
| WO | WO 2007/064931 A2 | 6/2007 | |
| WO | WO 2007/091106 A2 | 8/2007 | |
| WO | WO 2007/117465 A2 | 10/2007 | |
| WO | WO 2008/075196 A1 | 6/2008 | |
| WO | WO 2009/019504 A1 | 2/2009 | |
| WO | WO 2009/077956 A2 | 6/2009 | |
| WO | WO 2010/011762 A1 | 1/2010 | |
| WO | WO 2010/129620 A1 | 11/2010 | |
| WO | WO 2012/135799 A1 | 10/2012 | |
| WO | WO 2012/176763 A1 | 12/2012 | |
| WO | WO 2004/030635 A2 | 4/2014 | |
| WO | WO 2014/118135 A1 | 8/2014 | |
| WO | WO 2015/000959 A1 | 1/2015 | |
| WO | WO 2015/040425 A1 | 3/2015 | |
| WO | WO 2015/144926 A1 | 10/2015 | |
| WO | WO 2015/0195228 A1 | 12/2015 | |
| WO | WO 2015/195228 A1 | 12/2015 | |
| WO | WO 2016/051193 A1 | 4/2016 | |
| WO | WO 2016/148114 A1 | 9/2016 | |
| WO | WO 2016/197078 A1 | 12/2016 | |
| WO | WO 2016/202758 A1 | 12/2016 | |
| WO | WO 2017/075367 A1 | 5/2017 | |
| WO | WO 2017/152874 A1 | 9/2017 | |
| WO | WO 2017/161002 A1 | 9/2017 | |
| WO | WO 2017/161028 A1 | 9/2017 | |
| WO | WO 2017/161280 A1 | 9/2017 | |
| WO | WO 2017/0192543 A1 | 11/2017 | |
| WO | WO 2017/214367 A1 | 12/2017 | |
| WO | WO 2018/106818 A1 | 6/2018 | |
| WO | WO 2018/106820 A1 | 6/2018 | |
| WO | WO 2018/132372 A1 | 7/2018 | |
| WO | WO 2018/175537 A1 | 9/2018 | |
| WO | WO 2018/183857 A1 | 10/2018 | |
| WO | WO 2019/192962 A1 | 10/2019 | |
| WO | WO 2020/142559 A1 | 7/2020 | |
| WO | WO-2020142557 A1 * | 7/2020 | ......... A61K 31/5377 |
| WO | WO-2022086986 A1 * | 4/2022 | ......... A61K 31/4365 |
| WO | WO 2022/133064 A1 | 6/2022 | |
| WO | WO 2023/018825 A1 | 2/2023 | |
| WO | WO 2023/022912 A1 | 2/2023 | |
| WO | WO 2023/129667 A1 | 7/2023 | |
| WO | WO 2023/150635 A1 | 8/2023 | |
| WO | WO 2023/235618 A1 | 12/2023 | |
| WO | WO 2024/006391 A1 | 1/2024 | |

OTHER PUBLICATIONS

International Search Report and Written Opinion for International Application PCT/US2019/069155, 10 pages, mailed Apr. 24, 2020.
International Search Report and Written Opinion for International Application PCT/US2019/069157, 10 pages, mailed Apr. 21, 2020.
S. Xu et al., "Design of the First-in-Class, Highly Potent Irreversible Inhibitor Targeting the Menin-MLL Protein-Protein Interaction", Angewandte Chemie International Ed. 57(6), 1601-1605 (2017).
Borisa et al., "3D-QSAR (CoMFA, CoMFA-RG, CoMSIA) and molecular docking study of thienopyrimidine and thienopyridine derivatives to explore structural requirements for aurora-B kinase inhibition", European Journal of Pharmaceutical Sciences (2015), 13 pages, 79, 1-12.
Dorwald, F. Zaragoza, Side Reactions in organic Syntehsis: A guide to Successful Synthesis Design, Weinheim: Wiley-VCH Verlag GmbH & Co. KGaA 2005 Preface.
European Search Report for EP Application No. 19906970.9, 56 pages, dated Sep. 15, 2022.
Hackam, et al. JAMA 296(14): 1731-1732 (2006).
Jordan, V.C. Nature Reviews: Drug Discovery 2: 2003:205.
Pevarello et al., 3-Aminopyrazole Inhibitors of CDK2/Cyclin A as Antitumor Agents. 2. Lead Optimization:, Journal Med. Chem. 2005, 13 pages, 48:2944-2956.
Pevarello et al., 3-Aminopyrazole Inhibitors of CDK2/Cyclin A as Antitumor Agents. 2. Lead Optimization:, Additions and Corrections, Journal Med. Chem. 2005, 13 pages, 45:5058.
Stella, Valentino "Prodrugs: Some Thoughts and Current Issues", Journal of Pharmaceutical Sciences, 2010, 99(12) pp. 4755-4765.
Butler Thomas et al: "Oral Long-Acting Menin Inhibitor, BMF-219, Normalizes Type 2Diabetes Mellitus in Two Rat Models", ADA 2022, Jun. 1, 2022 (Jun. 1, 2022), XP093001069, Retrieved from the Internet: URL:https:// biomeafusion.com/wp-content/uploads/2022/06/ADA-Poster-2022_Regular-Abstract_052622_Final2.pdf.
International Search Report and Written Opinion for International Application No. PCT/US2022/039990, 13 pages, dated Dec. 2, 2022.
International Search Report and Written Opinion for International Application No. PCT/US2022/039941, 20 pages, dated Jan. 23, 2023.
Jian et al: "Menin-regulated Pbk controls high fat diet-induced compensatory beta cell proliferation", EMBO Molecular Medicine, vol. 13, No. 5, Apr. 6, 2021 (Apr. 6, 2021), XP093001179, US ISSN: 1757-4676, DOI: 10.15252/emmm.202013524 Retrieved from the Internet: URL:https://onlinelibrary.wiley.com/doi/full-XML/10.15252/emmm.202013524.
Somanath Priyanka et al: "Oral Menin Inhibitor, BMF-219, displays a significant and durable reduction in HbA1c in a Type 2 Diabetes Mellitus Rat Model", Jun. 1, 2022 (Jun. 1, 2022), XP093001072, Retrieved from the Internet: URL:https://biomeafusion.com/wp-content/uploads/2022/06/ADA-Poster-2022_Late-Breaking_052622_Final.pdf.
Yang et al. "Reversal of preexisting hyperglycemia in diabetic mice by acute deletion of the Men1 gene", Proceedings of the National Academy of Sciences, vol. 107, No. 47, Nov. 8, 2010 (Nov. 8, 2010), pp. 20358-20363, XP093000810, ISSN: 0027-8424, DOI: 10.1073/pnas. 1012257107 Retrieved from the Internet: URL:https://www.ncbi.nlm.nih.gov/pmc/articles/PMC2996686/pdf/pnas.201012257.
International Search Report and Written Opinion for International Application No. PCT/US2021/063761, 16 pages, dated Mar. 16, 2022.
CAS SciFinder; Returned Reference Search Report for References of US20200223853; 15 pages, Jun. 30, 2021.
Ma, J. et al. "Menin-regulated Pbk controls high fat diet-induced compensatory beta cell proliferation," EMBO Molecular Medicine, vol. 13, No. 5, Apr. 6, 2021 (Apr. 6, 2021), XP093001179, US ISSN: 1757-4676, DOI: 10.15252/emmm.202013524 Retrieved from the Internet: URL:https://onlinelibrary.wiley.com/doi/full-XML/10.15252/emmm.202013524.
Pahlavanneshan et al. "Combined Inhibition of Menin-MII Interaction and TGF-[Beta] Signaling Induces Replication of Human Pancreatic Beta Cells", European Journal of Cell Biology, vol. 99(5) May 30, 2020 DOI:10.1016/J.EJCB.2020.151094.
Winters and Bernt, "MLL-Reaarranged Leukemias An Update on Science and Clinical Approaches", 21 pages, Front. Pediatr. 5, 4 (2017).

* cited by examiner

* p<0.05 vs Vehicle

FIG. 13B  FIG. 13C  FIG. 13D
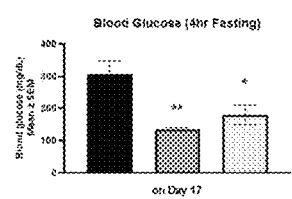
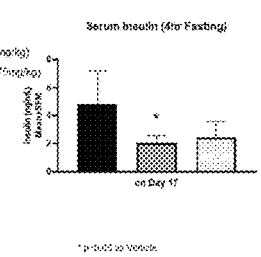
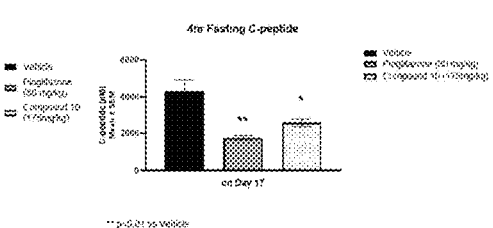
FIG. 13E
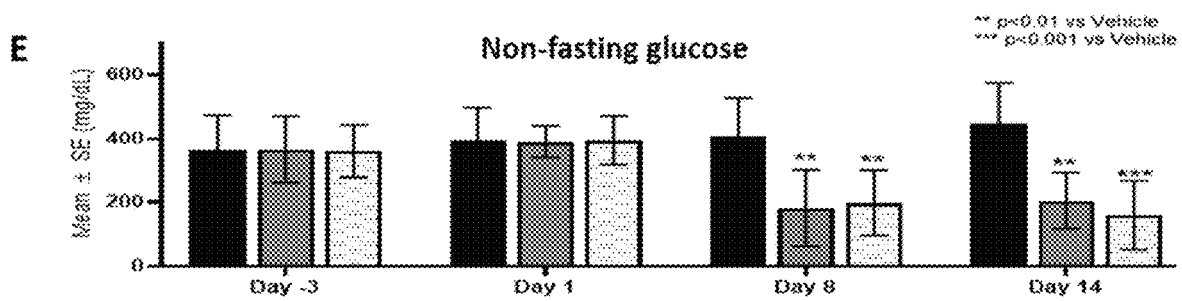

*p<0.05 vs Vehicle

COVALENT INHIBITORS OF MENIN-MLL INTERACTION FOR DIABETES MELLITUS

CROSS REFERENCE

The present application claims the benefit of U.S. provisional application Nos. 63/232,154, filed Aug. 11, 2021, 63/249,568, filed Sep. 28, 2021, and 63/317,518, filed Mar. 7, 2022, the contents of each of which are hereby incorporated by reference in their entireties.

FIELD

Described herein are compounds, methods of making such compounds, pharmaceutical compositions and medicaments containing such compounds, and methods of using such compounds and compositions that inhibit the activity of menin-MLL for the treatment of diabetes mellitus.

BACKGROUND

The Histone-lysine N-methyltransferase 2 (KMT2) family of proteins, which currently consists of at least five members, methylate lysine 4 on the histone H3 tails at important regulatory regions in the genome and thereby impart crucial functions through the modulation of chromatin structures and DNA accessibility (Morera, Lübbert, and Jung., Clin. Epigenetics 8, 57-(2016)). These enzymes are known to play an important role in the regulation of gene expression during early development and hematopoiesis (Rao & Dou., Nat. Rev. Cancer 15, 334-346 (2015)).

The human KMT2 family was initially named the mixed-lineage leukaemia (MLL) family, owing to the role of the first-found member in this disease, KMT2A, which is still commonly referred to as MLL1 or MLL in routine clinical practice.

KMT2A (MLL1) is frequently found to be cytogenetically targeted in several types of leukemia (e.g., ALL and AML), and in those cases where balanced chromosomal translocations are found, these typically target KMT2A (MLL1) and one of over eighty translocation partner genes that have been described to date (Winters and Bernt, Front. Pediatr. 5, 4 (2017)). These chromosomal anomalies often result in the formation of fusion genes that encode fusion proteins which are believed to be causally related to the onset and/or progression of the disease. Inhibition of menin may be a promising strategy for treating MLL related diseases including diabetes.

M-525 is a highly potent, covalent small molecule inhibitor of the menin-MLL protein-protein interaction. It forms a covalent bond with the Cys329 residue in menin. M-525 demonstrates high cellular specificity over non-MLL leukemia cells and is >30 times more potent than the corresponding reversible inhibitors. See S. Xu et al. Angewandte Chemie International Ed. 57(6), 1601-1605 (2017).

Diabetes mellitus, commonly referred to as diabetes, is a major worldwide medical problem. As of 2019, an estimated 463 million people had diabetes worldwide, with type 2 diabetes mellitus making up about 90% of the cases. IDF Diabetes Atlas Ninth Edition, 2019. Rates are similar in both women and men. Current and proposed treatments include insulin (type 1 diabetes), and metformin, glucagon-like peptide1 receptor agonists (GLP-1Ra), sulfonylureas, dipeptidyl peptidase-4 inhibitors (DDP-4I), thiazolidinedione, sodium-glucose cotransporter 2 (SGLT2 inhibitors), and insulin (type 2 diabetes). Even with these treatments, disease rates are rising, and the global economic cost of diabetes mellitus was estimated at $727 billion USD in 2017. Despite the above treatment options available for T2DM, approximately 50% of patients have glycated hemoglobin (HbA1c) values above the recommended 7% target (CDC 2020), and therefore, the condition remains an unmet medical need.

New medicines are needed for the treatment of diabetes mellitus.

SUMMARY

Described herein are covalent inhibitors of menin-MLL interaction for the treatment of diabetes mellitus. Also described herein are specific heterocyclic covalent inhibitors of menin-MLL or MLL fusion protein interactions for the treatment of diabetes mellitus.

Additionally, methods described herein include methods for synthesizing covalent inhibitors of menin-MLL or MLL fusion protein interactions, and methods for using such covalent inhibitors in the treatment of diseases (including diseases wherein inhibition of menin-MLL interaction provides therapeutic benefit to a patient having the disease). Further described herein are pharmaceutical compositions that include an inhibitor of menin-MLL interaction. Specifically, described herein are compounds and their methods of use to inhibit the interaction of menin with MLL oncoproteins (e.g., MLL1, MLL2, and/or MLL-fusion oncoproteins).

Specifically described herein are covalent inhibitors of menin-MLL interaction that form a covalent bond with a cysteine residue on menin. Further described herein are covalent inhibitors of menin-MLL interaction that form a covalent bond with a Cys329 residue on menin. Also described herein are pharmaceutical formulations that include a covalent inhibitor of menin.

In some embodiments, provided are methods for preventing, treating, or ameliorating in a mammal a diabetic disease or condition that is causally related to the aberrant activity of a menin-MLL interaction in vivo, which comprises administering to the mammal an effective disease-treating or condition-treating amount of a compound according to Formula (I) having the structure

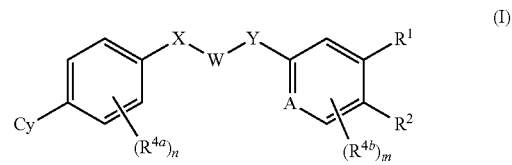

or a pharmaceutically acceptable salt thereof,
wherein:
A is carbon or nitrogen;
Cy is substituted or unsubstituted

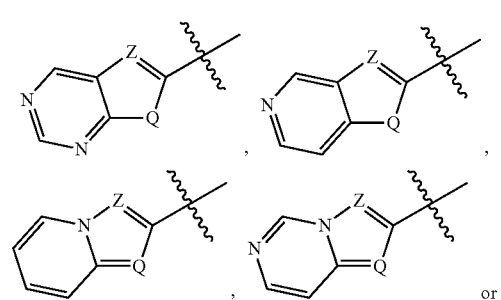

-continued

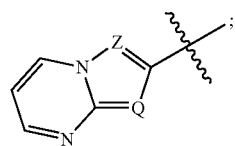

Q is nitrogen, —N(H)—, —O—, or —S—;

Z is —CR$^{5a}$═ or —N═;

X is —NR$^{3a}$—, —C(R$^{3b}$)$_2$—, or —O—;

Y is a single bond, —NR$^{3a}$—, —C(R$^{3b}$)$_2$—, or —O—;

W is —C(O)—, —S(O)—, or —S(O)$_2$—;

one of R$^1$ and R$^2$ is Cy$^2$-N(H)C(O)—C(R$^{6a}$)═C(R$^{6b}$)(R$^{6c}$) or CH$_2$-Cy$^2$-N(H)C(O)—C(R$^{6a}$)═C(R$^{6b}$)(R$^{6c}$); and other is hydrogen, C$_{1-6}$ alkyl, C$_{1-6}$ haloalkyl, halo, or CN;

Cy$^2$ is an optionally substituted group selected from phenyl, pyridyl, or a 4- to 7-membered heterocycloalkyl ring having one to two heteroatoms independently selected from nitrogen, oxygen, or sulfur;

each R$^{3a}$ and R$^{3b}$ is independently hydrogen or C$_{1-6}$ alkyl;

each R$^{4a}$ and R$^{4b}$ is independently hydrogen, halo, CN, OR, —N(R)$_2$, —C(O)N(R)$_2$, —NRC(O)R, —SO$_2$R, —C(O)R, —CO$_2$R, or an optionally substituted group selected from C$_{1-6}$ alkyl, C$_{3-7}$ cycloalkyl, a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur;

each R is independently hydrogen, or an optionally substituted group selected from C$_{1-6}$ aliphatic, phenyl, an 8- to 10-membered bicyclic aryl ring, a 4- to 7-membered saturated or partially unsaturated heterocyclic ring having one to two heteroatoms independently selected from nitrogen, oxygen, or sulfur, and a 5- to 6-membered heteroaryl ring having one to four heteroatoms independently selected from nitrogen, oxygen, or sulfur; or two R groups on the same nitrogen are taken together with their intervening atoms to form a 4- to 7-membered saturated, partially unsaturated, or heteroaryl ring having zero to three heteroatoms, in addition to the nitrogen, independently selected from nitrogen, oxygen, or sulfur;

R$^{5a}$ is hydrogen, C$_{1-6}$ alkyl, C$_{1-6}$ haloalkyl, halo, or CN;

each R$^{5a}$ and R$^{6b}$ is independently hydrogen or C$_{1-6}$ alkyl; or

R$^{6a}$ and R$^{6b}$ are joined together to form a bond;

R$^{6c}$ is hydrogen or substituted or unsubstituted C$_{1-6}$ alkyl;

m is one, two, or three; and n is one, two, three, or four.

In some embodiments, provided is a compound according to Formula (XXI)

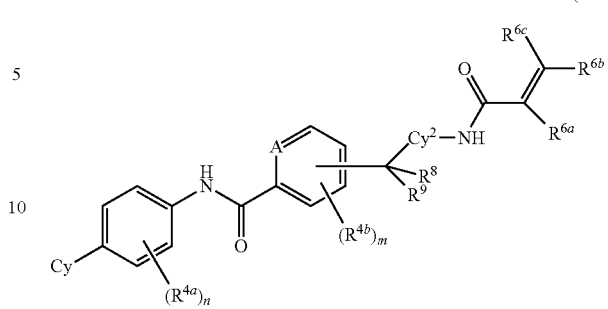

or a pharmaceutically acceptable salt thereof, wherein
A, Cy, Cy$^2$, R$^{4b}$, R$^{6a}$, R$^{6b}$, R$^{6c}$, m, and n are as described for Formula (I); and
each R$^8$ and R$^9$ is independently hydrogen, C$_{1-6}$ alkyl, C$_{1-6}$ haloalkyl, halo, or CN.

In some embodiments, X is —N(H)— and Y is —NH—, —C(H)$_2$— or oxygen. In some embodiments, each of X and Y is —N(H)—.

In some embodiments, W is —S(O)— or —S(O)$_2$—. In a particular embodiment, W is —C(O)—.

In some embodiments, —X—W—Y— is —N(H)—C(O)—N(H)—, —N(H)—C(O)—CH$_2$—, —CH$_2$—C(O)—N(H)—, —N(H)—S(O)—N(H)—, —N(H)—S(O)—CH$_2$—, —CH$_2$—S(O)—N(H)—, —N(H)—S(O)$_2$—N(H)—, —N(H)—S(O)$_2$—CH$_2$—, —CH$_2$—S(O)$_2$—N(H)—, or —N(H)—C(O)—.

In some embodiments, the compound is according to Formula (IIa), (IIb), (IIc), or (IId)

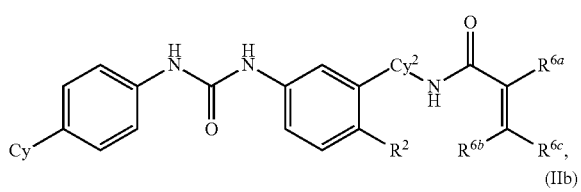

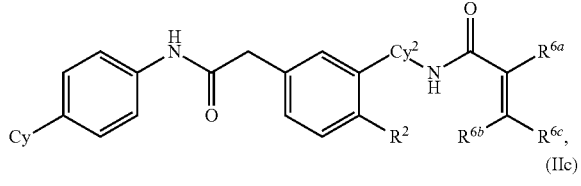

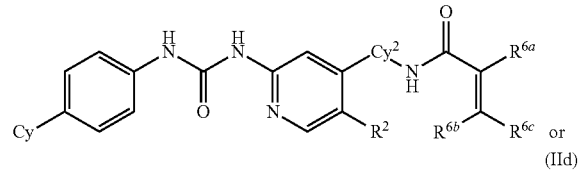

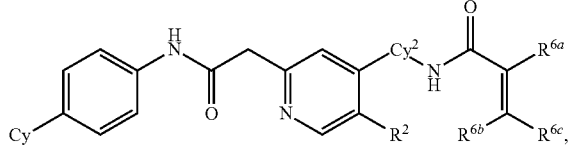

or a pharmaceutically acceptable salt thereof.

In some embodiments, $R^2$ is hydrogen, Me, Et, i-Pr, $CF_3$, F, Cl, OMe, OEt, or CN.

In some embodiments, the compound is according to Formula (XV)

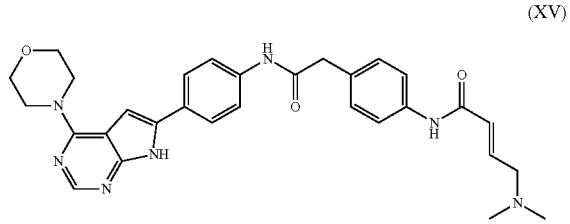 [SMILES: CN(C)C/C=C/C(=O)Nc1ccc(CC(=O)Nc2ccc(-c3cc4c(N5CCOCC5)ncnc4[nH]3)cc2)cc1]

(XV)

or a pharmaceutically acceptable salt thereof.

In some embodiments, the compound is according to Formula (XVI)

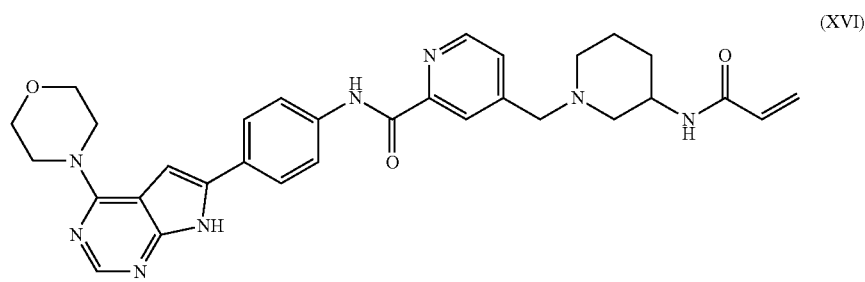 [SMILES: C=CC(=O)NC1CCCN(Cc2ccnc(C(=O)Nc3ccc(-c4cc5c(N6CCOCC6)ncnc5[nH]4)cc3)c2)C1]

(XVI)

or a pharmaceutically acceptable salt thereof. In some embodiments, the compound is according to Formula (XVII)

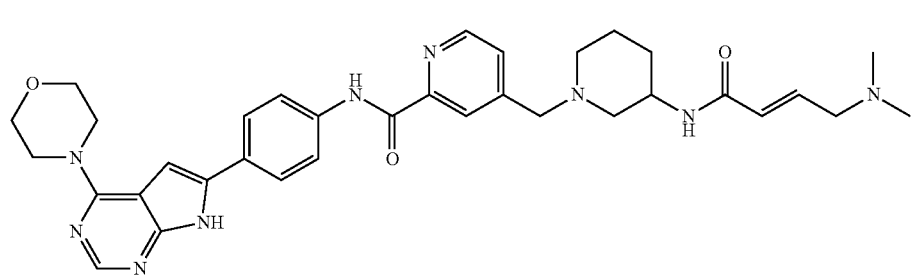

(XVII)

or a pharmaceutically acceptable salt thereof.

In some embodiments, the active site is a cavity in which the compounds or moieties described herein bind to the MLL site on the menin. In some embodiments, the active site is menin at the MLL binding site.

In some embodiments, using a compound as disclosed herein, the disease or condition to be treated is diabetes mellitus. In some embodiments, the disease or condition is type 1 diabetes mellitus. In some embodiments, the disease or condition is type 2 diabetes mellitus. In some embodiments, the disease or condition is gestational diabetes mellitus. In some embodiments, the disease or condition is maturity onset diabetes of the young. In some embodiments, the disease or condition is steroid induced diabetes. In some embodiments, the disease or condition is double diabetes.

In some embodiments, provided are pharmaceutical compositions comprising a therapeutically effective amount of a compound of Formula (I) and a pharmaceutically acceptable excipient. In some embodiments, the pharmaceutical composition comprising the compound of Formula (I) is formulated for a route of administration selected from oral administration, parenteral administration, buccal administration, nasal administration, topical administration, or rectal administration. In some embodiments, provided are methods for treating a diabetic disease or condition as disclosed herein, the methods comprising administering to a patient in need a therapeutically effective amount of a compound of Formula (I). In some embodiments, provided is a method for treating diabetes mellitus comprising administering to a patient in need a therapeutically effective amount of a compound of Formula (I). In some embodiments, the diabetes is type 1 diabetes. In some embodiments, the diabetes is type 2 diabetes. In some embodiments, the diabetes is gestational diabetes.

Any combination of the groups or embodiments described above (i.e., including the several variables) is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In some embodiments, provided are pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof that deliver amounts effective for the treatment, prevention, or amelioration of one or more symptoms of diseases, disorders, or conditions that are modulated or otherwise affected by Menin-MLL activity, or in which Menin-MLL activity is implicated, are provided. The effective amounts and concentrations are effective for ameliorating any of the symptoms of any of the diseases, disorders, or conditions disclosed herein.

In certain embodiments, provided herein is a pharmaceutical composition containing i) a physiologically acceptable carrier, diluent, and/or excipient; and ii) one or more compounds provided herein.

In some embodiments, provided herein are methods for treating a patient by administering a compound provided herein. In some embodiments, provided herein is a method of inhibiting the activity of Menin-MLL, or a method of treating a disease, disorder, or condition, which would benefit from inhibition of Menin-MLL activity, in a patient, which includes administering to the patient a therapeutically effective amount of at least one of any of the compounds herein, or a pharmaceutically acceptable salt, pharmaceutically active metabolite, pharmaceutically acceptable prodrug, or pharmaceutically acceptable solvate thereof.

In some embodiments, provided herein is the use of a compound as disclosed herein for inhibiting Menin-MLL activity or for the treatment of a disease, disorder, or condition, which would benefit from inhibition of Menin-MLL activity.

In some embodiments, compounds provided herein are administered to a human.

In some embodiments, compounds provided herein are orally administered.

In some embodiments, compounds provided herein are used for the formulation of a medicament for the inhibition of Menin-MLL activity. In some embodiments, compounds provided herein are used for the formulation of a medicament for the inhibition of Menin-MLL activity.

Articles of manufacture including packaging material, a compound or composition or pharmaceutically acceptable derivative thereof provided herein which is effective for inhibiting the activity of Menin-MLL, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of Menin-MLL, are provided.

In any of the aforementioned embodiments are some embodiments in which administration is enteral, parenteral, or both, and wherein (a) an effective amount of a provided compound is systemically administered to the mammal; (b) an effective amount of a provided compound is administered orally to the mammal; (c) an effective amount of a provided compound is intravenously administered to the mammal; (d) an effective amount of a provided compound is administered by inhalation; (e) an effective amount of a provided compound is administered by nasal administration; (f) an effective amount of a provided compound is administered by injection to the mammal; (g) an effective amount of a provided compound is administered topically (dermal) to the mammal; (h) an effective amount of a provided compound is administered by ophthalmic administration; or (i) an effective amount of a provided compound is administered rectally to the mammal.

In any of the aforementioned embodiments are some embodiments comprising single administrations of an effective amount of a provided compound, including some embodiments in which (i) a provided compound is administered once; (ii) a provided compound is administered to the mammal multiple times over the span of one day; (iii) continually; or (iv) continuously.

In any of the aforementioned embodiments are some embodiments comprising multiple administrations of an effective amount of a provided compound, including some embodiments in which (i) a provided compound is administered in a single dose; (ii) the time between multiple administrations is every six hours; or (iii) a provided compound is administered to the mammal every eight hours. In some embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from two days to one year.

In any of the aforementioned embodiments involving the treatment of diabetes, are some embodiments comprising administering at least one additional agent selected from the group consisting of insulin and metformin, GLP-1Ra, sulfonylureas, dipeptidyl peptidase-4 inhibitors, thiazolidinedione, and SGLT2 inhibitors.

The term "covalent menin inhibitor," as used herein, refers to an inhibitor of menin that can form a covalent bond with an amino acid residue of menin. In certain embodiments, the inhibitor is irreversible.

In some embodiments, the compounds of Formula (I)-(XLIIIc) are covalent inhibitors of Menin-MLL activity. In certain embodiments, such covalent inhibitors have an $IC_{50}$ below 10 µM in an enzyme assay. In some embodiments, a menin-MLL inhibitor has an $IC_{50}$ of less than one µM, and in some embodiments, less than 0.25 µM.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to patents, patent application publications, articles, books, manuals, and treatises are hereby expressly incorporated by reference in their entirety for any purpose.

BRIEF DESCRIPTION OF THE FIGURES

FIG. 4A provides blood glucose, and FIG. 4B provides blood glucose area under the curve data.

FIG. 5A provides blood glucose, and FIG. 5B provides blood glucose area under the curve data.

FIG. 11A provides blood glucose, and FIG. 11B provides blood glucose area under the curve data.

FIGS. 13A-13E show Compound 10 significantly reduces blood glucose levels and alters serum insulin and C-peptide levels in ZDF rats. ZDF rats treated with Compound 10, pioglitazone, or vehicle for sixteen days were evaluated at various time points. Day 15 OGTT results are shown as time course and AUC (FIG. 13A). Day 17 fasting blood glucose levels (FIG. 13B), fasting insulin (FIG. 13C), and fasting C-peptide (FIG. 13D) are shown. Non-fasting blood sugar was measured weekly on Days −3, 1, 8 and 14 (FIG. 13E). Statistical significance was calculated for treatment groups in comparison with vehicle control.

DETAILED DESCRIPTION

Certain Terminology

Figure 1A:
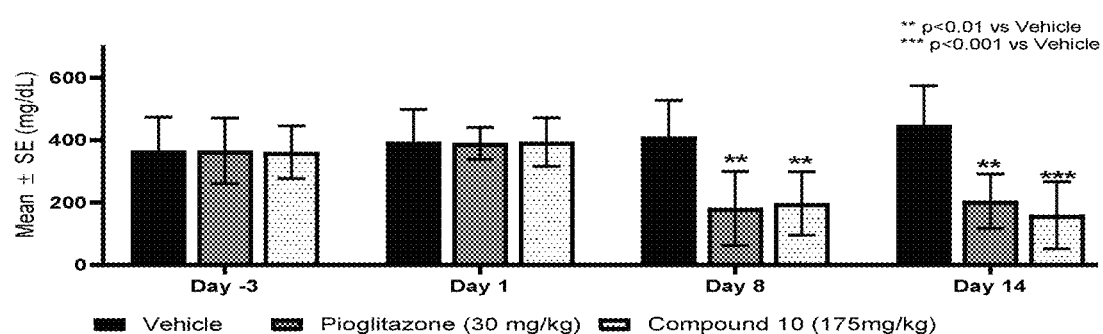
FIGS. 1A and 1B provide glucose in the non-fasting (FIG. 1A) and fasting (FIG. 1B) states following administration of Compound 10, vehicle, or control in Zucker Diabetic Fatty (ZDF) rats.

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in this specification and the appended claims, the singular forms "a," "an," and "the" include plural referents unless the context clearly dictates otherwise. Use of the term "including" as well as other forms, such as "include," "includes," and "included," is not limiting. Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology within the person of skill in the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed, for example, using kits including the manufacturer's specifications or as commonly accomplished in the art or as described herein. The foregoing techniques and procedures can be generally performed via conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein or the appended claims.

All publications and patents mentioned herein are incorporated herein by reference in their entirety for the purpose of describing and disclosing, for example, the constructs and methodologies that are described in the publications which might be used in connection with the methods, compositions, and compounds described herein. The publications discussed herein are provided solely for their disclosure prior to the filing date of the present application. Nothing herein is to be construed as an admission that the inventors are not entitled to antedate such disclosure by virtue of prior disclosure or for any other reason.

"Alkyl" as used herein refers to a straight or branched hydrocarbon chain radical consisting solely of carbon and hydrogen atoms, containing no unsaturation, and having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In some embodiments, an alkyl comprises five to fifteen carbon atoms (e.g., $C_5$-$C_{15}$ alkyl). In certain embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl (n-pr), 1-methylethyl (iso-propyl or i-Pr), n-butyl (n-Bu), n-pentyl, 1,1-dimethylethyl (t-butyl, or t-Bu), 3-methylhexyl, 2-methylhexyl, and the like. Unless stated otherwise specifically in the specification, an alkyl group is optionally substituted as defined and described elsewhere herein.

In certain embodiments, the alkyl group could also be a "lower alkyl" having one to six carbon atoms (e.g., $C_1$-$C_6$ alkyl).

As used herein, "$C_1$-$C_x$" includes $C_1$-$C_2$, $C_1$-$C_3$ ... $C_1$-$C_x$ where x is an integer from one to fifty.

"Alkenyl" as used herein refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In some embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in this specification, an alkenyl group is optionally substituted as defined and described elsewhere herein.

"Alkynyl" as used herein refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In some embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in this specification, an alkynyl group is optionally substituted as defined and described elsewhere herein.

"Alkylene" or "alkylene chain" as used herein refers to a straight or branched divalent hydrocarbon chain linking the rest of the molecule to a radical group, consisting solely of carbon and hydrogen, containing no unsaturation and having from one to twelve carbon atoms, for example, methylene (—CH$_2$—), —CH$_2$CH$_2$—, —CH$_2$CH$_2$CH$_2$—, —CH$_2$CH$_2$CH$_2$CH$_2$—, and the like. The alkylene chain is attached to the rest of the molecule through a single bond via each radical group. The points of attachment of the alkylene chain to the rest of the molecule and to the radical group can be through one carbon in the alkylene chain or through any two carbons within the chain. Unless stated otherwise specifically in this specification, an alkylene chain is optionally substituted as defined and described elsewhere herein.

"Alkenylene" or "alkenylene chain" as used herein refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond via each radical group. The points of attachment of the alkenylene chain to the rest of the molecule and to the radical group can be through one carbon or any two carbons within the chain. Unless stated otherwise specifically in this specification, an alkenylene chain is optionally substituted as defined and described elsewhere herein.

"Aryl" as used herein refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon (i.e., six to eighteen carbon atoms), where at least one of the rings in the ring system is fully unsaturated (i.e., contains a cyclic, delocalized (4n+2) π-electron system in accordance with the Hückel theory). Aryl groups include, but are not limited to, groups such as phenyl (Ph), fluorenyl, and naphthyl. Unless stated otherwise specifically in this specification, the term "aryl" or the prefix "ar-" (such as in "aralkyl") is meant to include aryl radicals optionally substituted as defined and described elsewhere herein.

"Aralkyl" as used herein refers to a radical of the formula —$R^c$-aryl where $R^c$ is an alkylene chain as defined above; for example, benzyl, diphenylmethyl, and the like. The alkylene chain part of the aralkyl radical is optionally substituted as described above for an alkylene chain. The aryl part of the aralkyl radical is optionally substituted as described above for an aryl group.

"Aralkenyl" as used herein refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" as used herein refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" as used herein refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In some embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include cyclopropyl

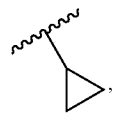

cyclobutyl

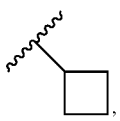

cyclopentyl

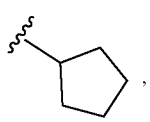

cyclohexyl

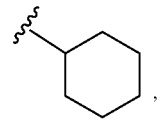

cycloheptyl

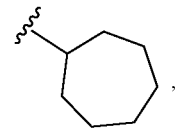

and cyclooctyl

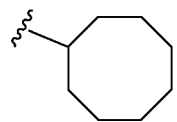

An unsaturated carbocyclyl is also referred to as "cycloalkenyl." Examples of monocyclic cycloalkenyls include cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in this specification, the term "carbocyclyl" is meant to include carbocyclyl radicals that are optionally substituted as defined and described elsewhere herein.

"Halo" or "halogen" as used herein refers to bromo (Br), chloro (Cl), fluoro (F), or iodo (I) substituents.

The terms "haloalkyl," "haloalkenyl," "haloalkynyl," and "haloalkoxy" include alkyl, alkenyl, alkynyl, and alkoxy (infra) structures in which at least one hydrogen is replaced with a halogen atom. In certain embodiments in which two or more hydrogen atoms are replaced with halogen atoms, the halogen atoms are all the same. In some embodiments in which two or more hydrogen atoms are replaced with halogen atoms, the halogen atoms are not all the same.

"Fluoroalkyl" as used herein refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl," or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen, and sulfur. The radicals may be fused with an aryl or heteroaryl. Heterocycloalkyl rings can be formed by three to fourteen ring atoms, such as three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo (C=O or carbonyl) and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

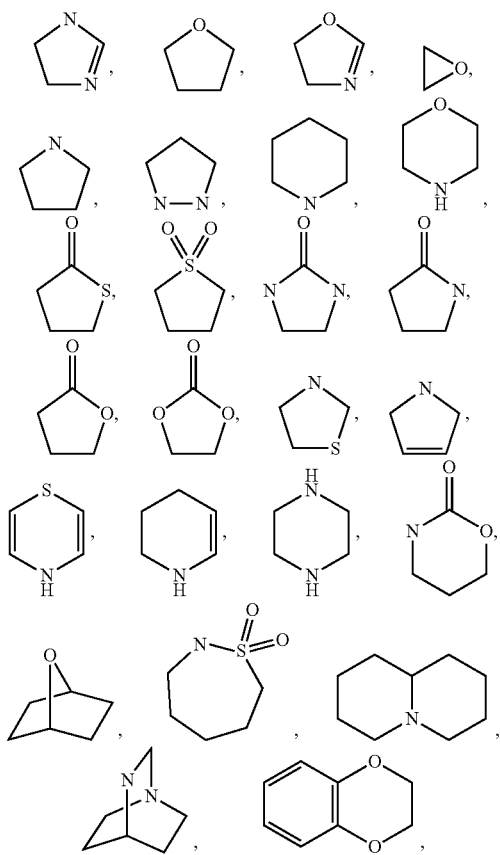

and the like. The term heteroalicyclic also includes all ring forms of the carbohydrates including, but not limited to the monosaccharides, the disaccharides, and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated (i.e., contains a cyclic, delocalized (4n+2) π-electron system in accordance with the Hückel theory). Heteroaryl includes fused or bridged ring systems. In some embodiments, heteroaryl rings have five, six, seven, eight, nine, or more than nine ring atoms. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise specifically in this specification, the term "heteroaryl" is meant to include heteroaryl radicals as defined above which are optionally substituted as defined and described elsewhere herein.

"N-heteroaryl" as used herein refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" as used herein refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" as used herein refers to a radical of the formula —$R^f$-heteroaryl, where $R^f$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" as used herein refers to the —S— radical.

"Sulfinyl" as used herein refers to the —S(=O)— radical.

"Sulfonyl" as used herein refers to the —S(=O)$_2$— radical.

"Amino" as used herein refers to the —NH$_2$ radical.

"Cyano" as used herein refers to the —CN radical.

"Nitro" as used herein refers to the —NO$_2$ radical.

"Oxa" as used herein refers to the —O— radical.

"Oxo" as used herein refers to the =O or carbonyl radical.

"Imino" as used herein refers to the =NH radical.

"Thioxo" as used herein refers to the =S radical.

An "alkoxy" group refers to a (alkyl)O— group, where alkyl is as defined herein For example, CH$_3$CH$_2$—O— corresponds to ethoxy.

An "aryloxy" group refers to an (aryl)O— group, where aryl is as defined herein For example,

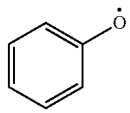

corresponds to phenoxy.

"Carbocyclylalkyl" as used herein means an alkyl radical, as defined herein, substituted with a carbocyclyl group. "Cycloalkylalkyl" as used herein means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl," "heteroalkenyl," and "heteroalkynyl" include optionally substituted alkyl, alkenyl, and alkynyl radicals in which one or more skeletal chain atoms is a heteroatom, for example, oxygen, nitrogen, sulfur, silicon, phosphorus, or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In addition, up to two heteroatoms may be consecutive, such as —CH$_2$—NH—OCH$_3$ and —CH$_2$—O—Si(CH$_3$)$_3$.

The term "heteroatom" as used herein refers to an atom other than carbon or hydrogen. Heteroatoms are typically independently selected from among oxygen, sulfur, nitrogen, silicon, and phosphorus, but are not limited to these heteroatoms. In embodiments in which two or more heteroatoms are present, the two or more heteroatoms can all be the same as one another, or some or all of the two or more heteroatoms can each be different from each other.

The term "bond," "direct bond," or "single bond" as used herein refers to a chemical bond between two atoms, or two moieties when the atoms joined by the bond are considered to be part of larger chemical substructure.

An "isocyanato" group as used herein refers to a —NCO group.

An "isothiocyanato" group as used herein refers to a —NCS group.

The term "moiety" as used herein refers to a specific segment or functional group of a molecule. Chemical moieties are often recognized chemical entities embedded in or appended to a molecule.

A "thioalkoxy" or "alkylthio" group as used herein refers to a —S-alkyl group.

A "alkylthioalkyl" group as used herein refers to an alkyl group substituted with a —S-alkyl group.

As used herein, the term "acyloxy" refers to a group of formula RC(=O)O—.

"Carboxy" as used herein means a —C(O)OH radical.

As used herein, the term "acetyl" refers to a group having the chemical formula —C(=O)CH$_3$.

"Acyl" as used herein refers to the group —C(O)R.

As used herein, the term "trihalomethanesulfonyl" refers to a group having the chemical formula X$_3$CS(=O)$_2$— where X is a halogen.

"Cyanoalkyl" as used herein means an alkyl radical, as defined herein, substituted with at least one cyano group.

As used herein, the term "N-sulfonamido" or "sulfonylamino" refers to a group having the chemical formula RS(=O)$_2$NH—.

As used herein, the term "O-carbamyl" refers to a group having the chemical formula —OC(=O)NR$_2$.

As used herein, the term "N-carbamyl" refers to a group having the chemical formula ROC(=O)NH—.

As used herein, the term "O-thiocarbamyl" refers to a group having the chemical formula —OC(=S)NR$_2$.

As used herein, "N-thiocarbamyl" refers to a group having the chemical formula ROC(=S)NH—.

As used herein, the term "C-amido" refers to a group having the chemical formula —C(=O)NR$_2$.

"Aminocarbonyl" as used herein refers to a —CONH$_2$ radical.

As used herein, the term "N-amido" refers to a group having the chemical formula RC(=O)NH—.

"Hydroxyalkyl" as used herein refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" as used herein refers to an alkyl radical, as defined herein, substituted with an alkoxy group, as defined herein.

An "alkenyloxy" group as used herein refers to a (alkenyl)O— group, where alkenyl is as defined herein.

The term "alkylamine" as used herein refers to the —N(alkyl)$_x$H$_y$ group, where x and y are selected from among x=1, y=1; and x=2, y=0. When x=2, the alkyl groups, taken together with the nitrogen atom to which they are attached, can optionally form a cyclic ring system.

"Alkylaminoalkyl" as used herein refers to an alkyl radical, as defined herein, substituted with an alkylamine, as defined herein.

An "amide" as used herein is a chemical moiety, for example, with the formula —C(O)NHR or —NHC(O)R, where R is selected from among alkyl, cycloalkyl, aryl, heteroaryl (bonded through a ring carbon), and heteroalicyclic (bonded through a ring carbon). An amide moiety may form a linkage between an amino acid or a peptide molecule and a compound described herein, thereby forming for example a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

The term "ester" as used herein refers to a chemical moiety with formula —COOR, where R is selected from among alkyl, cycloalkyl, aryl, heteroaryl (bonded through a ring carbon), and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

As used herein, the term "ring" refers to any covalently closed cyclic structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one or more than one ring.

The term "membered ring" as used herein can embrace any cyclic structure. The term "membered" is meant to denote the number of skeletal atoms that constitute the ring. Thus, for example, cyclohexyl, pyridine, pyran, and thiopyran are 6-membered rings and cyclopentyl, pyrrole, furan, and thiophene are 5-membered rings.

The term "fused" as used herein refers to structures in which two or more rings share one or more bonds.

As described herein, compounds of this disclosure may be "optionally substituted". In general, the term "substituted," whether preceded by the term "optionally" or not, means that one or more hydrogens of a designated moiety is/are replaced with a suitable substituent. Unless otherwise indicated, an "optionally substituted" group may have a suitable substituent at each chemically substitutable position of the group, and when more than one position in any given chemical structure may be substituted with more than one substituent selected from a specified group, the chemical substituent may be either the same or different at every position. Combinations of substituents envisioned by this disclosure are those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$^{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°—, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined herein and is independently hydrogen, C$_{1-6}$ aliphatic, —CH$_2$Ph, —O(CH$_2$)$_{0-1}$Ph, —CH$_2$-(5- to 6-membered heteroaryl ring), or a 5- to 6-membered saturated, partially unsaturated, or aryl ring having zero to four heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having zero to four heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" (e.g., -(haloR$^\bullet$) is substituted only with one or more halogens (e.g., -(halo), -(halo)$_2$, or -(halo)$_3$), and is independently selected from C$_{1-4}$ aliphatic, —CH$_2$Ph, —O(CH$_2$)$_{0-1}$Ph, or a 5- to 6-membered saturated, partially unsaturated, or aryl ring having zero to four heteroatoms independently selected from nitrogen, oxygen, or sulfur. Suitable divalent substituents on a saturated carbon atom of R° include =O (i.e., carbonyl) and =S (i.e., thiocarbonyl).

Suitable divalent substituents on a saturated carbon atom of an "optionally substituted" group include the following: =O (i.e., carbonyl), =S (i.e., thiocarbonyl), =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic or alkyl which may be substituted as defined below, or an unsubstituted 5- to 6-membered saturated, partially unsaturated, or aryl ring having zero to four heteroatoms independently selected from nitrogen, oxygen, or sulfur. Suitable divalent substituents that are bound to vicinal substitutable carbons of an "optionally substituted" group include —O(CR*$_2$)$_{2-3}$O—, wherein each independent occurrence of R* is selected from hydrogen, C$_{1-6}$ aliphatic or alkyl which may be substituted as defined below, or an unsubstituted 5- to 6-membered saturated, partially unsaturated, or aryl ring having zero to four heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" (supra) is substituted only with one or more halogens, and is independently $C_{1-4}$ aliphatic, —CH$_2$Ph, —O(CH$_2$)$_{0-1}$Ph, or a 5- to 6-membered saturated, partially unsaturated, or aryl ring having zero to four heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5- to 6-membered saturated, partially unsaturated, or aryl ring having zero to four heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having zero to four heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" (supra) is substituted only with one or more halogens, and is independently $C_{1-4}$ aliphatic, —CH$_2$Ph, —O(CH$_2$)$_{0-1}$Ph, or a 5- to 6-membered saturated, partially unsaturated, or aryl ring having zero to four heteroatoms independently selected from nitrogen, oxygen, or sulfur.

The term "nucleophile" or "nucleophilic" as used herein refers to an electron rich compound, or chemical moiety thereof.

The term "electrophile" or "electrophilic" as used herein refers to an electron poor or electron deficient molecule, or chemical moiety thereof. Examples of electrophiles include, but in no way are limited to, Michael acceptor moieties (e.g., α,β-unsaturated carbonyls).

The term "acceptable" or "pharmaceutically acceptable," as used herein with respect to a formulation, composition, or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of a compound or composition described herein.

"Bioavailability" as used herein refers to the percentage of the weight of compounds disclosed herein, such as, compounds of any of Formulae (I)-(XLIIIc) dosed or delivered into the general circulation of the animal or human being studied. The total exposure (AUC$_{(0-\infty)}$) of a drug when administered intravenously is usually defined as 100% bioavailable (F %). "Oral bioavailability" as used herein refers to the extent to which compounds disclosed herein, such as, compounds of any of Formulae (I)-(XLIIIc) are absorbed into the general circulation when the pharmaceutical composition is taken orally as compared to intravenous injection.

"Blood plasma concentration" as used herein refers to the concentration of compounds disclosed herein, such as, compounds of any of Formulae (I)-(XLIIIc) in the plasma component of blood of a subject. It is understood that the plasma concentration of compounds of any of Formulae (I)-(XLIIIc) may vary significantly between subjects, due to variability with respect to metabolism and/or possible interactions with other therapeutic agents. In accordance with some embodiments disclosed herein, the blood plasma concentration of the compounds of any of Formulae (I)-(XLIIIc) may vary from subject to subject. Likewise, values such as maximum plasma concentration ($C_{max}$) or time to reach maximum plasma concentration ($T_{max}$), or total area under the plasma concentration time curve (AUC$_{(0-\infty)}$) may vary from subject to subject. Due to this variability, the amount necessary to achieve "a therapeutically effective amount" of a compound of any of Formulae (I)-(XLIIIc) may vary from subject to subject.

The terms "co-administration" or the like, as used herein, are meant to encompass administration of the described selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of a described agent or a compound being administered that will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic use is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formulae (I)-(XLIIIc), age, weight, general condition of the subject, the condition being treated, the severity of the condition being treated, and the judgment of the prescribing physician. By way of example only, therapeutically effective amounts may be determined by routine experimentation including, but not limited to a dose escalation clinical trial.

As used herein, the terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages describe the "percent identity" of two or more sequences. The identity of a sequence can exist over a region that is at least about 75-100 sequential units in length, over a region that is about fifty sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about fifty amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about fifty nucleic acids in length, or, where not specified, across the entire sequence of a polynucleotide sequence.

The term "isolated," as used herein, refers to separating and removing a component of interest from (natural) components not of interest. Isolated substances can be in either a dry or semi-dry state, or in solution including, but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

As used herein, a "metabolite" of a compound disclosed herein is a derivative of that compound that is formed when the compound is metabolized. The term "active metabolite" as used herein refers to a biologically active derivative of a compound that is formed when the compound is metabolized. The term "metabolized," as used herein, refers to the sum of the processes (including, but not limited to hydrolysis reactions and reactions catalyzed by enzymes, such as, oxidation reactions) by which a particular substance is changed by an organism. Thus, enzymes may produce specific structural alterations to a chemical compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines, and free sulfhydryl groups. Further information on metabolism may be obtained from The Pharmacological Basis of Therapeutics, 9th Edition, McGraw-Hill (1996). Metabolites of the compounds disclosed herein can be identified either by administration of (parent) compounds to a host and analysis of tissue samples from the host, or by incubation of (parent) compounds with hepatic cells in vitro and analysis of the resulting compounds. Both methods are well known in the art. In some embodiments, metabolites of a (parent) compound are formed by oxidative processes and correspond to the corresponding hydroxy-containing compound. In some embodiments, a (parent) compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "covalent inhibitor," as used herein, refers to a compound that, upon contact with a target protein (e.g., menin) causes the formation of a new covalent bond with or within the protein, whereby one or more of the target protein's biological activities (e.g., phosphotransferase activity) is altered, diminished, or abolished notwithstanding the subsequent presence or absence of the covalent or irreversible inhibitor. In certain embodiments, a covalent inhibitor is irreversible. In contrast, a noncovalent inhibitor compound upon contact with a target protein does not cause the formation of a new covalent bond with or within the protein and therefore can associate and dissociate from the target protein.

The term "covalent inhibitor of menin-MLL protein-protein interaction" as used herein, refers to an inhibitor of menin that can form a covalent bond with an amino acid residue of menin. In one embodiment, the covalent or irreversible inhibitor of menin can form a covalent bond with a Cys residue of menin; in particular embodiments, the covalent inhibitor can form a covalent bond with a Cys 329 residue (or a homolog thereof) of menin. In certain embodiments, a covalent inhibitor is irreversible.

The term "prophylactically effective amount," as used herein, refers that amount of a composition applied to a patient that will relieve to some extent one or more of the symptoms of a disease, condition, or disorder being treated. In such prophylactic applications, such amounts may depend on the patient's state of health, weight, and the like. It is considered well within the skill of the art for one to determine such prophylactically effective amounts by routine experimentation, including, but not limited to a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, such as menin, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other (natural) components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" or "patient" as used herein, refers to an animal which is the object of treatment, observation, or experiment. By way of example only, a subject may be, but is not limited to, a mammal including, but not limited to a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition (e.g., diabetes mellitus).

As used herein, the term "target protein" refers to a molecule or a portion of a protein capable of being bound by a selective binding compound. In certain embodiments, a target protein is menin.

The terms "treat," "treating," or "treatment" as used herein, include alleviating, abating, or ameliorating a disease or condition symptoms, preventing additional symptoms, ameliorating or preventing the underlying metabolic causes of symptoms, inhibiting the disease or condition, for example, arresting the development of the disease or condition, relieving the disease or condition, causing regression of the disease or condition, relieving a condition caused by the disease or condition, or stopping the symptoms of the disease or condition. The terms "treat," "treating," or "treatment," as used herein include, but are not limited to, prophylactic and/or therapeutic treatments.

As used herein, the $IC_{50}$ refers to an amount, concentration, or dosage of a particular test compound that achieves a 50% inhibition of a maximal response, such as inhibition of menin-MLL, in an assay that measures such response.

As used herein, $EC_{50}$ refers to a dosage, concentration, or amount of a particular test compound that elicits a dose-dependent response at 50% of maximal expression of a particular response that is induced, provoked, or potentiated by the particular test compound.

Methods described herein include administering to a subject in need (e.g., a subject suffering from diabetes mellitus) a composition described herein containing a therapeutically effective amount of one or more Menin-MLL inhibitor compounds described herein.

In some embodiments, methods described herein can be used to treat diabetes mellitus, which includes, but is not limited to, type 1 diabetes, type 2 diabetes, gestational diabetes, maturity onset diabetes of the young, steroid diabetes, and double diabetes.

Symptoms, diagnostic tests, and prognostic tests for each of the above-mentioned conditions are known to those of skill in the art. See, for example, Hartling L, et al., "Screening and diagnosing gestational diabetes mellitus," *Evid Rep Technol Assess*, 2012, 1-327; PMID: 24423035; Kaur G, et al., "Diagnostic accuracy of tests for type 2 diabetes and prediabetes: A systematic review and meta-analysis," *PLoS One*, 2020, 15(11):e0242415, PMID: 33216783; and Gan W Z, et al., "Omics-based biomarkers in the diagnosis of diabetes," *J Basic Clin Physiol Pharmacol*, 2019, 31(2), PMID: 31730525.

A number of animal models are useful for establishing a range of therapeutically effective doses of Menin-MLL inhibitor compounds described herein for treating any of the foregoing diseases.

For example, dosing of Menin-MLL inhibitor compounds described herein for treating diabetes mellitus can be assessed in a mouse model of diabetes mellitus for instance with mice bearing ob, db, ob/ob, db/db, or ob/db mutations.

The therapeutic efficacy of a provided compound for one of the foregoing diseases can be optimized during a course of treatment. For example, a subject being treated can undergo a diagnostic evaluation to correlate the relief of disease symptoms or pathologies to inhibition of in vivo menin-MLL activity achieved by administering a given dose of an Menin-MLL inhibitor described herein.

Compounds

In the following description of Menin-MLL inhibitor compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques, and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known to a person of skill in the art. Standard techniques can be used for chemical syntheses, chemical analyses, pharmaceutical preparation, formulation, and delivery, and treatment of patients.

Menin-MLL inhibitor compounds can be used for the manufacture of a medicament for treating any of the foregoing conditions (e.g., diabetes mellitus).

In some embodiments, the Menin-MLL inhibitor compound used for the methods described herein inhibits menin-MLL activity with an in vitro $IC_{50}$ of less than about 10 μM (e.g., less than about 1 μM, less than about 0.5 μM, less than about 0.4 μM, less than about 0.3 μM, less than about 0.1 μM, less than about 0.08 μM, less than about 0.06 μM, less than about 0.05 μM, less than about 0.04 μM, less than about 0.03 µM, less than about 0.02 µM, less than about 0.01 µM, less than about 0.008 µM, less than about 0.006 µM, less than about 0.005 µM, less than about 0.004 µM, less than about 0.003 µM, less than about 0.002 µM, less than about 0.001 µM, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092 µM, or less than about 0.00090 µM).

In some embodiments, the Menin-MLL inhibitor compound selectively inhibits an activated form of its target menin.

Also described herein are methods for synthesizing such covalent inhibitors, methods for using such covalent inhibitors in the treatment of diseases (including diseases wherein inhibition of menin-MLL interaction provides therapeutic benefit to a patient having the disease). Further described are pharmaceutical compositions that include an inhibitor of menin-MLL interaction.

Specifically described herein are covalent inhibitors of menin-MLL interaction that form a covalent bond with a cysteine residue on menin. Further described herein are covalent inhibitors of menin-MLL interaction that form a covalent bond with a Cys329 residue on menin. Also described are pharmaceutical formulations that include a covalent inhibitor of menin.

The menin inhibitor compounds described herein are selective for menin having a cysteine residue in an amino acid sequence position of the menin protein that is homologous to the amino acid sequence position of cysteine329 in menin. Covalent inhibitor compounds described herein include a Michael acceptor moiety.

Generally, a noncovalent or covalent inhibitor compound of menin used in the methods described herein is identified or characterized in an in vitro assay, for example, an acellular biochemical assay or a cellular functional assay. Such assays are useful to determine an in vitro $IC_{50}$ for a noncovalent or covalent menin inhibitor compound.

Further, covalent complex formation between menin and a candidate covalent menin inhibitor is a useful indicator of covalent inhibition of menin that can be readily determined by a number of methods known in the art (e.g., mass spectrometry). For example, some covalent menin-inhibitor compounds can form a covalent bond with Cys329 of menin (e.g., via a Michael reaction). See S. Xu et al. Angewandte Chemie International Ed. 57(6), 1601-1605 (2017) (incorporated by reference in its entirety).

Described herein are compounds of any of Formulae (I)-(XLIIIc). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite, or pharmaceutically acceptable prodrug of such compound are provided. In some embodiments, when compounds disclosed herein contain an oxidizable nitrogen atom, the nitrogen atom can be converted to an N-oxide by methods well known to those of skill in the art. In certain embodiments, isomers and chemically protected forms of compounds having a structure represented by any of Formulae (I)-(XLIIIc) are also provided.

In some embodiments, provided are menin-MLL covalent inhibitors according to compounds of Formulae (I)-(XLIIIc).

In some embodiments, provided is a compound according to Formula (I) having the structure:

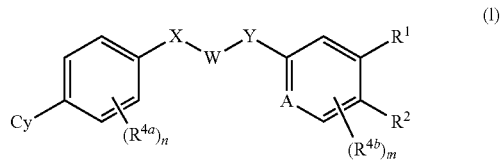

or a pharmaceutically acceptable salt thereof, wherein
A is carbon or nitrogen;
Cy is substituted or unsubstituted

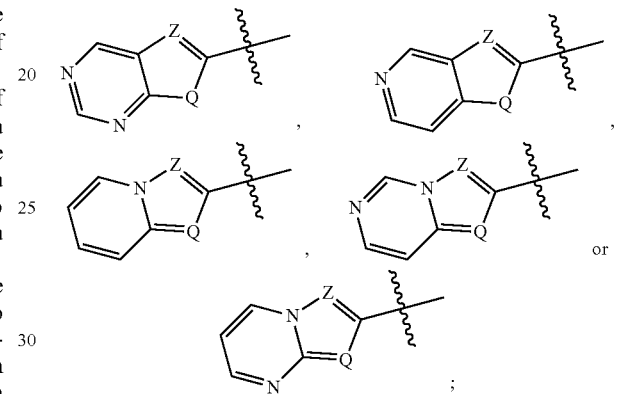

Q is nitrogen, —N(H)—, —O—, or —S—;
Z is —$CR^{5a}$= or —N=;
X is —$NR^{3a}$—, —$C(R^{3b})_2$—, or —O—;
Y is a single bond, —$NR^{3a}$—, —$C(R^{3b})_2$—, or —O—;
W is —C(O)—, —S(O)—, or —$S(O)_2$—;
one of IV and $R^2$ is $Cy^2$-N(H)C(O)—C($R^{6a}$)=C($R^{6b}$)($R^{6c}$), or $CH_2$-$Cy^2$-N(H)C(O)—C($R^{6a}$)=C($R^{6b}$)($R^{6c}$); and other is hydrogen, $C_{1-6}$ alkyl, $C_{1-6}$ haloalkyl, halo, or CN;
$Cy^2$ is an optionally substituted group selected from phenyl, pyridyl, or a 4- to 7-membered heterocycloalkyl ring having one to two heteroatoms independently selected from nitrogen, oxygen, or sulfur;
each $R^{3a}$ and $R^{4b}$ is independently hydrogen or $C_{1-6}$ alkyl;
each $R^{4a}$ and $R^{4b}$ is independently hydrogen, halo, CN, OR, —$N(R)_2$, —C(O)N(R)$_2$, —NRC(O)R, —$SO_2$R, —C(O)R, —$CO_2$R, or an optionally substituted group selected from $C_{1-6}$ alkyl, $C_{3-7}$ cycloalkyl, a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur;
each R is independently hydrogen, or an optionally substituted group selected from $C_{1-6}$ aliphatic, phenyl, an 8- to 10-membered bicyclic aryl ring, a 4- to 7-membered saturated or partially unsaturated heterocyclic ring having one to two heteroatoms independently selected from nitrogen, oxygen, or sulfur, and a 5- to 6-membered heteroaryl ring having one to four heteroatoms independently selected from nitrogen, oxygen, or sulfur; or two R groups on the same nitrogen are taken together with their intervening atoms to form a 4- to 7-membered saturated, partially unsaturated, or heteroaryl ring having zero to three heteroatoms, in addition to the nitrogen, independently selected from nitrogen, oxygen, or sulfur;

$R^{5a}$ is hydrogen, $C_{1-6}$ alkyl, $C_{1-6}$ haloalkyl, halo, or CN;

each $R^{6a}$ and $R^{6b}$ is independently hydrogen or $C_{1-6}$ alkyl; or $R^{6a}$ and $R^{6b}$ are joined together to form a bond;

$R^{6c}$ is hydrogen or substituted or unsubstituted $C_{1-6}$ alkyl;

m is one, two, or three; and n is one, two, three, or four.

In some embodiments, W is —S(O)— or —S(O)$_2$—.

In some embodiments, W is —C(O)—.

In some embodiments, X is —NR$^{3a}$—; and Y is —C(R$^{3b}$)$_2$—, —NR$^{3b}$—, or —O—.

In some embodiments, Y is a single bond, or —NR$^{3a}$—; and X is —C(R$^{3b}$)$_2$—, —NR$^{3b}$—, or —O—.

In some embodiments, each of X and Y is independently —NR$^{3a}$—.

In some embodiments, R$^{3a}$ is hydrogen.

In some embodiments, R$^{3b}$ is hydrogen or methyl.

In some embodiments, each of X and Y is —N(H)—.

In some embodiments, —X—W—Y— is —N(H)—C(O)—N(H)—, —N(H)—C(O)—CH$_2$—, —CH$_2$—C(O)—N(H)—, —N(H)—S(O)—N(H)—, —N(H)—S(O)—CH$_2$—, —CH$_2$—S(O)—N(H)—, —N(H)—S(O)$_2$—N(H)—, —N(H)—S(O)$_2$—CH$_2$—, —CH$_2$—S(O)$_2$—N(H)—, or —N(H)—C(O)—.

In some embodiments, R$^1$ is Cys-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^2$ is hydrogen, halo, hydroxyl, CN, substituted or unsubstituted $C_{1-6}$ alkyl, substituted or unsubstituted amino, or substituted or unsubstituted alkoxy.

In some embodiments, R$^1$ is Cy$^2$-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^2$ is hydrogen, Me, Et, i-Pr, CF$_3$, F, Cl, OMe, OEt, or CN.

In some embodiments, R$^1$ is Cy$^2$-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^2$ is hydrogen.

In some embodiments, R$^2$ is Cy$^2$-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^1$ is hydrogen, halo, hydroxyl, CN, substituted or unsubstituted $C_{1-6}$ alkyl, substituted or unsubstituted amino, or substituted or unsubstituted alkoxy.

In some embodiments, R$^2$ is Cy$^2$-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^1$ is hydrogen, Me, Et, i-Pr, CF$_3$, F, Cl, OMe, OEt, or CN.

In some embodiments, R$^2$ is Cy$^2$-N(H)C(O)—C(R$^{6a}$)═C(R$^{6b}$)(R$^{6c}$), or CH$_2$-Cy$^2$-N(H)C(O)—C(R$^{6a}$)═C(R$^{6b}$)(R$^{6c}$); and R$^1$ is hydrogen.

The compound according claim 1, wherein —X—W—Y— is —N(H)—C(O)—; R$^1$ is —CH$_2$-Cy$^2$-N(H)C(O)—C(R$^{6a}$)═C(R$^{6b}$)(R$^{6c}$); and R$^2$ is hydrogen.

In some embodiments, the compound is according to Formula (XXI)

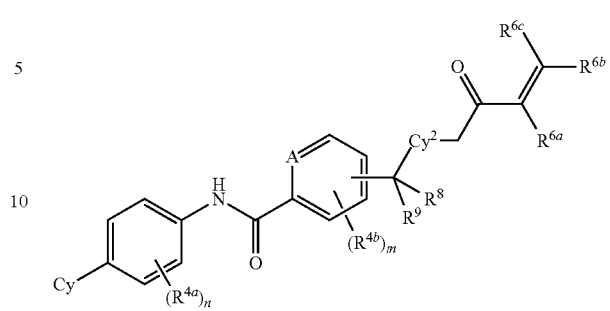

or a pharmaceutically acceptable salt thereof, wherein
A, Cy, Cy$^2$, R$^{4b}$, R$^{6a}$, R$^{6b}$, R$^{6c}$, m, and n are as described for Formula (I); and each R$^8$ and R$^9$ is independently hydrogen, $C_{1-6}$ alkyl, $C_{1-6}$ haloalkyl, halo, or CN.

In some embodiments, one of R$^8$ and R$^9$ is hydrogen, halo, hydroxyl, CN, substituted or unsubstituted $C_{1-6}$ alkyl, substituted or unsubstituted amino, or substituted or unsubstituted alkoxy; and the other is hydrogen.

In some embodiments, each R$^8$ and R$^9$ is hydrogen or methyl.

In some embodiments, each R$^8$ and R$^9$ is hydrogen.

In some embodiments, A is nitrogen.

In some embodiments, A is carbon.

In some embodiments, m is one or two.

In some embodiments, n is one or two.

In some embodiments, each R$^{4a}$ is independently hydrogen, halo, hydroxyl, CN, substituted or unsubstituted $C_{1-6}$ alkyl, substituted or unsubstituted amino, or substituted or unsubstituted alkoxy.

In some embodiments, each R$^{4a}$ is independently hydrogen, Me, Et, i-Pr, CF$_3$, F, Cl, OMe, OEt, or CN.

In some embodiments, each R$^{4a}$ is hydrogen.

In some embodiments, each R$^{4b}$ is independently hydrogen, halo, hydroxyl, CN, substituted or unsubstituted $C_{1-6}$ alkyl, substituted or unsubstituted amino, or substituted or unsubstituted alkoxy.

In some embodiments, each R$^{4b}$ is independently hydrogen, Me, Et, i-Pr, CF$_3$, F, Cl, OMe, OEt, or CN.

In some embodiments, each R$^{4b}$ is hydrogen.

In some embodiments, the compound is according to Formula (IIa), (IIb), (IIc), or (IId)

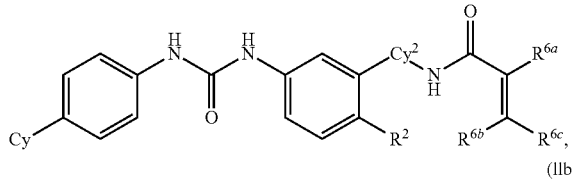

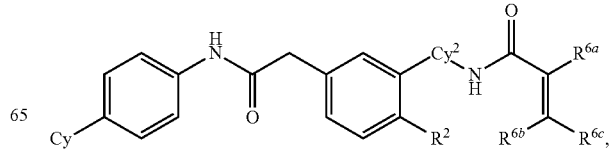

-continued

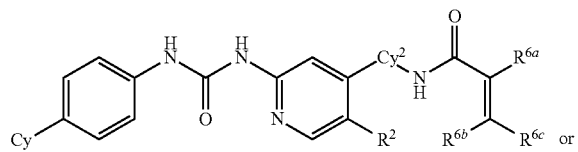
(IIc)

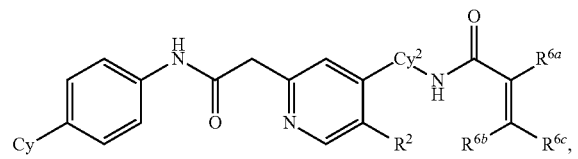
(IId)

or a pharmaceutically acceptable salt thereof.

In some embodiments, $R^2$ is hydrogen, Me, Et, i-Pr, $CF_3$, F, Cl, OMe, OEt, or CN.

In some embodiments, $R^2$ is hydrogen.

In some embodiments, the compound is according to Formula (XXIIa) or (XXIIb)

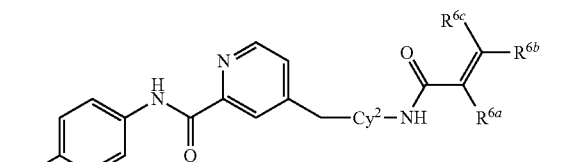
(XXIIa)

(XXIIb)

or a pharmaceutically acceptable salt thereof; wherein Cy, $Cy^2$, $R^{6a}$, $R^{6b}$, or $R^{6c}$ are as described for Formula (I).

In some embodiments, the compound is according to Formula (IIIa), (IIIb), (IIIc), or (IIId)

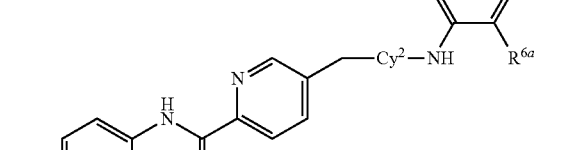
(IIIa)

-continued

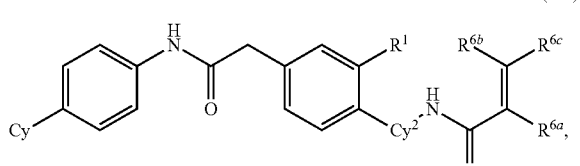
(IIIb)

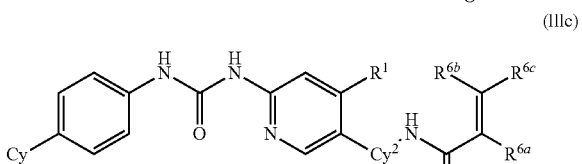
(IIIc)

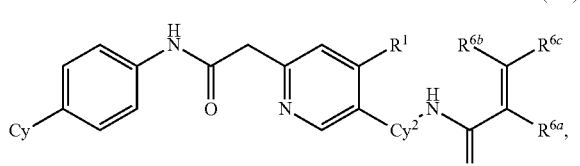
(IIId)

or a pharmaceutically acceptable salt thereof.

In some embodiments, the compound is according to Formula (XXXIIa), (XXXIIb), (XXXIIc), (XXXIId), (XXXIIe), or (XXXIIf)

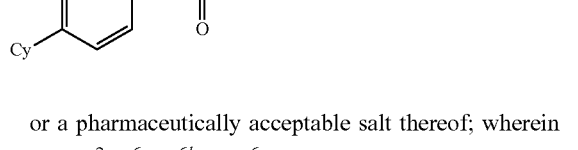
(XXXIIa)

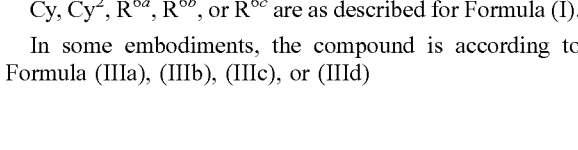
(XXXIIb)

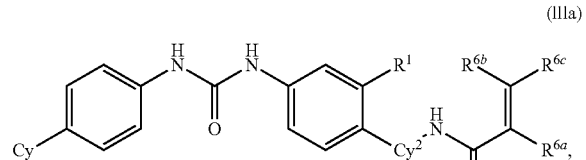
(XXXIIc)

(XXXIId)

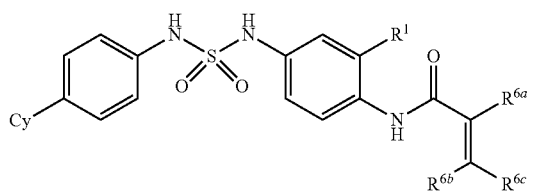
(XXXIIe)

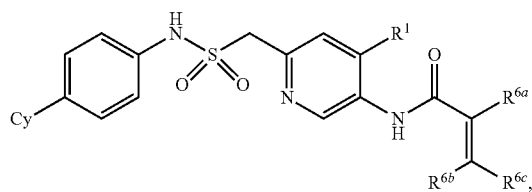
(XXXIIf)

or a pharmaceutically acceptable salt thereof.

In some embodiments, $R^1$ is hydrogen, Me, Et, i-Pr, $CF_3$, F, Cl, OMe, OEt, or CN.

In some embodiments, $R^1$ is hydrogen.

In some embodiments, the compound is according to formula (XXXIIIa), (XXXIIIb), (XXXIIIc), (XXXIIId), (XXXIIIe), or (XXXIIIf)

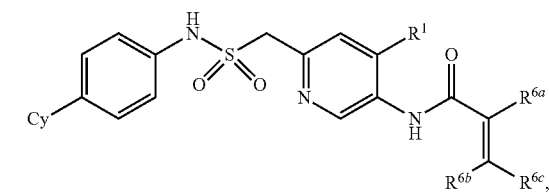
(XXXIIIa)

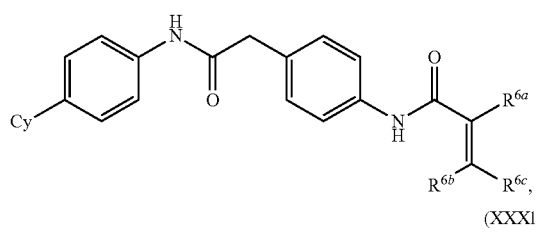
(XXXIIIb)

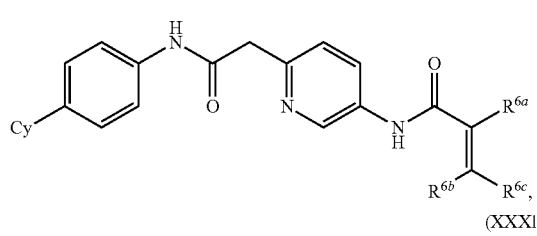
(XXXIIIc)

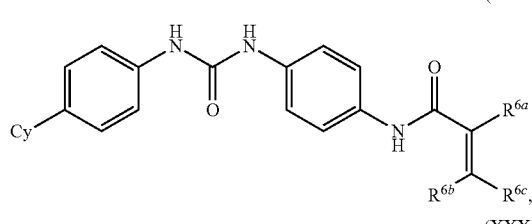
(XXXIIId)

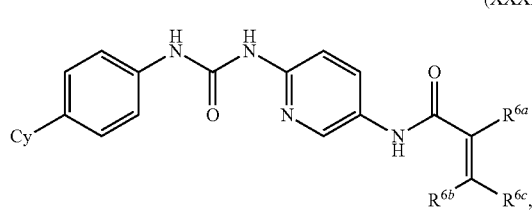

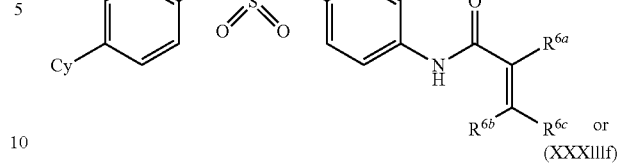
(XXXIIIe)

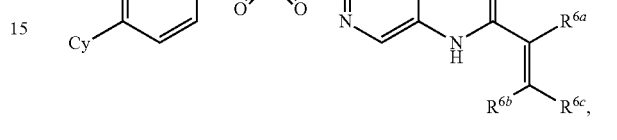
(XXXIIIf)

or a pharmaceutically acceptable salt thereof.

In some embodiments, $Cy^2$ is substituted or unsubstituted phenyl, pyridyl, azetidinyl, pyrrolidinyl, piperidinyl, or azepinyl.

In some embodiments, the compound is according to Formula (IVa) or (IVb)

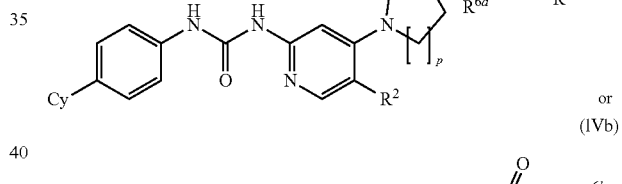
(IVa)

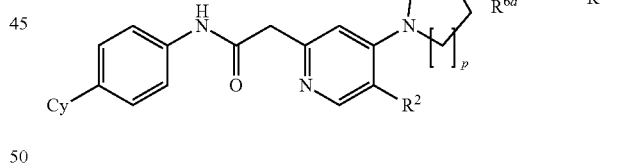
(IVb)

or a pharmaceutically acceptable salt thereof; and wherein p is zero, one, two, or three.

In some embodiments, the compound is according to Formula (XXIIIa) or (XXIIIb)

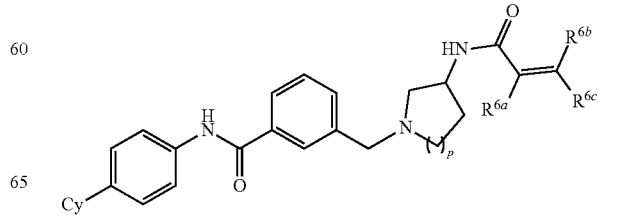
(XXIIIa)

-continued

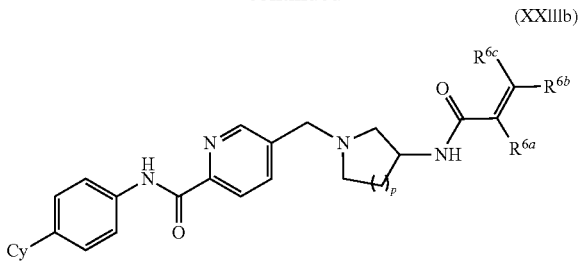
(XXIIIb)

or a pharmaceutically acceptable salt thereof; and wherein p is zero, one, two, or three.

In some embodiments, Cy is substituted or unsubstituted

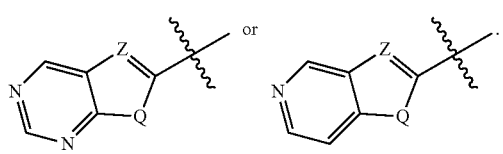

In some embodiments, Cy is substituted or unsubstituted

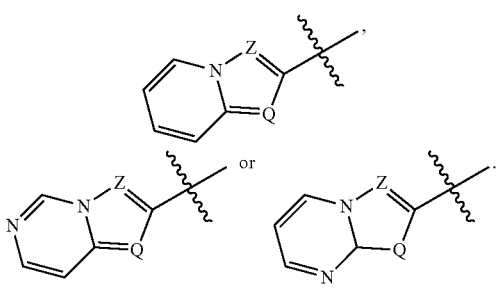

In some embodiments, Q is —N(H)—.
In some embodiments, Q is —O—.
In some embodiments, Q is —S—.
In some embodiments, Z is —N=.
In some embodiments, Z is —$CR^{5a}$=.
In some embodiments, $R^{5a}$ is hydrogen, Me, Et, i-Pr, Cl, F, $CF_3$, or CN.
In some embodiments, $R^{5a}$ is hydrogen, Me, or F.
In some embodiments, $R^{5a}$ is hydrogen.
In some embodiments, Z is —C(H)=.
In some embodiments, Cy is

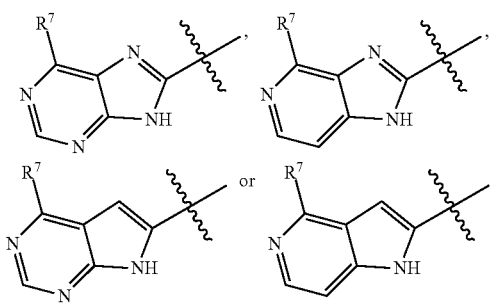

wherein $R^7$ is an optionally substituted group selected from a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur.

In some embodiments, Cy is substituted or unsubstituted

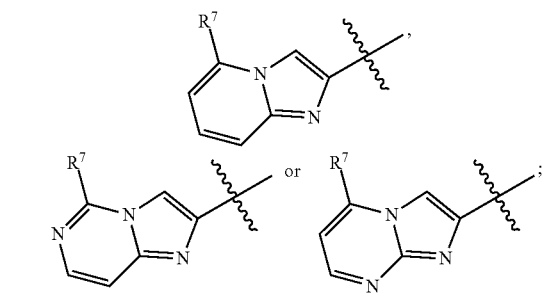

wherein $R^7$ is an optionally substituted group selected from a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur.

In some embodiments, the compound is according to Formula (Va) or (Vb)

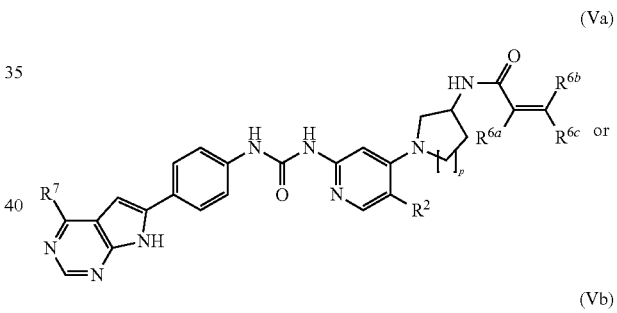
(Va)

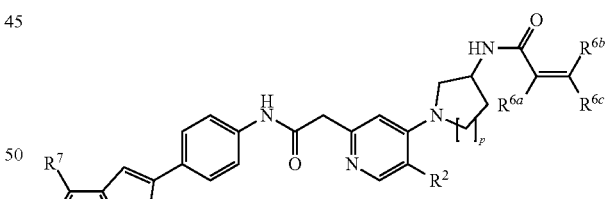
(Vb)

or a pharmaceutically acceptable salt thereof; and wherein p is zero, one, two, or three; and
$R^7$ is an optionally substituted group selected from a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur.

In some embodiments, the compound is according to Formula (XXIVa) or (XXIVb)

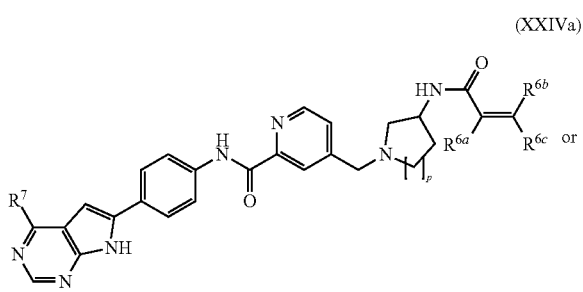

(XXIVa)

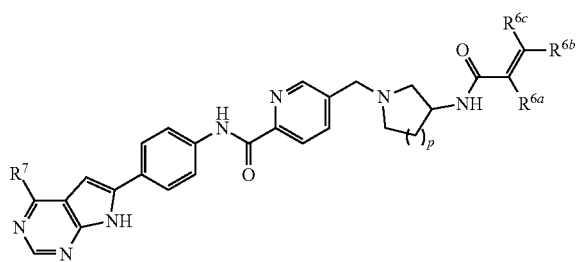

(XXIVb)

or a pharmaceutically acceptable salt thereof; and wherein p is zero, one, two, or three; and R⁷ is an optionally substituted group selected from a 4- to 7-membered heterocycloalkyl ring having one to two heteroatoms independently selected from nitrogen, oxygen, or sulfur, phenyl, an 8- to 10-membered bicyclic aryl ring, and a 5- to 6-membered heteroaryl ring having one to four heteroatoms independently selected from nitrogen, oxygen, or sulfur.

In some embodiments, the compound is according to Formula (XXXIVa) or (XXXIVb)

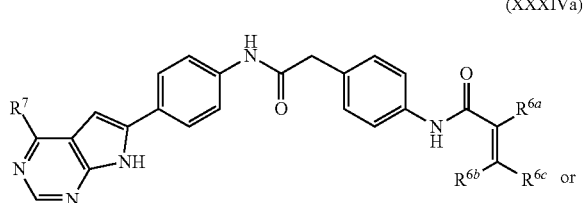

(XXXIVa)

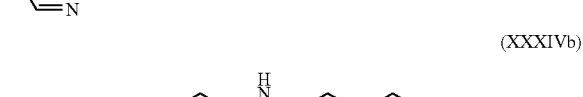

(XXXIVb)

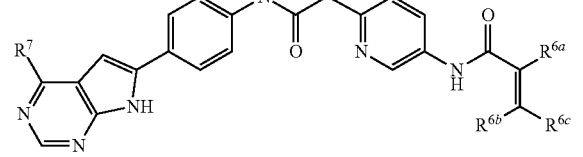

or a pharmaceutically acceptable salt thereof.

In some embodiments, the compound is according to Formula (XXXVa) or (XXXVb)

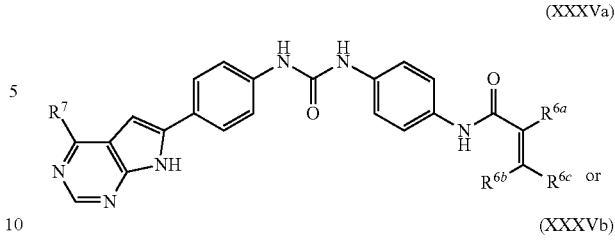

(XXXVa)

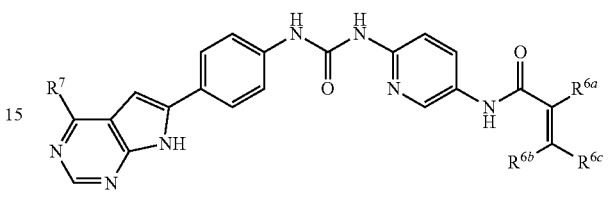

(XXXVb)

or a pharmaceutically acceptable salt thereof.

In some embodiments, the compound is according to Formula (XXXVIa) or (XXXVIb)

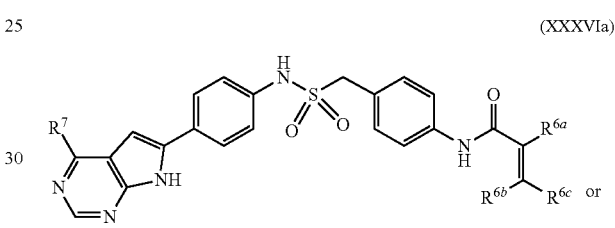

(XXXVIa)

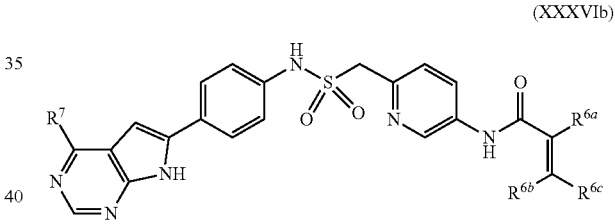

(XXXVIb)

or a pharmaceutically acceptable salt thereof.

In some embodiments, R⁷ is 4- to 7-membered heterocycloalkyl ring having one to two heteroatoms independently selected from nitrogen, oxygen, or sulfur wherein nitrogen is optionally substituted with Me, Et, or i-Pr.

In some embodiments, R⁷ is pyrrolidinyl, piperidinyl, piperazinyl, or morpholinyl.

In some embodiments, R⁷ is morpholinyl.

In some embodiments, R⁷ is substituted or unsubstituted heteroaryl.

In some embodiments, R⁷ is substituted or unsubstituted pyridyl or pyrimidyl.

In some embodiments, R⁷ is unsubstituted pyridyl.

In some embodiments, R⁷ is pyridyl substituted with halo, hydroxyl, CN, substituted or unsubstituted $C_{1-6}$ alkyl, substituted or unsubstituted amino, or substituted or unsubstituted alkoxy.

In some embodiments, R⁷ is pyridyl substituted with Me, Et, i-Pr, OH, C, F, $CF_3$, CN, or $NH_2$.

In some embodiments, R⁷ is pyridyl substituted with Me, Et, i-Pr, Cl, F, $CF_3$, or CN.

In some embodiments, R⁷ is substituted or unsubstituted pyrrolyl, pyrazolyl, imidazolyl, oxazolyl, triazolyl, thiazolyl, oxadiazolyl, or thiadiazolyl.

In some embodiments, $R^7$ is substituted or unsubstituted imidazolyl.

In some embodiments, $R^7$ is imidazoyl substituted with Me, Et, i-Pr, Cl, F, $CF_3$, or CN.

In some embodiments, $R^7$ is imidazoyl substituted with methyl.

In some embodiments, the compound is according to Formula (VIa) or (VIb)

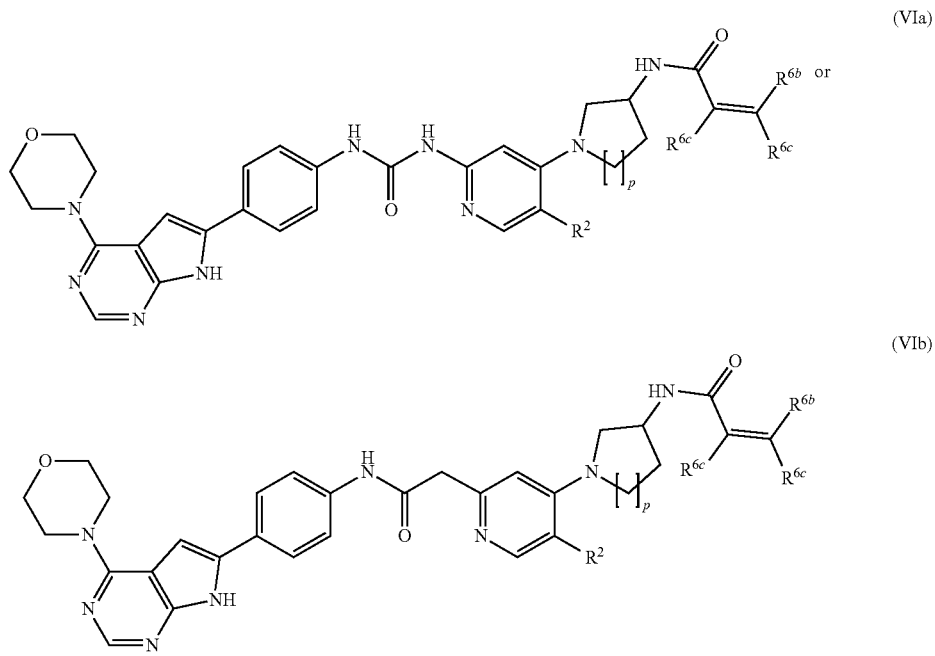

or a pharmaceutically acceptable salt thereof; and wherein p is zero, one, two, or three.

In some embodiments, the compound is according to Formula (XXVa) or (XXVb)

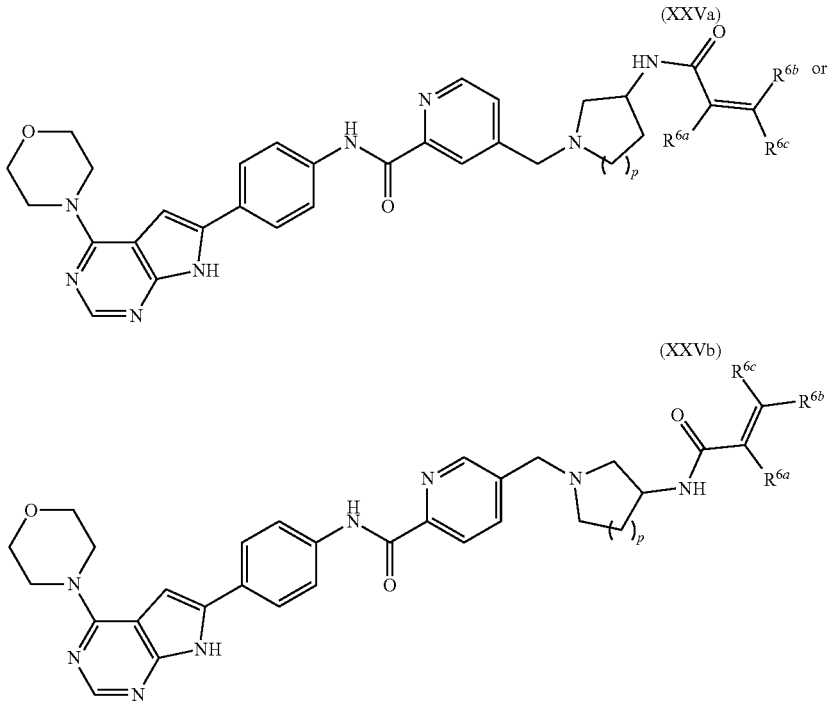

or a pharmaceutically acceptable salt thereof; and wherein p is zero, one, two, or three.

In some embodiments, p is zero, one, or two.
In some embodiments, $R^2$ is hydrogen or F.
In some embodiments, $R^2$ is hydrogen.
In some embodiments, the compound is according to Formula (VIIa), (VIIb), or (VIIc)

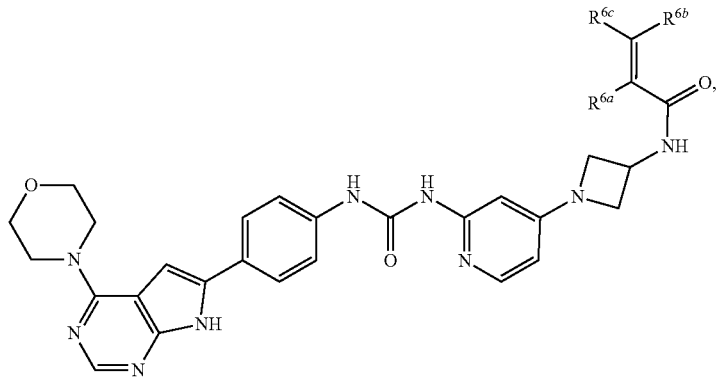
(VIIa)

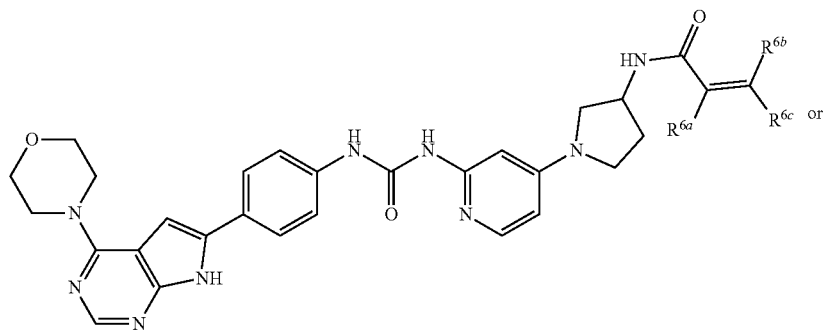
(VIIb) or

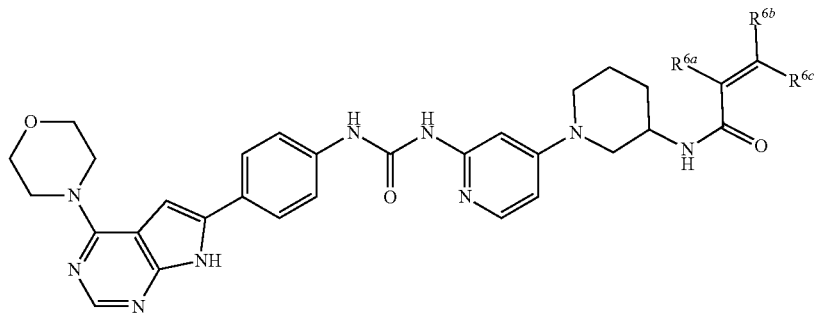
(VIIc)

or a pharmaceutically acceptable salt thereof.

In some embodiments, the compound is according to Formula (VIIIa), (VIIIb), or (VIIIc)

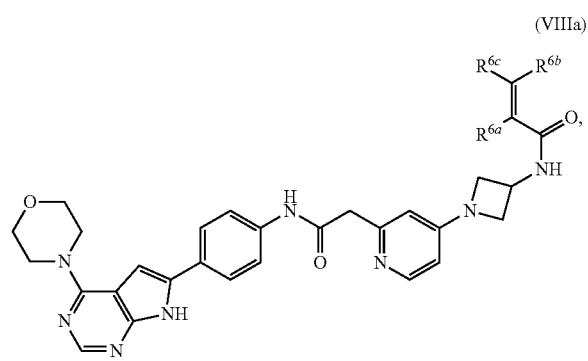
(VIIIa)
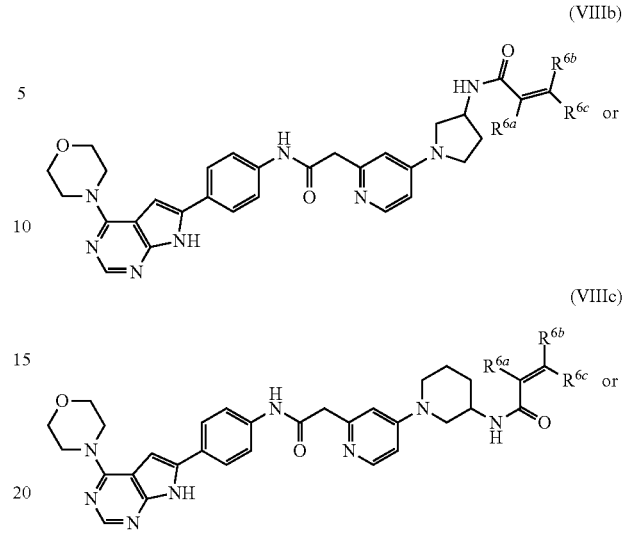
(VIIIb)
(VIIIc)
or a pharmaceutically acceptable salt thereof.
In some embodiments, the compound is according to Formula (XXVIa), (XXVIb), or (XXVIC)
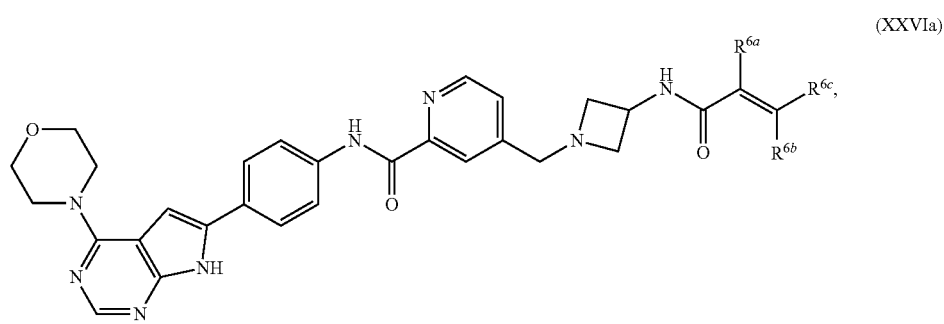
(XXVIa)
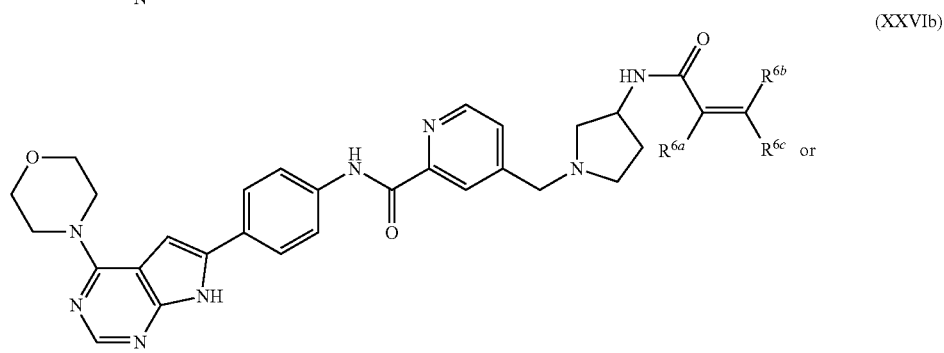
(XXVIb)
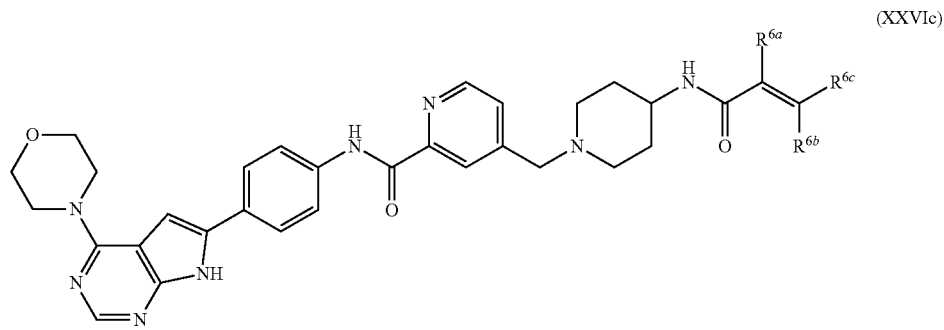
(XXVIc)
or a pharmaceutically acceptable salt thereof.

In some embodiments, the compound is according to Formula (XXXVIIa) or (XXXVIIb)

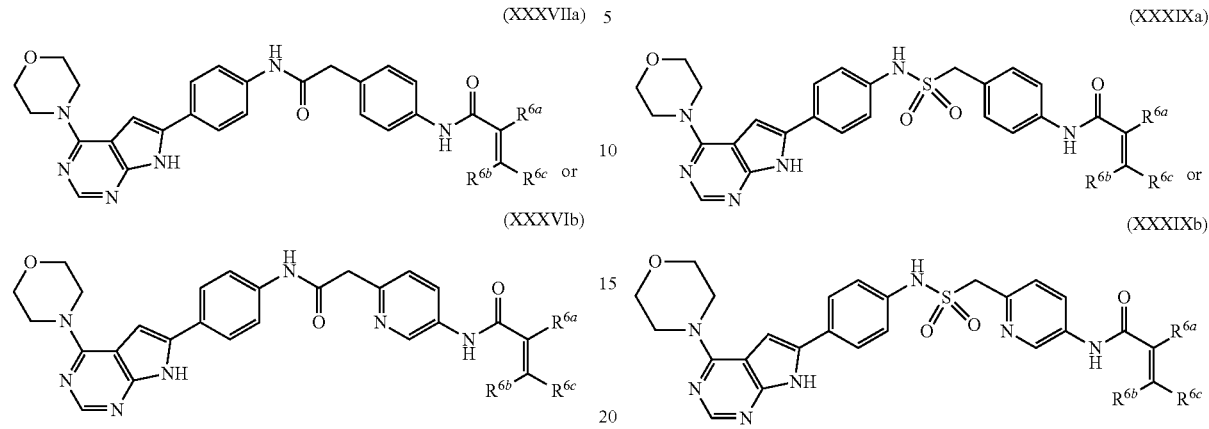

or a pharmaceutically acceptable salt thereof.

In some embodiments, the compound is according to Formula (XXXVIIIa) or (XXXVIIIb)

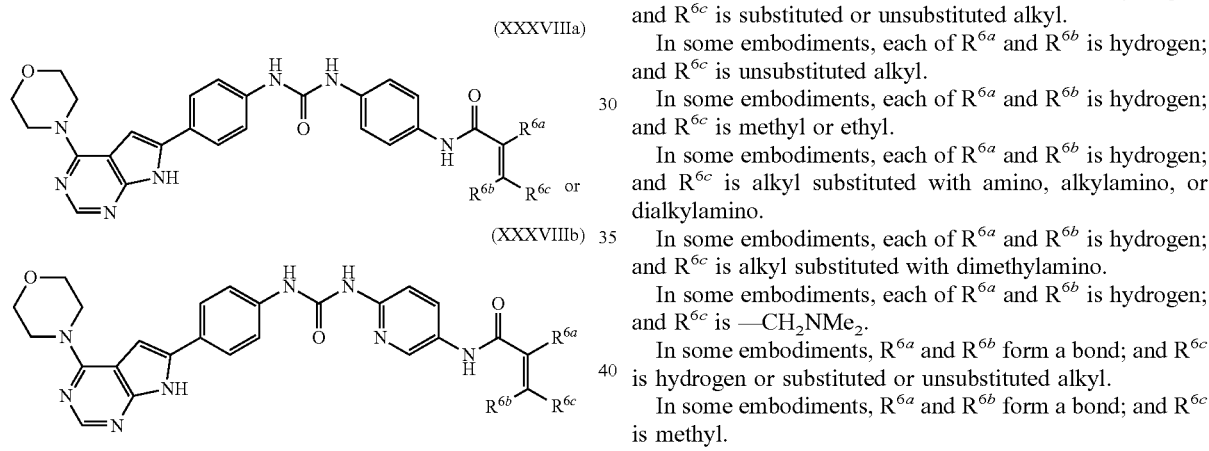

or a pharmaceutically acceptable salt thereof.

In some embodiments, the compound is according to Formula (XXXIXa) or (XXXIXb)

(XXXIXa)

(XXXIXb)

or a pharmaceutically acceptable salt thereof.

In some embodiments, each of $R^{6a}$, $R^{6b}$, and $R^{6c}$ is hydrogen.

In some embodiments, each of $R^{6a}$ and $R^{6b}$ is hydrogen; and $R^{6c}$ is substituted or unsubstituted alkyl.

In some embodiments, each of $R^{6a}$ and $R^{6b}$ is hydrogen; and $R^{6c}$ is unsubstituted alkyl.

In some embodiments, each of $R^{6a}$ and $R^{6b}$ is hydrogen; and $R^{6c}$ is methyl or ethyl.

In some embodiments, each of $R^{6a}$ and $R^{6b}$ is hydrogen; and $R^{6c}$ is alkyl substituted with amino, alkylamino, or dialkylamino.

In some embodiments, each of $R^{6a}$ and $R^{6b}$ is hydrogen; and $R^{6c}$ is alkyl substituted with dimethylamino.

In some embodiments, each of $R^{6a}$ and $R^{6b}$ is hydrogen; and $R^{6c}$ is —$CH_2NMe_2$.

In some embodiments, $R^{6a}$ and $R^{6b}$ form a bond; and $R^{6c}$ is hydrogen or substituted or unsubstituted alkyl.

In some embodiments, $R^{6a}$ and $R^{6b}$ form a bond; and $R^{6c}$ is methyl.

In some embodiments, the compound is according to Formula (IXa), (IXb), or (IXc)

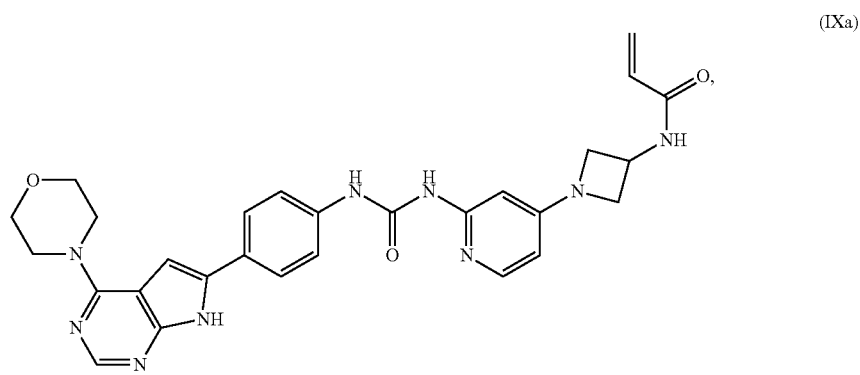

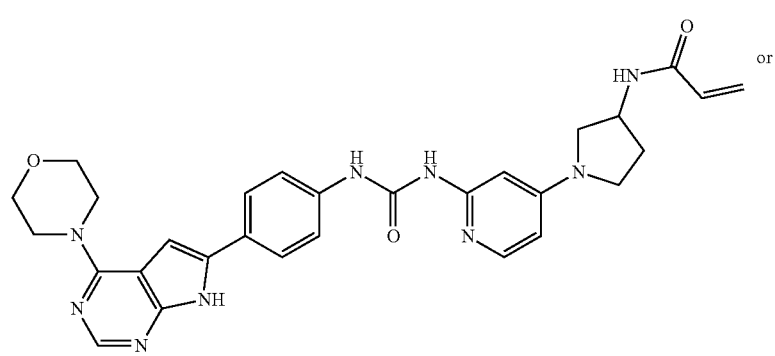
(IXb)
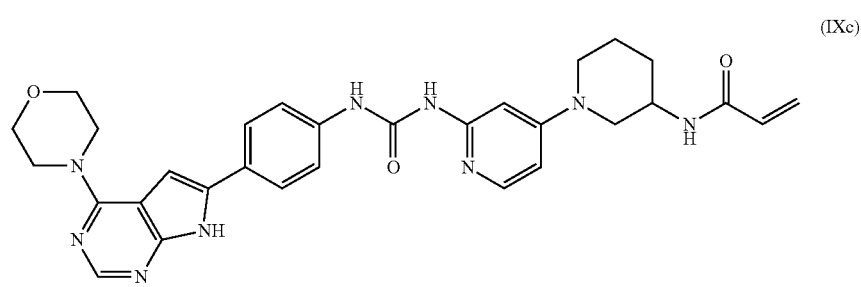
(IXc)
or a pharmaceutically acceptable salt thereof.
In some embodiments, the compound is according to Formula (Xa), (Xb), or (Xc)
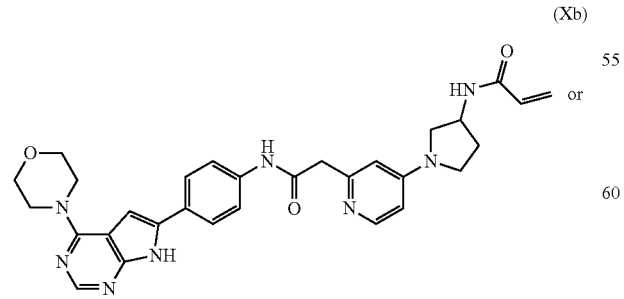
(Xa)
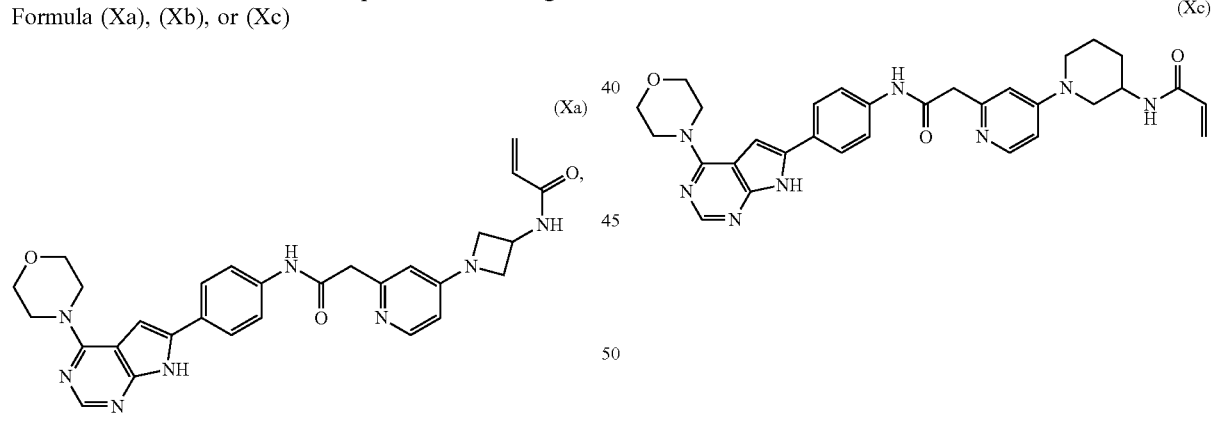
(Xc)
or a pharmaceutically acceptable salt thereof.
In some embodiments, the compound is according to Formula (XIa), (XIb), or (XIc)

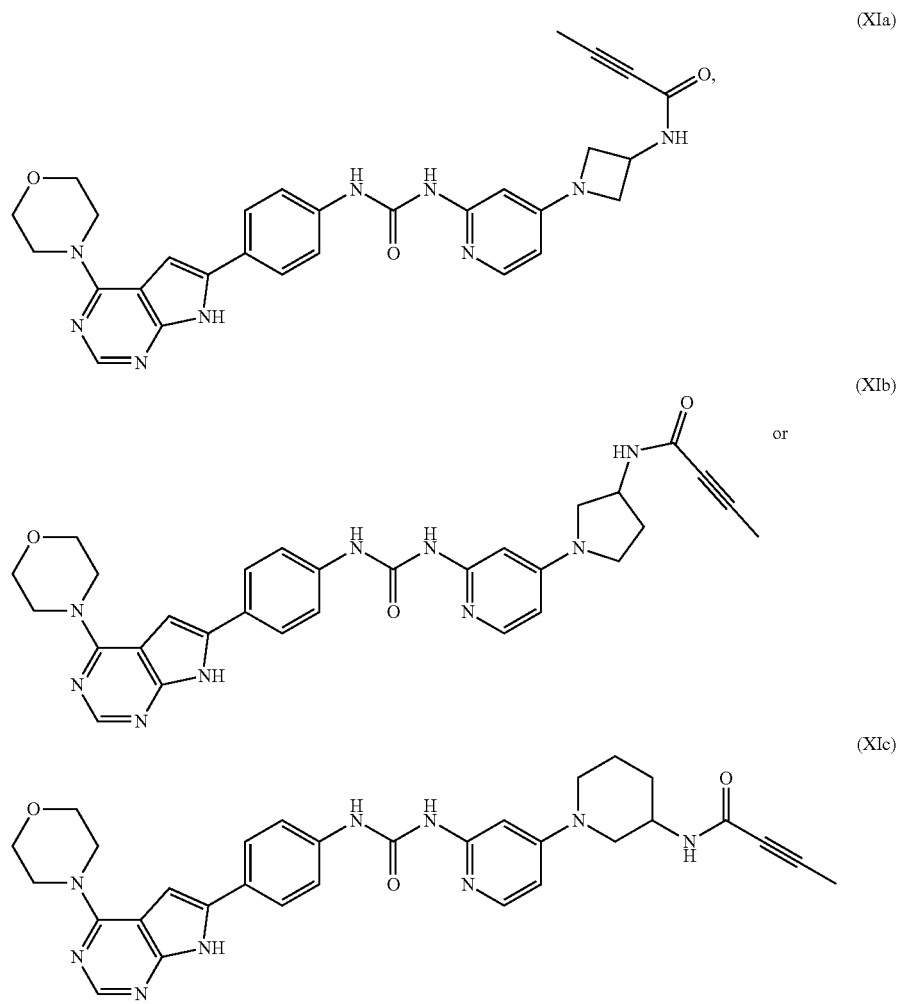
(XIa)
(XIb) or
(XIc)
or a pharmaceutically acceptable salt thereof.
In some embodiments, the compound is according to Formula (XIIa), (XIIb), or (XIIc)
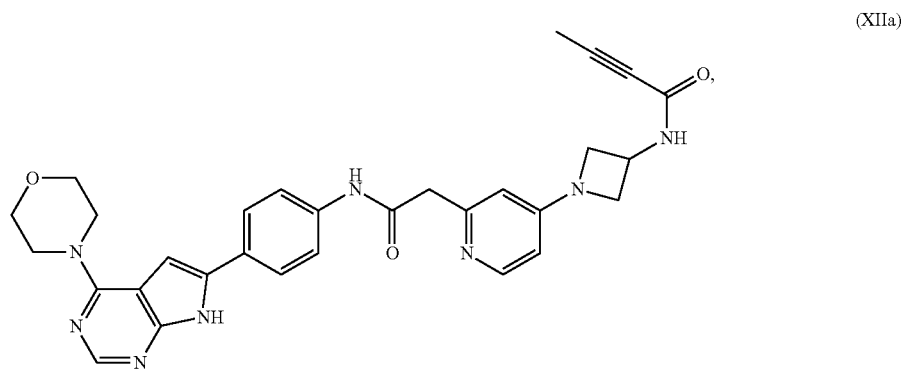
(XIIa)

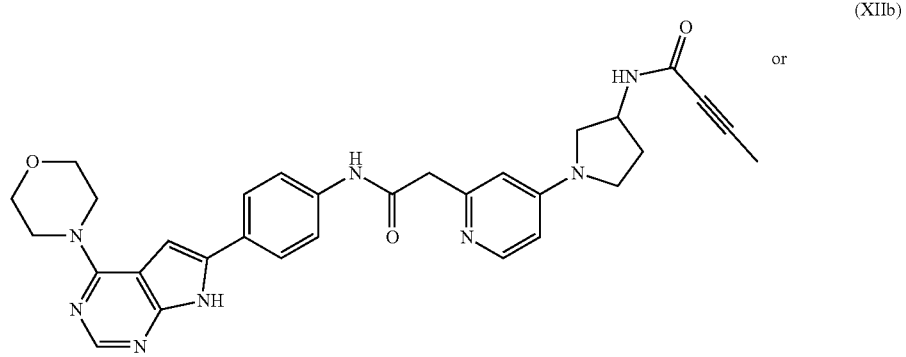
(XIIb)
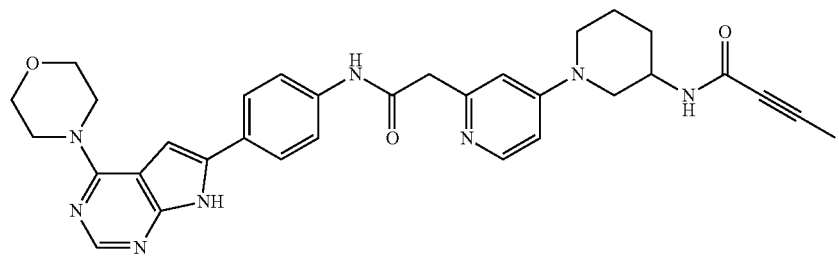
(XIIc)
or a pharmaceutically acceptable salt thereof.
In some embodiments, the compound is according to Formula (XIIIa), (XIIIb), or (XIIIc)
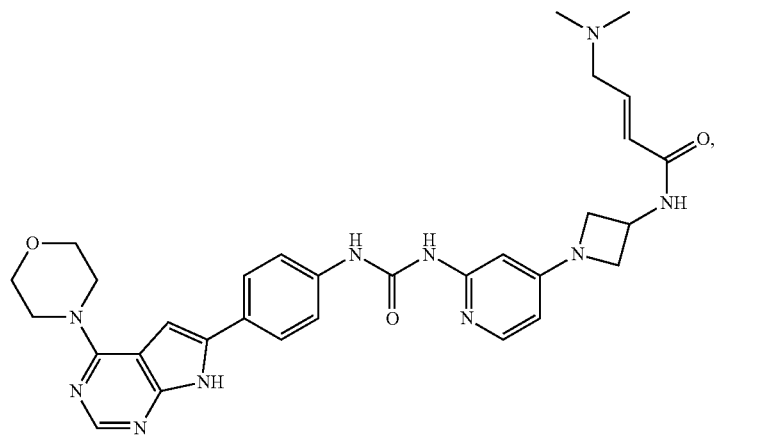
(XIIIa)
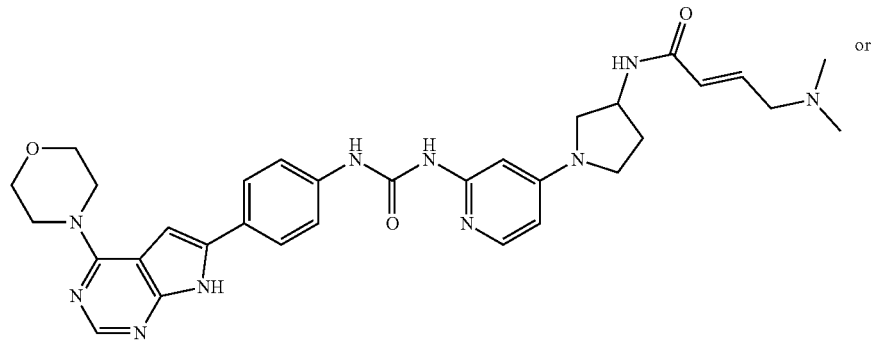
(XIIIb) or (XIIIc)
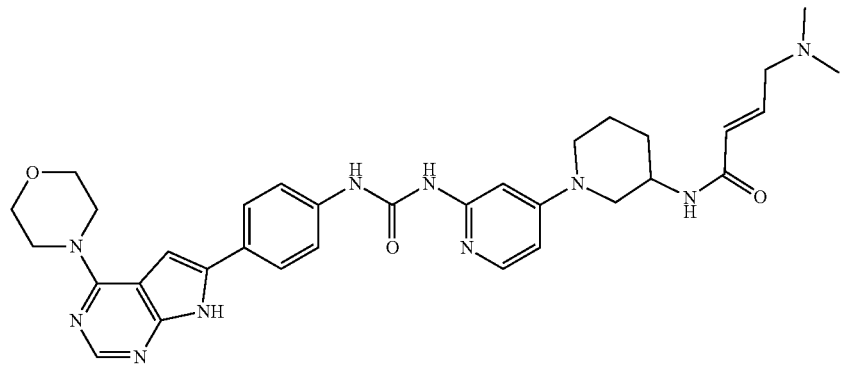
or a pharmaceutically acceptable salt thereof.
In some embodiments, the compound is according to Formula (XIVa), (XIVb), or (XIVc)
(XIVa)
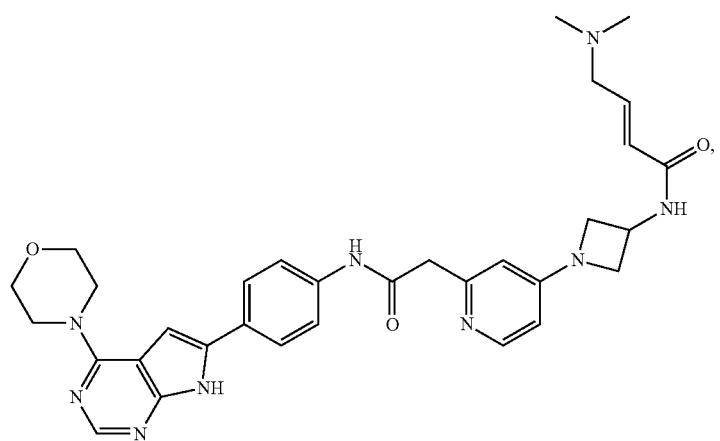
(XIVb)
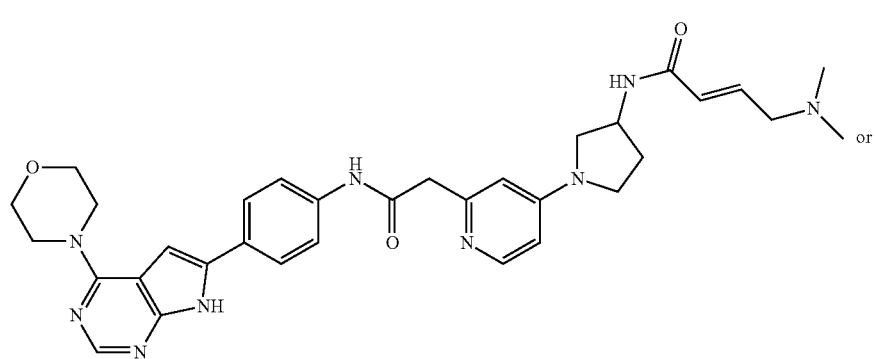

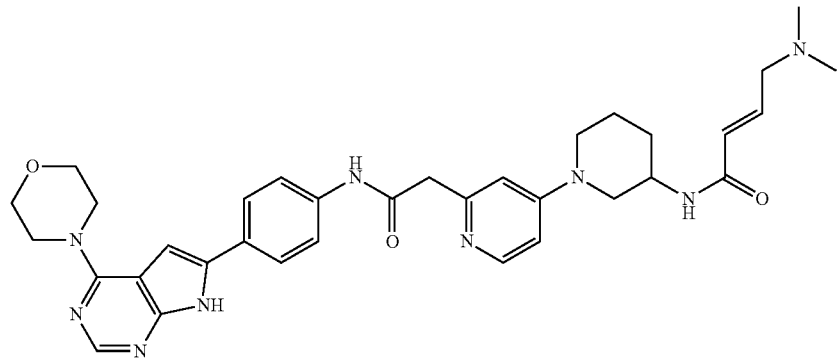
(XIVc)

or a pharmaceutically acceptable salt thereof.

In some embodiments, the compound is according to Formula (XV)

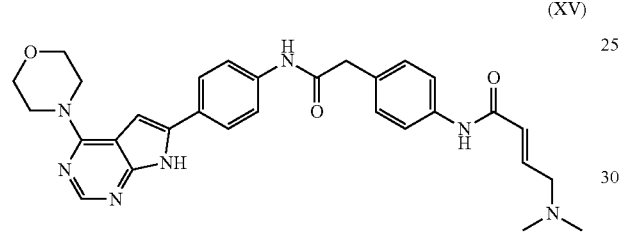
(XV)

or a pharmaceutically acceptable salt thereof.

In some embodiments, the compound is according to Formula (XVI)

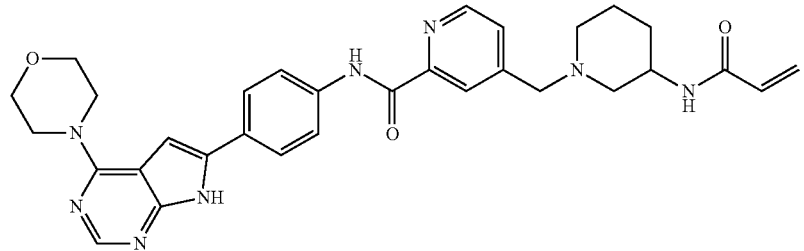
(XVI)

or a pharmaceutically acceptable salt thereof.

In some embodiments, the compound is according to Formula (XVII)

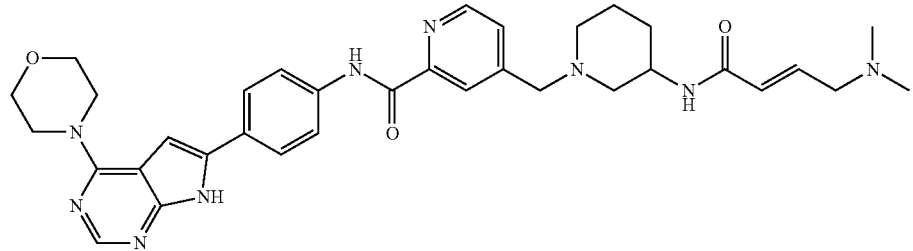
(XVII)

or a pharmaceutically acceptable salt thereof.

In some embodiments, the compound is according to Formula (XXVIIa), (XXVIIb), or (XXVIIc)
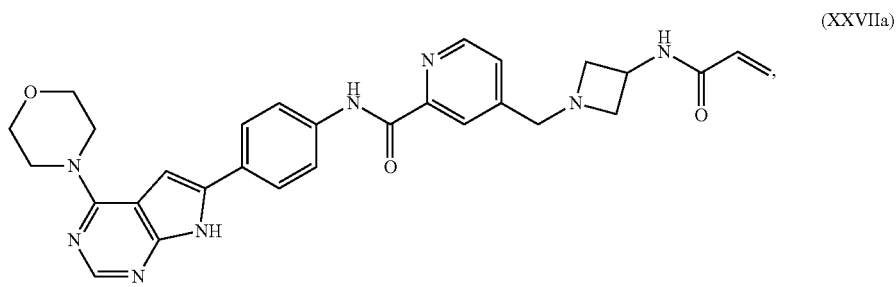
(XXVIIa)
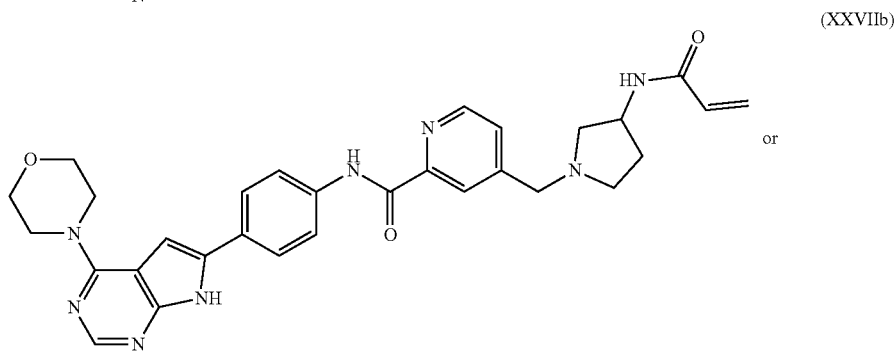
(XXVIIb)
or
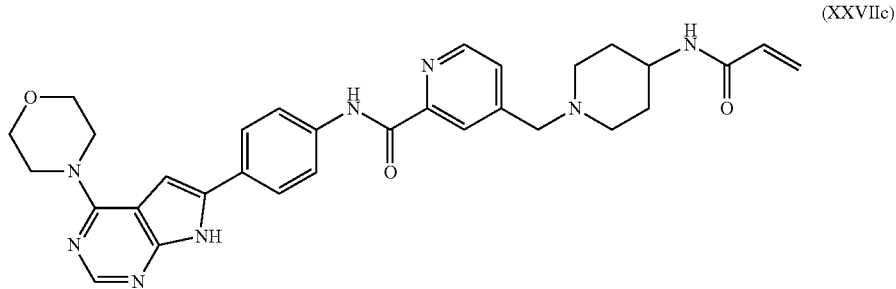
(XXVIIc)
or a pharmaceutically acceptable salt thereof.
In some embodiments, the compound is according to Formula (XXVIIIa), (XXVIIIb), or (XXVIIIc)
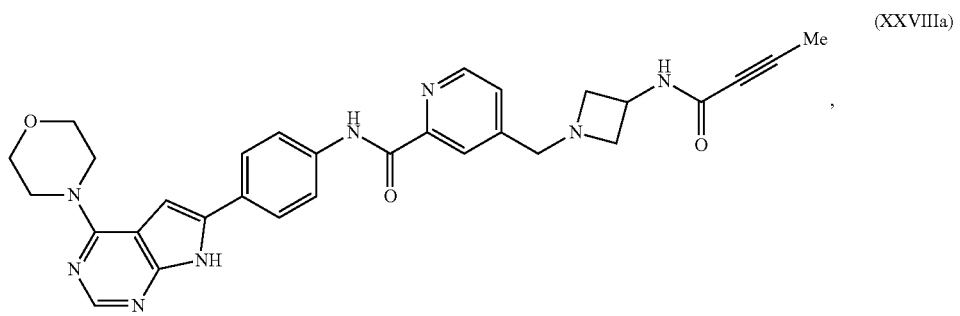
(XXVIIIa)

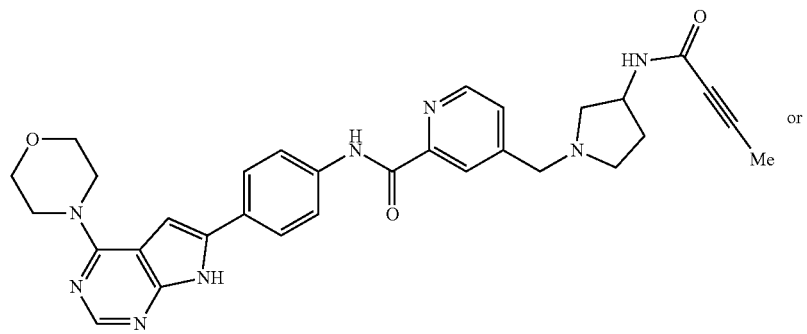
(XXVIIIb)
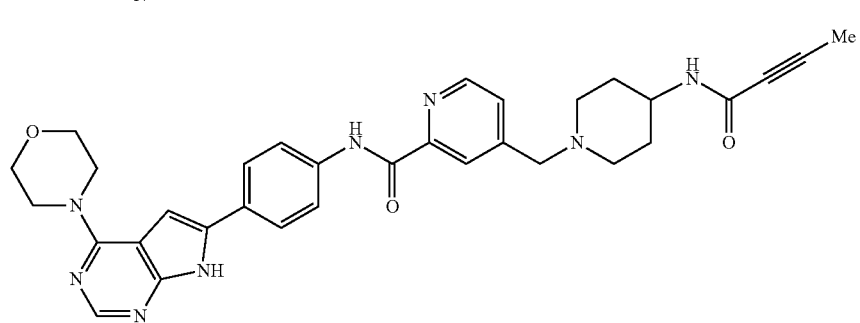
(XXVIIIc)
or a pharmaceutically acceptable salt thereof.
In some embodiments, the compound is according to Formula (XXIXa), (XXIXb), or (XXIXc)
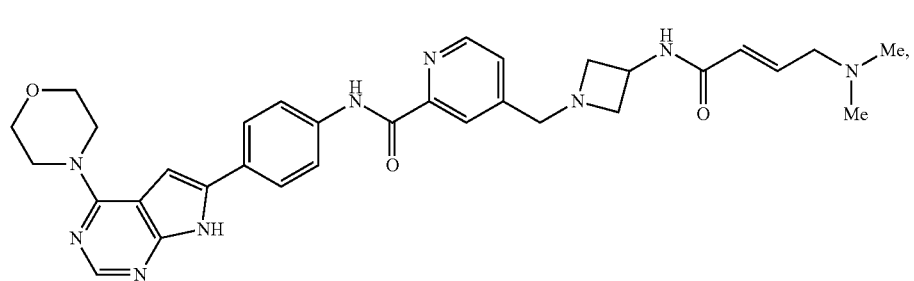
(XXIXa)
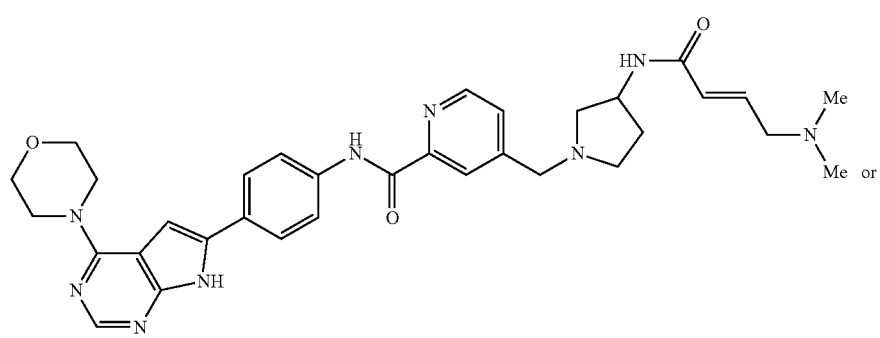
(XXIXb)

-continued

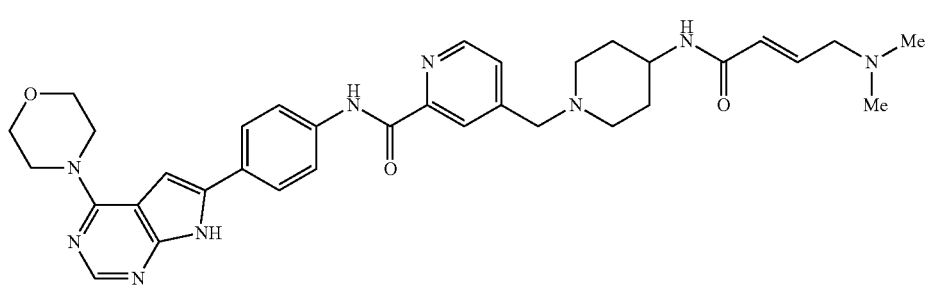

or a pharmaceutically acceptable salt thereof.

In some embodiments, the compound is according to Formula (XLa), (XLb), or (XLc)

In some embodiments, the compound is according to Formula (XLIa), (XLIb), or (XLIc)

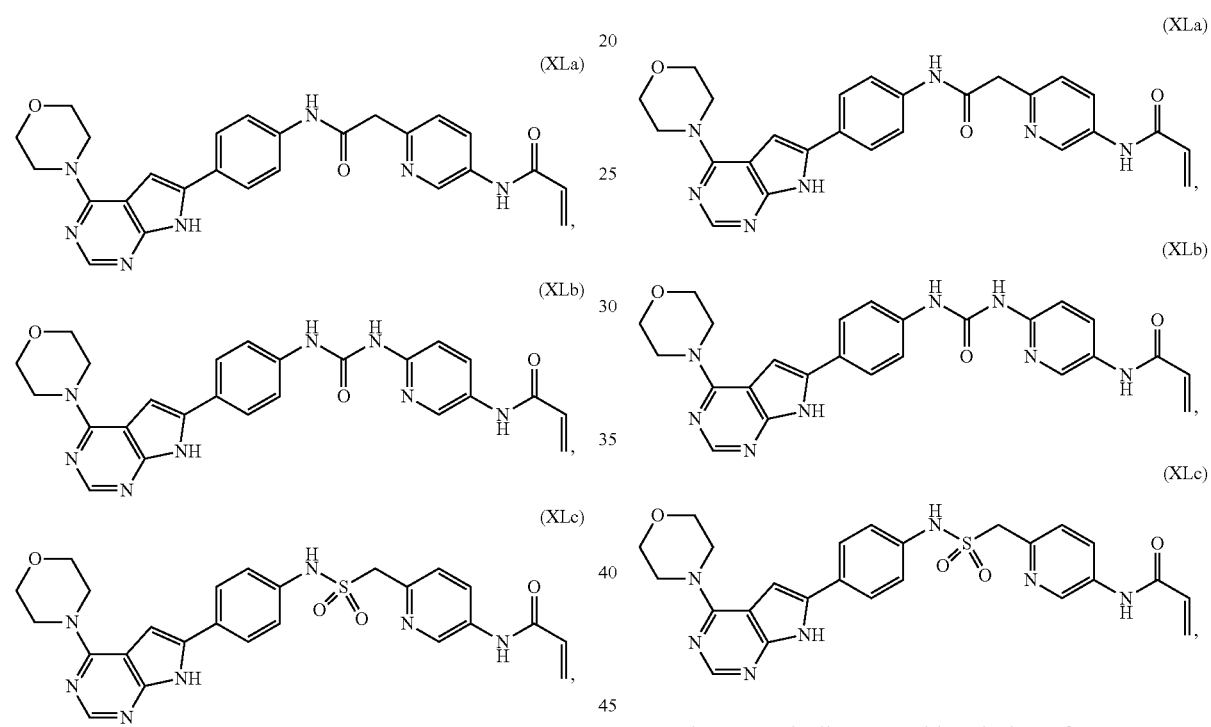

or a pharmaceutically acceptable salt thereof.

or a pharmaceutically acceptable salt thereof.

In some embodiments, the compound is according to Formula (XLIa), (XLIb), or (XLIc)

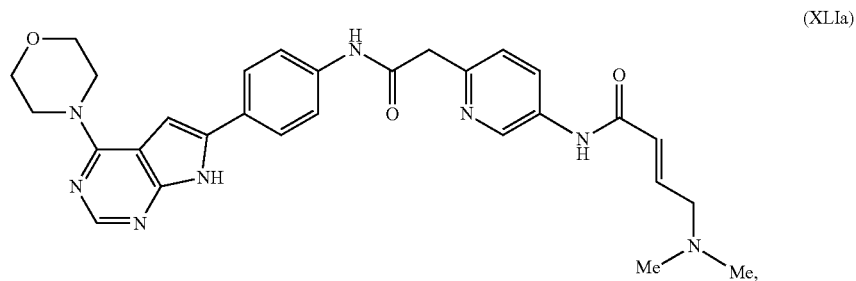

-continued

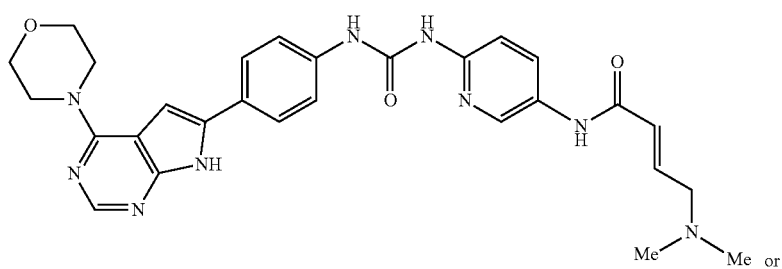
(XLIb)

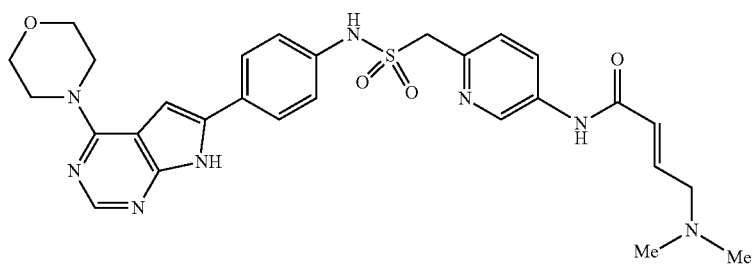
(XLIc)

or a pharmaceutically acceptable salt thereof.

In some embodiments, the compound is according to Formula (XLIIa), (XLIIb), or (XLIIc)

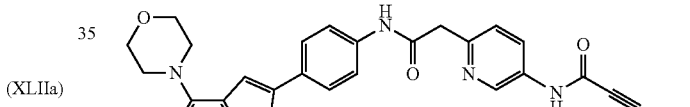
(XLIIa)

(XLIIb)

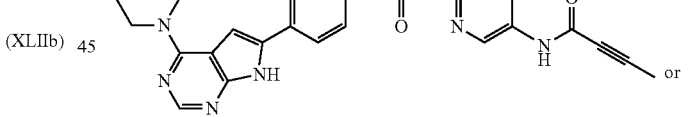
(XLIIc)

or a pharmaceutically acceptable salt thereof.

In some embodiments, the compound is according to Formula (XLIIIa), (XLIIIb), or (XLIIIc)

(XLIIIa)

(XLIIIb)

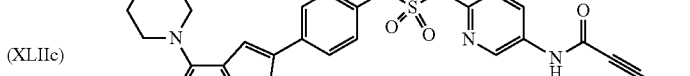
(XLIIIc)

or a pharmaceutically acceptable salt thereof.

In certain embodiments, the compound is selected from Compounds 1-26 and 101-112 provided herein. In certain embodiments, the compound is Compound 10. In certain embodiments, the compound is the racemate of Compound 10

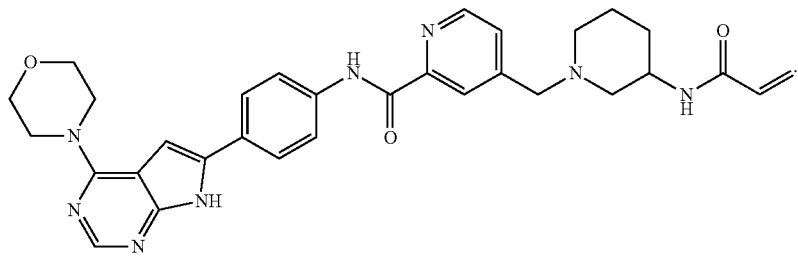

In one particular embodiment, the compound is the (R)-isomer of Compound 10

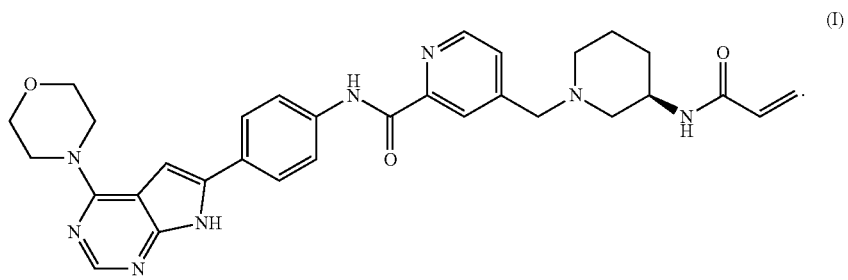 [SMILES: C=CC(=O)N[C@@H]1CCCN(Cc2ccnc(C(=O)Nc3ccc(-c4cc5c(N6CCOCC6)ncnc5[nH]4)cc3)c2)C1]

(I)

In one particular embodiment, the compound is N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide, or a pharmaceutically acceptable salt thereof. In one particular embodiment, the compound is the (S)-isomer of Compound 10

Embodiments of the compounds of Formula (I) displayed improved potency against menin-MLL with $IC_{50}$ values of as low as less than 1 nM or less than 0.1 nM, and/or high occupancy of active site(s) of menin (e.g., more than 50%, 70% or 90% occupancy) at low dosages of below 5 mg/kg (e.g., at or below 3 mg/kg) when administered in vivo (e.g., in rats).

In some embodiments, provided is a pharmaceutical composition comprising a compound according to Formula (I).

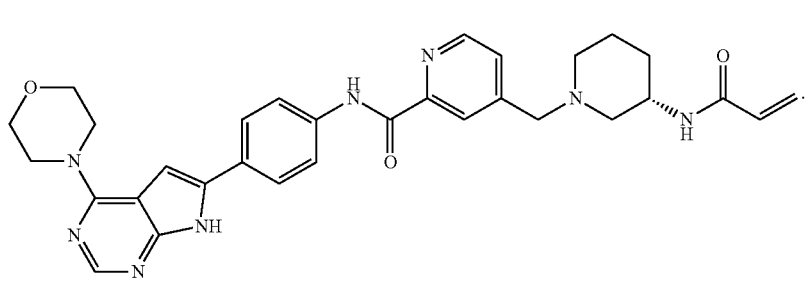

(II)

In one particular embodiment, the compound is N-[4-[4-(4-morpholinyl)-7H-pyrrolo[2,3-d]pyrimidin-6-yl]phenyl]-4-[[3(S)-[(1-oxo-2-propen-1-yl)amino]-1-piperidinyl]methyl]-2-pyridinecarboxamide, or a pharmaceutically acceptable salt thereof.

In some embodiments, the compound is according to Formula (XLIIa).

In some embodiments, the compound is according to Formula (XLIIIa).

In some embodiments, provided is a pharmaceutical composition comprising a therapeutically effective amount of a compound of Formula (I), and a pharmaceutically acceptable excipient.

In certain aspects, provided are methods of treating diabetes, wherein the method comprises administering to a subject in need (e.g., a subject suffering from diabetes mellitus) a composition containing a therapeutically effective amount of one or more Menin-MLL inhibitor compounds described herein.

In a particular embodiment, the menin-MLL inhibitor is Compound 10. In a more particular embodiment, the menin-MLL inhibitor is a (R)-isomer of Compound 10.

In a particular embodiment, the menin-MLL inhibitor is KO-539 or Zifomenib

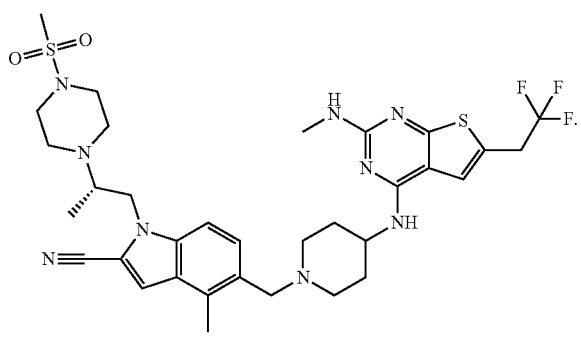 [SMILES: CNc1nc(NC2CCN(Cc3ccc4c(cc(C#N)n4C[C@H](C)N4CCN(S(C)(=O)=O)CC4)c3C)CC2)c2cc(CC(F)(F)F)sc2n1]

In a particular embodiment, the menin-MLL inhibitor is SNDX-5613 or Revumenib

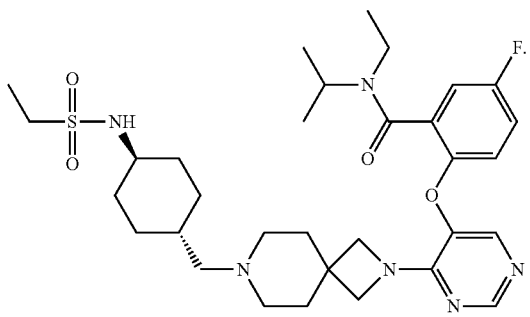 [SMILES: CCN(C(=O)c1cc(F)ccc1Oc1cncnc1N1CC2(CCN(C[C@H]3CC[C@H](NS(=O)(=O)CC)CC3)CC2)C1)C(C)C]

In some embodiments, the pharmaceutical composition is formulated for a route of administration selected from oral administration, parenteral administration, buccal administration, nasal administration, topical administration, or rectal administration.

In some embodiments, provided are methods for treating a diabetic disease or condition comprising administering to a patient in need the pharmaceutical composition(s) described herein. In some embodiments, the disease or condition is type 1 diabetes. In some embodiments, the disease or condition is type 2 diabetes. In some embodiments, the disease or condition is gestational diabetes. In some embodiments, the disease or condition is maturity onset diabetes of the young. In some embodiments, the disease or condition is steroid diabetes. In some embodiments, the disease or condition is double diabetes.

In some embodiments, provided is a pharmaceutical composition comprising a pharmaceutically acceptable carrier and a pharmaceutically effective amount of a compound according to any one of the formulae described herein. In some embodiments, the compound is according to any one of Formulae (I)-(XLIIIc).

In some embodiments, the pharmaceutical composition is formulated for a route of administration selected from oral administration, parenteral administration, buccal administration, nasal administration, topical administration, or rectal administration.

In some embodiments, the carrier is a parenteral carrier.
In some embodiments, the carrier is an oral carrier.
In some embodiments, the carrier is a topical carrier.

Any combination of the groups or embodiments described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further representative embodiments of compounds of Formula (I), include compounds listed in Table 1, or a solvate or a pharmaceutically acceptable salt thereof.

Throughout the specification, chemical groups and substituents thereof can be chosen by one skilled in the field to provide stable chemical moieties and compounds.

In some embodiments, the compounds of Formulae (I)-(XLIIIc) inhibit menin-MLL. In some embodiments, the compounds of Formulae (I)-(XLIIIc) are used to treat patients suffering from menin-MLL-dependent or menin-MLL interaction mediated conditions or diseases, including, but not limited to diabetes mellitus.

In some embodiments, the compounds of Formulae (I)-(XLIIIc) inhibit menin-MLL interaction. In some embodiments, the compounds of Formulae (I)-(XLIIIc) are used to treat patients suffering from menin-MLL interaction-dependent or menin-MLL interaction mediated conditions or diseases, including, but not limited to diabetes mellitus.

Preparation of Compounds

Compounds of any of Formulae (I)-(XLIIIc) may be synthesized using standard synthetic reactions known to those of skill in the art or using methods known in the art. The reactions can be employed in a linear sequence to provide the compounds or they may be used to synthesize fragments which are subsequently joined via methods known in the art.

Described herein are compounds that inhibit the activity of menin-MLL and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite, or pharmaceutically acceptable prodrug of such compound are provided.

The starting material used for the synthesis of the compounds described herein may be synthesized or can be obtained from commercial sources, such as, but not limited to, Aldrich Chemical Co. (Milwaukee, Wisconsin), Bachem (Torrance, California), or Sigma Chemical Co. (St. Louis, Mo.). The compounds described herein, and other related compounds having different substituents can be synthesized using techniques and materials known to those of skill in the art, such as described in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989) (all of which are incorporated by reference in their entirety). Additional methods for the synthesis of compounds described herein may be found in International Patent Application Publication Nos. WO 2020/142559 and WO 2020/142557, Arnold et al. Bioorganic & Medicinal Chemistry Letters 10 (2000) 2167-2170; and Burchat et al. Bioorganic & Medicinal Chemistry Letters 12 (2002) 1687-1690. General methods for the preparation of compounds as disclosed herein may be derived from known reactions in the field, and the reactions may be modified by the use of appropriate reagents and conditions as would be recognized by a person of skill in the art for the introduction of the various chemical moieties found in the formulae provided herein.

The products of the reactions may be isolated and purified, if desired, using conventional techniques, including, but not limited to filtration, distillation, crystallization, chromatography, and the like. Such materials may be characterized using conventional means including physical constants and spectral data.

Compounds described herein may be prepared as a single isomer or a mixture of isomers.

In some embodiments, representative compounds of Formula (I) are prepared according to the synthetic schemes depicted herein.

Further Forms of Compounds

Compounds disclosed herein have a structure of Formulae (I)-(XLIIIc). It is understood that when reference is made to the compounds described herein, it is meant to include compounds of any of Formulae (I)-(XLIIIc) as well as to all of the specific compounds that fall within the scope of these generic formulae, unless otherwise indicated.

Compounds described herein may possess one or more stereocenters and each center may exist in the (R)- or (S)-configuration. Compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diastereomeric mixtures can be separated into their individual diastereomers on the basis of their physical chemical differences by methods known, for example, by chromatography and/or fractional crystallization. In some embodiments, enantiomers can be separated by chiral chromatographic columns. In some embodiments, enantiomers can be separated by converting the enantiomeric mixture into a diastereomeric mixture by reaction with an appropriate optically active compound (e.g., a chiral alcohol or amine), separating the diastereomers and converting (e.g., hydrolyzing) the individual diastereomers to the corresponding pure enantiomers. All such isomers, including diastereomers, enantiomers, and mixtures thereof are considered as part of the compositions described herein.

A compound as disclosed herein may in one aspect be in a purified form and compositions comprising a compound in purified forms are disclosed herein. In certain embodiments, a composition of substantially pure compound means that the composition contains no more than 15%, no more than 10%, no more than 5%, no more than 3%, or no more than 1% impurity. An impurity may be the compound in a stereochemical form different from the desired stereochemical form. For instance, a composition of substantially pure (9-compound means that the composition contains no more than 15%, no more than 10%, no more than 5%, no more than 3%, or no more than 1% of the (R)-form of the compound. Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]−[(S)-compound])/([(R)-compound]+[(S)-compound])×100, where the (R)-compound>(9-compound; or % ee=([(S)-compound]−[(R)-compound])/([(S)-compound]+[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

Methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, compounds described herein can exist in unsolvated as well as solvated forms with pharmaceutically acceptable solvents such as water, ethanol, and the like. Solvated forms of compounds presented herein are also considered to be disclosed herein.

Compounds of any of Formulae (I)-(XLIIIc) in unoxidized form can be prepared from N-oxides of compounds of any of Formulae (I)-(XLIIIc) by treating with a reducing agent, such as, but not limited to sulfur, sulfur dioxide, triphenylphosphine, lithium borohydride, sodium borohydride, phosphorus trichloride, tribromide, or the like in a suitable inert organic solvent, such as, but not limited to acetonitrile, ethanol, aqueous dioxane, or the like at 0° C. to 80° C.

In some embodiments, compounds described herein are prepared as prodrugs. A "prodrug" as used herein refers to an modified agent that is converted into the parent drug in vivo. Prodrugs are often useful because, in some situations, they may be easier to administer than the parent drug. Prodrugs may, for instance, be bioavailable by oral administration whereas the parent is not. The prodrug may also have improved solubility in pharmaceutical compositions over the parent drug. An example, without limitation, of a prodrug would be a compound described herein which is administered as an ester (i.e., the "prodrug") to facilitate transmittal across a cell membrane where water solubility is detrimental to mobility, but which then is metabolically hydrolyzed to the carboxylic acid, the active (parent) entity once inside the cell where water-solubility is beneficial. A further example of a prodrug might be a short peptide (i.e., polyaminoacid) bonded to an acid group where the peptide is metabolized to reveal the active (parent) moiety. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound. To produce a prodrug, a pharmaceutically active (parent) compound is modified such that the active compound will be regenerated upon in vivo administration. The prodrug can be designed to alter the metabolic stability or the transport characteristics of a (parent) drug, to mask side effects or toxicity, to improve the flavor of a (parent) drug, or to alter other characteristics or properties of a (parent) drug. By virtue of the knowledge of pharmacodynamic processes and drug metabolism in vivo held by those of skill in this art, once a pharmaceutically active compound is known, a person of skill in the art can design prodrugs of the compound (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, and/or Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the appended claimed subject matter. In some cases, some of the herein-described compounds may be a prodrug for another derivative or active compound.

Prodrugs may be designed as reversible drug derivatives for use as modifiers to enhance drug transport to site-specific tissues. In some embodiments, the design of a prodrug increases the effective water solubility (See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety).

Sites on the aromatic ring portion of compounds of any of Formulae (I)-(XLIIIc) can be susceptible to various metabolic reactions, therefore incorporation of appropriate substituents on the aromatic ring structures, for example, halogens can reduce, minimize, or eliminate this metabolic pathway.

Compounds described herein include isotopically-labeled compounds, which are identical to those recited in the various formulae and chemical structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, and chlorine such as $^2$H, $^3$H, $^{13}$C, $^{14}$C, $^{15}$N, $^{18}$O, $^{17}$O, $^{35}$S, $^{18}$F, and $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium (i.e., $^2$H) can afford certain therapeutic advantages resulting from greater metabolic stability, for example increased in vivo half-life or reduced dosage requirements.

In certain embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to (1) acid addition salts formed by treating the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, for example, an alkali metal ion (e.g., lithium, sodium, potassium), an alkaline earth ion (e.g., magnesium or calcium), or an aluminum ion; or coordinates with an organic base as a gegenion. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is an alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs can have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms including, but not limited to, amorphous forms, milled forms, and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs, and/or solvates may be accomplished using a variety of techniques including, but not limited to thermal analysis, x-ray diffraction, spectroscopy, vapor sorption, and microscopy. Thermal analysis methods address thermo-chemical degradation or thermo-physical processes including, but not limited to polymorphic transitions and such methods are used to analyze the relationships between polymorphic forms, determine weight loss, find the glass transition temperature, or for excipient compatibility studies. Such methods include, but are not limited to Differential scanning calorimetry (DSC), Modulated Differential Scanning calorimetry (MDCS), Thermogravimetric analysis (TGA), and Thermogravimetric and Infrared analysis (TG/IR). X-ray diffraction methods include, but are not limited to single crystal and powder diffractometers and synchrotron sources. The various spectroscopic techniques used include, but are not limited to Raman, FTIR, UVIS, and NMR (liquid and solid state). The various microscopy techniques include, but are not limited to polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout this specification, groups and chemical substituents thereof can be chosen by one skilled in the field to provide stable chemical moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations that can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each incorporated herein by reference in their entirety.

A pharmaceutical composition, as used herein, refers to a mixture of a compound described herein, such as compounds of any of Formulae (I)-(XLIIIc) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In certain embodiments, the mammal is a human. A therapeutically effective amount can vary widely depending on the severity of the disease, the age and relative health of the subject, the potency of the compound used, and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric, and hydrochloric acids; bases such as sodium hydroxide, lithium hydroxide, potassium hydroxide, and tris-hydroxymethyl-aminomethane; and buffers such as citrate/dextrose, sodium bicarbonate, and ammonium chloride. Such acids, bases, and buffers are included in an amount required to maintain pH of the composition in an acceptable range.

In some embodiments, compositions may also include one or more salts in an amount required to bring osmolality of the composition into an acceptable range. Such salts include those having sodium, potassium, or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite, and ammonium sulfate.

The term "pharmaceutical combination" as used herein, means a product that results from the mixing or combining of more than one active ingredient and includes both fixed and non-fixed combinations of the active ingredients. The term "fixed combination" as used herein means that the active ingredients, for example, a compound described herein and a co-agent, are both administered to a patient simultaneously in the form of a single entity or dosage. The term "non-fixed combination" as used herein means that the active ingredients, for example, a compound described herein and a co-agent, are administered to a patient as separate entities either simultaneously, concurrently, or sequentially with no specific intervening time limits, wherein such administration provides effective levels of the two compounds in the body of the patient. The latter also applies to cocktail therapy, for example, the administration of three or more active ingredients.

The pharmaceutical compositions described herein can be administered to a subject by multiple administration routes including, but not limited to oral, parenteral (e.g., intravenous, subcutaneous, intramuscular), intranasal, buccal, topical, rectal, or transdermal administration routes. The pharmaceutical compositions described herein include, but are not limited to aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as by means of conventional mixing, dissolving, granulating, dragee-making, levigating, emulsifying, encapsulating, entrapping, or compression processes.

The pharmaceutical compositions will include at least one compound described herein, such as a compound of any of Formulae (I)-(XLIIIc) as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also contemplated herein.

"Antifoaming agents" as used herein reduce foaming during processing which can result in coagulation of aqueous dispersions, bubbles in the finished film, or generally impair processing. Exemplary anti-foaming agents include silicon emulsions or sorbitan sesquoleate.

"Antioxidants" as used herein include, for example, butylated hydroxytoluene (BHT), sodium ascorbate, ascorbic acid, sodium metabisulfite, and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

Formulations described herein may benefit from antioxidants, metal chelating agents, thiol containing compounds, and other general stabilizing agents. Examples of such stabilizing agents, include, but are not limited to (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v polysorbate 20, (h) arginine, (i) heparin, (j) dextran sulfate, (k) cyclodextrins, (l) pentosan polysulfate and other heparinoids, (m) divalent cations such as magnesium and zinc, or (n) combinations thereof.

"Binders" as used herein impart cohesive qualities and include, for example, alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; dextrin; a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" as used herein include any commonly used excipients in pharmaceutics and should be selected on the basis of compatibility with the compounds disclosed herein, such as, compounds of any of Formulae (I)-(XLIIIc) and the release profile properties of the desired dosage form. Exemplary carrier materials include, for example, binders, suspending agents, disintegration agents, filling agents, surfactants, solubilizers, stabilizers, lubricants, wetting agents, diluents, and the like. "Pharmaceutically compatible carrier materials" as used herein may include, but are not limited to acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars, sodium stearoyl lactylate, carrageenan, monoglyceride, diglyceride, pregelatinized starch, and the like. See, for example, Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents" and/or "viscosity modulating agents" as used herein include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, for example, hydrophilic polymers, electrolytes, Tween® 60 or 80, polyethylene glycol (PEG), polyvinylpyrrolidone (PVP; commercially known as Plasdone®), and the carbohydrate-based dispersing agents such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108® which are block copolymers of ethylene oxide and propylene oxide); and poloxamines (e.g., Tetronic 908®, also known as Poloxamine 908® which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, for example, the polyethylene glycol can have a molecular weight of about 300 to about 6000, or about 3350 to about 4000, or about 5400 to about 7000, sodium carboxymethylcellulose, methylcellulose, polysorbate-80, sodium alginate, gums such as gum tragacanth and gum acacia, guar gum, xanthans including xanthan gum, sugars, cellulosics, such as, e.g., sodium carboxymethylcellulose, methylcellulose, sodium carboxymethylcellulose, polyethoxylated sorbitan monolaurate, povidone, carbomers, polyvinyl alcohol (PVA), alginates, chitosans, and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol, and isopropyl myristate.

Combinations of one or more erosion facilitator with one or more diffusion facilitator can also be used in the compositions described herein.

The term "diluent" as used herein refers to chemical compounds that are used to dilute the compound of interest prior to delivery. Diluents can also be used to stabilize compounds because they can provide a more stable environment. Salts dissolved in buffered solutions (which also can provide pH control or maintenance) are also utilized as diluents in the art, including, but not limited to a phosphate buffered saline solution. In certain embodiments, diluents increase bulk of the composition to facilitate compression or create sufficient bulk for a homogenous blend for capsule filling. Such compounds include, for example, lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar such as DiPac® (Amstar), mannitol, hydroxypropylmethylcellulose, hydroxypropylmethylcellulose acetate stearate, sucrose-based diluents, confectioner's sugar; monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

The term "disintegrate" as used herein includes both the dissolution and dispersion of the dosage form when contacted with gastrointestinal fluid. "Disintegration agents or disintegrants" as used herein facilitate the breakup or disintegration of a substance. Examples of disintegration agents include a starch, for example, a natural starch such as corn starch or potato starch, a pregelatinized starch such as National 1551 or Amijel®, or sodium starch glycolate such as Promogel® or Explotab®, a cellulose such as a wood product, methylcrystalline cellulose, for example, Avicel®, Avicel® PH101, Avicel® PH102, Avicel® PH105, Elcema® P100, Emcocel®, Vivacel®, Ming Tia®, and SolkaFloc®, methylcellulose, croscarmellose, or a cross-linked cellulose such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, for example, a drug moving from the gastrointestinal tract into the portal vein or lymphatic system.

An "enteric coating" as used herein is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of six to seven, and thus dissolves sufficiently in the small intestine or colon to release the active agent therein.

"Erosion facilitators" as used herein include materials that control the erosion of a particular material in gastrointestinal fluid. Erosion facilitators are generally known to those of ordinary skill in the art. Exemplary erosion facilitators include, for example, hydrophilic polymers, electrolytes, proteins, peptides, and amino acids.

"Filling agents" as used herein include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, acesulfame potassium, talin, sylitol, Swiss cream, tagatose, tangerine, thaumatin, tutti fruitti, vanilla, walnut, watermelon, wild cherry, wintergreen, xylitol, or any combination of these flavoring ingredients, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" as used herein are compounds that prevent, reduce, or inhibit adhesion or friction of materials. Exemplary lubricants include, for example, stearic acid, calcium hydroxide, talc, sodium stearyl fumerate, a hydrocarbon such as mineral oil, hydrogenated vegetable oil such as hydrogenated soybean oil (Sterotex®), higher fatty acids and their alkali-metal and alkaline earth metal salts such as aluminum, calcium, magnesium, zinc, stearic acid, sodium stearates, glycerol, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, glyceryl behenate, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" as used herein describes the blood serum or blood plasma concentration, typically measured in mg, or ng of therapeutic agent per mL, dL, or L of blood serum absorbed into the bloodstream after administration. As used herein, measurable plasma concentrations are typically measured in ng/mL or µg/mL.

"Pharmacodynamics" as used herein refers to the factors which determine the biologic response observed relative to the concentration of drug at a site of action.

"Pharmacokinetics" as used herein refers to the factors which determine the attainment and maintenance of the appropriate concentration of drug at a site of action.

"Plasticizers" as used herein are compounds used to soften the microencapsulation material or film coatings to make them less brittle. Suitable plasticizers include, for example, polyethylene glycols such as PEG 300, PEG 400, PEG 600, PEG 1450, PEG 3350, and PEG 800, stearic acid, propylene glycol, oleic acid, triethyl cellulose, and triacetin. In some embodiments, plasticizers can also function as dispersing agents or wetting agents.

"Solubilizers" as used herein include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide, and the like.

"Stabilizers" as used herein include compounds such as any antioxidation agents, buffers, acids, preservatives, and the like.

"Steady state," as used herein, is when the amount of drug administered is equal to the amount of drug eliminated within one dosing interval resulting in a plateau or constant plasma drug exposure.

"Suspending agents" as used herein include compounds such as polyvinylpyrrolidone, for example, polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, for example, the polyethylene glycol can have a molecular weight of about 300 to about 6000, or about 3350 to about 4000, or about 5400 to about 7000, sodium carboxymethylcellulose, methylcellulose, hydroxypropylmethylcellulose, hydroxymethylcellulose acetate stearate, polysorbate-80, hydroxyethylcellulose, sodium alginate, gums such as gum tragacanth and gum acacia, guar gum, xanthans including xanthan gum, sugars, cellulosics such as sodium carboxymethylcellulose, methylcellulose, sodium carboxymethylcellulose, hydroxypropylmethylcellulose, hydroxyethylcellulose, polyethoxylated sorbitan monolaurate, polyethoxylated sorbitan monolaurate, povidone, and the like.

"Surfactants" include compounds such as sodium lauryl sulfate, sodium docusate, Tween® 60 or 80, triacetin, vitamin E TPGS, sorbitan monooleate, polyoxyethylene polysorbates, polaxomers, bile salts, glyceryl monostearate, copolymers of ethylene oxide and propylene oxide, for example, Pluronic® (BASF), and the like. Some other surfactants include polyoxyethylene fatty acid glycerides and vegetable oils, for example, polyoxyethylene (60) hydrogenated castor oil; and polyoxyethylene alkylethers and alkylphenyl ethers, for example, octoxynol 10 and octoxynol 40. In some embodiments, surfactants may be included to enhance physical stability or for other purposes.

"Viscosity enhancing agents" as used herein include, for example, methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, and combinations thereof.

"Wetting agents" as used herein include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween® 80, vitamin E TPGS, ammonium salts, and the like.

Dosage Forms

The compositions described herein can be formulated for administration to a subject via any conventional means including, but not limited to oral, parenteral (e.g., intravenous, subcutaneous, or intramuscular), buccal, intranasal, rectal or transdermal administration routes. As used herein, the term "subject" is used to mean an animal, for example a mammal, including a human or non-human. The terms "patient" and "subject" herein may be used interchangeably.

The pharmaceutical compositions described herein, which include a compound of any of Formulae (I)-(XLIIIc) can be formulated into any suitable dosage form including, but not limited to, aqueous oral dispersions, liquids, gels, syrups, elixirs, slurries, suspensions, and the like for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents may be added, such as the cross-linked croscarmellose sodium, polyvinylpyrrolidone, agar, alginic acid, or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In some embodiments, the pharmaceutical composition is in the form of a powder. In some embodiments, the pharmaceutical composition is in the form of a tablet including, but not limited to a fast-melt tablet. Additionally, pharmaceutical compositions described herein may be administered as a single capsule or in multiple capsule dosage form. In some embodiments, the pharmaceutical composition is administered in two, or three, or four capsules or tablets.

In some embodiments, solid dosage forms, for example, tablets, effervescent tablets, and capsules, are prepared by mixing particles of a compound of any of Formulae (I)-(XLIIIc) with one or more pharmaceutical excipients to form a bulk blend composition. When referring to these bulk blend compositions as homogeneous, it is meant that the particles of the compound of any of Formulae (I)-(XLIIIc) are dispersed evenly throughout the composition so that the composition may be readily subdivided into equally effective unit dosage forms, such as tablets, pills, and capsules. The individual unit dosages may also include film coatings which disintegrate upon oral ingestion or upon contact with diluent. These formulations can be manufactured by conventional pharmacological techniques.

Conventional pharmacological techniques include, for example, one or a combination of the following methods (1) dry mixing, (2) direct compression, (3) milling, (4) dry or non-aqueous granulation, (5) wet granulation, or (6) fusion. See, for example, Lachman et al., The Theory and Practice of Industrial Pharmacy (1986). Other methods include, for example, spray drying, pan coating, melt granulation, granulation, fluidized bed spray drying or coating (e.g., wurster coating), tangential coating, top spraying, tableting, extruding, and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combinations thereof. In some embodiments, using standard coating procedures such as those described in Remington's Pharmaceutical Sciences, 20th Edition (2000), a film coating is provided around the formulation of the compound of any of Formulae (I)-(XLIIIc). In some embodiments, some or all of the particles of the compound of any of Formulae (I)-(XLIIIc) are coated. In some embodiments, some or all of the particles of the compound of any of Formulae (I)-(XLIIIc), are microencapsulated. In still some embodiments, the particles of the compound of any of Formulae (I)-(XLIIIc) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formulae (I)-(XLIIIc) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to natural starch such as corn starch or potato starch, a pregelatinized starch such as National 1551 or Amijel®, or sodium starch glycolate such as Promogel® or Explotab®, a cellulose such as a wood product, methylcrystalline cellulose, for example, Avicel®, Avicel® PH101, Avicel® PH102, Avicel® PH105, Elcema® P100, Emcocel®, Vivacel®, Ming Tia®, and Solka-Floc®, methylcellulose, croscarmellose or a cross-linked cellulose such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination with starch, and the like.

Binders impart cohesiveness to solid oral dosage form formulations. For powder filled capsule formulation, they aid in plug formation that can be filled into soft or hard shell capsules; and for tablet formulation, they ensure the tablet remaining intact after compression and help assure blend uniformity prior to a compression or fill step. Materials suitable for use as binders in the solid dosage forms described herein include, but are not limited to carboxymethylcellulose, methylcellulose (e.g., Methocel®) hydroxypropylmethylcellulose (e.g., Hypromellose USP Pharmacoat-603, hydroxypropylmethylcellulose acetate stearate (Aqoate HS-LF and HS), hydroxyethyl cellulose, hydroxypropylcellulose (e.g., Klucel®), ethylcellulose (e.g., Ethocel®), microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which can act as moderate binder. Formulators skilled in art can determine the binder level for the formulations, but binder usage levels of up to 70% in tablet formulations is common.

Suitable lubricants or glidants for use in the solid dosage forms described herein include, but are not limited to stearic acid, calcium hydroxide, talc, corn starch, sodium stearyl fumerate, alkali metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to sugars (including lactose, sucrose, and dextrose), polysaccharides (including dextrates and maltodextrin), polyols (including mannitol, xylitol, and sorbitol), cyclodextrins and the like.

The term "non water-soluble diluent" as used herein represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g., Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, for example, Pluronic® (BASF), and the like.

Suitable suspending agents for use in the solid dosage forms described herein include, but are not limited to polyvinylpyrrolidone, for example, polyvinylpyrrolidone K12, polyvinylpyrrolidone K17, polyvinylpyrrolidone K25, or polyvinylpyrrolidone K30, polyethylene glycol, for example, the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums such as gum tragacanth and gum acacia, guar gum, xanthans, including xanthan gum, sugars, cellulosics such as sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, butylated hydroxytoluene (BHT), sodium ascorbate, and tocopherol.

It should be appreciated that there is considerable overlap between additives used in the solid dosage forms described herein. Thus, the above-listed additives should be taken as merely exemplary and not limiting the types of additives that can be included in solid dosage forms described herein. The amounts of such additives can be readily determined by one skilled in the art according to the particular properties desired.

In some embodiments, one or more layers of the pharmaceutical composition are plasticized. Illustratively, a plasticizer is generally a high boiling point solid or liquid. Suitable plasticizers can be added from about 0.01% to about 50% by weight (w/w) of the coating composition. Plasticizers include, but are not limited to diethyl phthalate, citrate esters, polyethylene glycol, glycerol, acetylated glycerides, triacetin, polypropylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In some embodiments, the compressed tablets will include a film surrounding the final compressed tablet. In some embodiments, the film coating can provide a delayed release of the compound of any of Formulae (I)-(XLIIIc) from the formulation. In some embodiments, the film coating aids in patient compliance (e.g., Opadry® coatings or sugar coating). Film coatings including Opadry® typically range from about 1% to about 3% of the tablet weight. In some embodiments, the compressed tablets include one or more excipients.

A capsule may be prepared, for example, by placing the bulk blend of the formulation of the compound of any of Formulae (I)-(XLIIIc) described above inside of a capsule. In some embodiments, the formulations (non-aqueous suspensions and solutions) are placed in a soft gelatin capsule. In some embodiments, the formulations are placed in standard gelatin capsules or non-gelatin capsules such as capsules comprising HPMC. In some embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formulae (I)-(XLIIIc) and one or more excipients are dry blended and compressed into a mass, such as a tablet, having a hardness sufficient to provide a pharmaceutical composition that substantially disintegrates within less than about thirty minutes, less than about thirty-five minutes, less than about forty minutes, less than about forty-five minutes, less than about fifty minutes, less than about fifty-five minutes, or less than about sixty minutes, after oral administration thereby releasing the formulation into the gastrointestinal fluid.

In some embodiments, dosage forms may include microencapsulated formulations. In some embodiments, one or more other compatible materials are present in the microencapsulation material. Exemplary materials include, but are not limited to pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formulae (I)-(XLIIIc) which sufficiently isolate the compound of any of Formulae (I)-(XLIIIc) from other non-compatible excipients. Materials compatible with compounds of any of Formulae (I)-(XLIIIc) are those that delay the release of the compounds of any of Formulae (I)-(XLIIIc) in vivo.

Exemplary microencapsulation materials useful for delaying the release of the formulations including the compounds described herein include, but are not limited to hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D, Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In some embodiments, plasticizers such as polyethylene glycols, for example, PEG 300, PEG 400, PEG 600, PEG 1450, PEG 3350, and PEG 800, stearic acid, propylene glycol, oleic acid, and triacetin are incorporated into the microencapsulation material. In some embodiments, the microencapsulating material useful for delaying the release of the pharmaceutical compositions is from the USP or the National Formulary (NF). In some embodiments, the microencapsulation material is Klucel. In some embodiments, the microencapsulation material is methocel.

Microencapsulated compounds of any of Formulae (I)-(XLIIIc) may be formulated by methods known by one of ordinary skill in the art. Such known methods include, for example, spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, for example, complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In some embodiments, the particles of compounds of any of Formulae (I)-(XLIIIc) are microencapsulated prior to being formulated into one of the above forms. In still some embodiments, some or most of the particles are coated prior to being further formulated by using standard coating procedures, such as those described in Remington's Pharmaceutical Sciences, 20th Edition (2000).

In some embodiments, the solid dosage formulations of the compounds of any of Formulae (I)-(XLIIIc) are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to diethyl phthalate, citrate esters, polyethylene glycol, glycerol, acetylated glycerides, triacetin, polypropylene glycol, triethyl citrate, dibutyl sebacate, stearic acid, stearol, stearate, and castor oil.

In some embodiments, a powder including the formulations with a compound of any of Formulae (I)-(XLIIIc) described herein may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still some embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid, and/or tartaric acid. When salts of the compositions described herein are added to water, the acids and the bases react to liberate carbon dioxide gas, thereby causing "effervescence." Examples of effervescent salts include, for example, the following ingredients sodium bicarbonate or a mixture of sodium bicarbonate and sodium carbonate, citric acid, and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the formulations described herein, which include a compound of Formulae (I)-(XLIIIc) are solid dispersions. Methods of producing such solid dispersions are known in the art and include, but are not limited to, for example, U.S. Pat. Nos. 4,343,789, 5,340,591, 5,456, 923, 5,700,485, 5,723,269, and U.S. Patent Application Publication 2004/0013734 each of which is specifically incorporated herein by reference. In some embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated herein by reference.

The pharmaceutical solid oral dosage forms including formulations described herein which include a compound of any of Formulae (I)-(XLIIIc) can be further formulated to provide a controlled release of the compound of Formulae (I)-(XLIIIc). Controlled release refers to the release of the compound of any of Formulae (I)-(XLIIIc) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms (i.e., as an oral dosage form of a pharmaceutical composition as described herein which utilizes an enteric coating to affect release in the small intestine of the gastrointestinal tract). The enteric coated dosage form may be a compressed or molded or an extruded tablet/mold (coated or uncoated) containing granules, powder, pellets, beads, or particles of the active ingredient and/or other composition components which are themselves coated or uncoated. The enteric coated oral dosage form may also be a capsule (coated or uncoated) containing pellets, beads, or granules of the solid carrier or the composition which are themselves coated or uncoated.

The term "delayed release" as used herein refers to a compound delivery where the release can be accomplished at some generally predictable location in the intestinal tract more distal to that which would have been accomplished if there had been no delayed release alterations. In some embodiments, the method for delay of release is via a coating. Any coatings can be applied to a sufficient thickness such that the entire coating does not dissolve in the gastrointestinal fluids at pH below about five, but does dissolve at pH about five and above. It is expected that any anionic polymer exhibiting a pH-dependent solubility profile can be used as an enteric coating in the methods and compositions described herein to achieve delivery to the lower gastrointestinal tract. In some embodiments, the polymers described herein are anionic carboxylic polymers. In some embodiments, the polymers and compatible mixtures thereof, and some of their properties include, but are not limited to:

Shellac, also called purified lac. Shellac is a refined product obtained from the resinous secretion of an insect. This coating dissolves in media at pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS, and NE (Rohm Pharma) are available as solubilized in organic solvent, aqueous dispersion, or dry powders. The Eudragit series RL, NE, and RS are insoluble in the gastrointestinal tract, but are permeable and are used primarily for colonic targeting. The Eudragit series E dissolve in the stomach. The Eudragit series L, L-30D, and S are insoluble in stomach and dissolve in the intestine;

Cellulose Derivatives. Examples of suitable cellulose derivatives are ethyl cellulose; and reaction mixtures of partial acetate esters of cellulose with phthalic anhydride. The performance can vary based on the degree and type of substitution. Cellulose acetate phthalate (CAP) dissolves at pH>6. Aquateric (FMC) is an aqueous based system and is a spray dried CAP pseudolatex with particles<1 µm. Other components in Aquateric can include pluronics, Tweens®, and acetylated monoglycerides. Other suitable cellulose derivatives include cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, and HP-55F grades are suitable. The performance can vary based on the degree and type of substitution. For example, suitable grades of hydroxypropylmethylcellulose acetate succinate include, but are not limited to AS-LG (LF) which dissolves at pH 5, AS-MG (MF) which dissolves at pH 5.5, and AS-HG (HF) which dissolves at higher pH. These polymers are offered as granules or as fine powders for aqueous dispersions;

Poly Vinyl Acetate Phthalate (PVAP). PVAP dissolves at pH>5 and it is much less permeable to water vapor and gastric fluids.

In some embodiments, the coating can, and usually does, contain a plasticizer and possibly other coating excipients such as colorants, talc, and/or magnesium stearate which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings in lieu of plasticizers to solubilize or disperse the coating material and to improve coating performance and the coated product.

In some embodiments, the formulations described herein, which include a compound of Formulae (I)-(XLIIIc), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formulae (I)-(XLIIIc) may be administered using a variety of pulsatile formulations known in the art. For example, such formulations include, but are not limited to those described in U.S. Pat. Nos. 5,011,692, 5,017,381, 5,229,135, and 5,840,329 each of which is specifically incorporated herein by reference. Other pulsatile release dosage forms suitable for use with the present formulations include, but are not limited to, for example, U.S. Pat. Nos. 4,871,549, 5,260,068, 5,260,069, 5,508,040, 5,567,441, and 5,837,284 all of which are specifically incorporated herein by reference. In some embodiments, the controlled release dosage form is pulsatile release solid oral dosage form including at least two groups of particles (i.e. multiparticulate) each containing the formulation described herein. The first group of particles provides a substantially immediate dose of the compound of any of Formulae (I)-(XLIIIc) upon ingestion by a mammal. The first group of particles can be either uncoated or include a coating and/or sealant. The second group of particles includes coated particles which includes from about 2% to about 75%, from about 2.5% to about 70%, or from about 40% to about 70% by weight of the total dose of the compound of any of Formulae (I)-(XLIIIc) in said formulation in admixture with one or more binders. The coating includes a pharmaceutically acceptable ingredient in an amount sufficient to provide a delay of from about two hours to about seven hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D, Eudragit® L100-55, Eudragit® L100, Eudragit® S100, Eudragit® RD100, Eudragit® E100, Eudragit® L12.5, Eudragit® 512.5, Eudragit® NE30D, and Eudragit® NE 40D®) either alone or blended with cellulose derivatives, for example, ethylcellulose, or non-enteric coatings having variable thickness to provide differential release of the formulation that includes a compound of any of Formulae (I)-(XLIIIc).

Many other types of controlled release systems known to those of ordinary skill in the art are suitable for use with the formulations described herein. Examples of such delivery systems include, for example, polymer-based systems such as polylactic and polyglycolic acid, plyanhydrides, and polycaprolactone; porous matrices, nonpolymer-based systems that are lipids including sterols such as cholesterol, cholesterol esters, and fatty acids, or neutral fats, such as mono-, di- and triglycerides; hydrogel release systems; silastic systems; peptide-based systems; wax coatings, bioerodible dosage forms, compressed tablets using conventional binders, and the like. See, for example, Liberman et al., Pharmaceutical Dosage Forms, 2 Ed., Vol. 1, pp. 209-214 (1990); Singh et al., Encyclopedia of Pharmaceutical Technology, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014, and 6,932,983 each of which is specifically incorporated herein by reference.

In some embodiments, pharmaceutical compositions are provided that include particles of the compounds of any of Formula (I)-(XLIIIc), described herein and at least one dispersing agent or suspending agent for oral administration to a subject. The formulations may be a powder and/or granules for suspension, and upon admixture with water a substantially uniform suspension is obtained.

Liquid formulation dosage forms for oral administration can be aqueous suspensions selected from the group including, but not limited to pharmaceutically acceptable aqueous oral dispersions, emulsions, solutions, elixirs, gels, and syrups. See, for example, Singh et al., Encyclopedia of Pharmaceutical Technology, $2^{nd}$ Ed., pp. 754-757 (2002). In addition to the particles of compounds of Formulae (I)-(XLIIIc), the liquid dosage forms may include additives, such as (a) disintegrating agents; (b) dispersing agents; (c) wetting agents; (d) at least one preservative; (e) viscosity enhancing agents; (f) at least one sweetening agent; and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4-hours. The homogeneity should be determined by a sampling method consistent with regard to determining homogeneity of the entire composition. In some embodiments, an aqueous suspension can be re-suspended into a homogenous suspension by physical agitation lasting less than one minute. In some embodiments, an aqueous suspension can be re-suspended into a homogenous suspension by physical agitation lasting less than forty-five seconds. In yet some embodiments, an aqueous suspension can be re-suspended into a homogenous suspension by physical agitation lasting less than thirty seconds. In still some embodiments, no agitation is necessary to maintain a homogeneous aqueous dispersion.

Examples of disintegrating agents for use in the aqueous suspensions and dispersions include, but are not limited to a starch, for example, a natural starch such as corn starch or potato starch, a pregelatinized starch such as National 1551 or Amijel®, or sodium starch glycolate such as Promogel® or Explotab®; a cellulose such as a wood product, methylcrystalline cellulose, for example, Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as hydroxypropylcellulose and hydroxypropyl cellulose ethers (e.g., HPC, HPC-SL, and HPC-L), hydroxypropyl methylcellulose and hydroxypropyl methylcellulose ethers (e.g., HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108® which are block copolymers of ethylene oxide and propylene oxide); and poloxamines (e.g., Tetronic 908®, also known as Poloxamine 908® which is a tetrafunctional block copolymer derived from sequential addition of propylene oxide and ethylene oxide to ethylenediamine (BASF Corporation, Parsippany, N.J.)). In some embodiments, the dispersing agent is selected from a group not comprising one of the following agents hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g., HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylm-ethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108® which are block copolymers of ethylene oxide and propylene oxide); or poloxamines (e.g., Tetronic 908® also known as Poloxamine 908®).

Wetting agents suitable for the aqueous suspensions and dispersions described herein are known in the art and include, but are not limited to cetyl alcohol, glycerol monostearate, polyoxyethylene sorbitan fatty acid esters (e.g., the commercially available Tweens® such as Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine, and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans, and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, talin, swiss cream, tagatose, tangerine, thaumatin, tutti fruitti, vanilla, walnut, watermelon, wild cherry, wintergreen, xylitol, or any combination of these flavoring ingredients, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In some embodiments, the aqueous liquid dispersion can comprise a sweetening agent or flavoring agent in a concentration ranging from about 0.001% to about 1.0% of the volume of the aqueous dispersion. In some embodiments, the aqueous liquid dispersion can comprise a sweetening agent or flavoring agent in a concentration ranging from about 0.005% to about 0.5% of the volume of the aqueous dispersion. In yet some embodiments, the aqueous liquid dispersion can comprise a sweetening agent or flavoring agent in a concentration ranging from about 0.01% to about 1.0% of the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical compositions described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an potentially unstable or hydrophobic active ingredient. Thus, the SEDDS provide an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563 each of which is specifically incorporated herein by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116, 817, and 6,391,452 each of which is specifically incorporated herein by reference. Formulations that include a compound of any of Formulae (I)-(XLIIIc) which are prepared according to these and other techniques well-known in the art are prepared as solutions in saline employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). In certain embodiments, these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, for example, solutions, suspensions, ointments, or gels. Nasal dosage forms generally contain large amounts of water in addition to the active ingredient. Minor amounts of other ingredients such as pH adjusters, emulsifiers, or dispersing agents, preservatives, surfactants, gelling agents, or buffering and other stabilizing and solubilizing agents may also be present. The nasal dosage form can be isotonic with nasal secretions.

For administration by inhalation, the compounds of any of Formula (I)-(XLIIIc) described herein may be in a form as an aerosol, a mist, or a powder. Pharmaceutical compositions described herein are conveniently delivered in the form of an aerosol spray presentation from pressurized packs or a nebuliser with the use of a suitable propellant, for example, dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, by way of example only, gelatin for use in an inhaler or insufflator may be formulated containing a powder mix of the compound(s) described herein and a suitable powder base such as lactose or starch.

Buccal Formulations

Buccal formulations that include compounds of any of Formulae (I)-(XLIIIc) may be administered using a variety of formulations known in the art. For example, such formulations include, but are not limited to those described in U.S. Pat. Nos. 4,229,447, 4,596,795, 4,755,386, and 5,739,136 each of which is specifically incorporated herein by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formulae (I)-(XLIIIc) is provided essentially throughout. Buccal drug delivery, as will be appreciated by those skilled in the art, avoids the disadvantages encountered with oral drug administration, for example, slow absorption, degradation of the active agent by fluids present in the gastrointestinal tract, and/or first-pass inactivation in the liver. With regard to the bioerodible (hydrolysable) polymeric carrier, it will be appreciated that virtually any such carrier can be used so long as the desired drug release profile is not compromised and the carrier is compatible with the compound of any of Formula (I)-(XLIIIc) and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and copolymers. for example, those known as "carbomers" (e.g., Carbopol® which may be obtained from B.F. Goodrich, is one such polymer). Other components that may also be incorporated into the buccal dosage forms described herein include, but are not limited to disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801, and 6,946,144 each of which is specifically incorporated herein by reference in its entirety.

The transdermal dosage forms described herein may incorporate certain pharmaceutically acceptable excipients which are conventional in the art. In some embodiments, the transdermal formulations described herein include at least three components (1) a formulation of a compound of any of Formulae (I)-(XLIIIc); (2) a penetration enhancer; and (3) an aqueous adjuvant. In addition, transdermal formulations can include additional components such as, but not limited to gelling agents, creams and ointment bases, and the like. In some embodiments, the transdermal formulation can further include a woven or non-woven backing material to enhance absorption and prevent the removal of the transdermal formulation from the skin. In some embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formulae (I)-(XLIIIc). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formulae (I)-(XLIIIc) suitable for intramuscular, subcutaneous, or intravenous injection may include physiologically acceptable sterile aqueous or non-aqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (e.g., propyleneglycol, polyethylene-glycol, glycerol, cremophor, and the like), suitable mixtures thereof, vegetable oils (such as olive oil), and injectable organic esters such as ethyl oleate. Proper fluidity can be maintained, for example, via use of a coating such as lecithin, via maintenance of the required particle size in the case of dispersions, and via use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, for example, in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, for example, with physiologically compatible buffers or excipients. Such excipients are generally known in the art.

Parenteral injections may involve bolus injection or continuous infusion. Formulations for injection may be presented in unit dosage form, for example, in ampoules or in multi-dose containers, with an added preservative. The pharmaceutical composition described herein may be in a form suitable for parenteral injection as sterile suspensions, solutions, or emulsions in oily or aqueous vehicles, and may contain formulatory agents such as suspending, stabilizing, and/or dispersing agents. Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters such as ethyl oleate or triglycerides, or liposomes. Aqueous injection suspensions may contain substances which increase the viscosity of the suspension such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, for example, sterile pyrogen-free water before use.

Formulations

In certain embodiments, delivery systems for pharmaceutical compounds may be employed, such as, for example, liposomes and emulsions. In certain embodiments, compositions provided herein can also include a mucoadhesive polymer selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran.

In some embodiments, the compounds described herein may be administered topically and can be formulated into a variety of topically administrable compositions, such as solutions, suspensions, lotions, gels, pastes, medicated sticks, balms, creams, or ointments. Such pharmaceutical compounds can contain solubilizers, stabilizers, tonicity enhancing agents, buffers, and preservatives.

The compounds described herein may also be formulated in rectal compositions such as enemas, rectal gels, rectal foams, rectal aerosols, suppositories, jelly suppositories, or retention enemas containing conventional suppository bases such as cocoa butter or other glycerides as well as synthetic polymers such as polyvinylpyrrolidone, PEG, and the like. In suppository forms of the compositions, a low-melting wax such as, but not limited to a mixture of fatty acid glycerides optionally in combination with cocoa butter is first melted.

Examples of Methods of Dosing and Treatment Regimens

The compounds described herein can be used in the preparation of medicaments for the inhibition of menin or a homolog thereof, or for the treatment of diseases or conditions that would benefit, at least in part, from inhibition of menin or a homolog thereof. In addition, a method for treating any of the diseases or conditions described herein in a subject in need of such treatment involves administration of pharmaceutical compositions containing at least one compound of any of Formulae (I)-(XLIIIc) described herein or a pharmaceutically acceptable salt, pharmaceutically acceptable N-oxide, pharmaceutically active metabolite, pharmaceutically acceptable prodrug, or pharmaceutically acceptable solvate thereof in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, response to the drugs, and the judgment of the treating physician. It is considered well within the skill of the art for one to determine such therapeutically effective amounts by routine experimentation including, but not limited to a dose escalation clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder, or condition, previous therapy, the patient's health status, response to the drugs, and the judgment of the treating physician.

In the case wherein the patient's condition does not improve, upon the physician's discretion, the compounds may be administered chronically, that is, for an extended period of time, including throughout the duration of the patient's life in order to ameliorate or otherwise control or limit the symptoms of the patient's disease or condition.

In the case wherein the patient's status does improve, upon the physician's discretion, the compounds may be given continuously; alternatively, the dose of drug being administered may be temporarily reduced or temporarily suspended for a certain length of time (i.e., a "drug holiday"). The length of the drug holiday can vary between two days and one year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100% including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition(s) has occurred, a maintenance dose is administered if necessary. Subsequently, the dosage or the frequency of administration, or both, can be reduced as a function of the symptoms to a level at which the improved disease, disorder, or condition is retained. Patients can, however, require intermittent treatment on a long-term basis upon any recurrence of symptoms.

The amount of a given agent that will correspond to such an amount for the improvement(s) described above will vary depending upon factors such as the particular compound, disease, or condition and its severity, the identity (e.g., weight) of the subject or host in need of treatment, but can nevertheless be routinely determined in a manner known in the art according to the particular circumstances surrounding the case including, for example, the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example, as two, three, four, or more sub-doses per day.

The pharmaceutical composition described herein may be in unit dosage forms suitable for single administration of precise dosages. In unit dosage form, the formulation is divided into unit doses containing appropriate quantities of one or more compound described herein. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used in which case it is typical to include a preservative in the composition. By way of example only, formulations for parenteral injection may be presented in unit dosage form which include, but are not limited to ampoules or in multi-dose containers with an added preservative.

The foregoing ranges are merely suggestive, as the number of variables in regard to an individual treatment regime is large, and considerable excursions from these recommended values are common. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals including, but not limited to the determination of the $LD_{50}$ (i.e., the dose lethal to 50% of the population) and the $ED_{50}$ (i.e., the dose therapeutically effective in 50% of the population). The dose ratio between the toxic and therapeutic effects is known as the therapeutic index and it can be expressed as the ratio between $LD_{50}$ and $ED_{50}$. Compounds exhibiting high therapeutic indices are recommended. The data obtained from cell culture assays and animal studies can be used in formulating a range of dosages for use in humans. The dosage of such compounds herein lies within a range of circulating concentrations that include the $ED_{50}$ with minimal toxicity. The dosage may vary within this range depending upon the dosage form employed and the route of administration utilized.

Combination Treatments

The Menin-MLL inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition is well within the knowledge of the skilled clinician. The initial administration can be made according to established protocols known in the art, and then, based upon the observed effects, the dosage, modes of administration, and times of the administration can be modified by the skilled clinician.

In certain instances, it may be appropriate to administer at least one Menin-MLL inhibitor compound described herein in combination with another therapeutic agent. By way of example only, if one of the side effects experienced by a patient upon receiving one of the Menin-MLL inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent (e.g., those described herein), the overall therapeutic benefit to the patient is enhanced). Or, by way of example only, the benefit experienced by a patient may be increased by administering one of the compounds described herein with another therapeutic agent, which also includes a therapeutic regimen, that also has therapeutic benefit. In any case, regardless of the disease, disorder, or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously, or within the same treatment protocol) or sequentially, depending upon the nature of the disease, disorder, or condition, the condition of the patient, and the actual choice of compounds used. The determination of the order of administration and the number of repetitions of administration of each therapeutic agent during a treatment protocol is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing (i.e., providing more frequent, lower doses in order to minimize toxic side effects) has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated, and so forth. In addition, when co-administered with one or more biologically active agents, the compound(s) provided herein may be administered either simultaneously with the biologically active agent(s), or sequentially. If administered sequentially, the attending physician will decide on the appropriate sequence of administering, for example, protein in combination with the biologically active agent(s).

In any case, the multiple therapeutic agents (e.g., one of which is a compound of Formulae (I)-(XLIIIc) described herein) may be administered in any order or even simultaneously. If simultaneously, the multiple therapeutic agents may be provided in a single, unified form or in multiple forms (e.g., either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions, and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially with either therapeutic compound being administered by a regimen calling for a two-step administration. The two-step administration regimen may call for sequential administration of the active agents or spaced-apart administration of the separate active agents. The time period between the multiple administration steps may range from a few minutes to several hours depending upon the properties of each pharmaceutical agent such as potency, solubility, bioavailability, plasma half-life, and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during, or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first forty-eight hours of the onset of the symptoms, within the first six hours of the onset of the symptoms, or within three hours of the onset of the symptoms. The initial administration can be via any route practical such as an intravenous injection, a bolus injection, infusion over five minutes to about five hours, a pill, a capsule, transdermal patch, buccal delivery, and the like, or combinations thereof. A compound should be administered as soon as practicable after the onset of a disease or condition is detected or suspected, and for a length of time necessary for the treatment of the disease, such as from about one month to about three months. The length of treatment can vary for each subject, and the length can be determined using known criteria. For example, the compound or a formulation containing the compound can be administered for at least two weeks, between about one month to about five years, or from about one month to about three years.

Exemplary Therapeutic Agents for Use in Combination with an Menin-MLL inhibitor Compound Described Herein Where the subject is suffering from or at risk of suffering from a diabetic disease, an Menin-MLL inhibitor compound can be used with one or more of the following therapeutic agents in any combination insulin, insulin lispro, Humalog, insulin aspart, novolog, insulin glulisine, apidra, regular insulin (Humulin R, Novolin R), prompt insulin zinc (Semilente), isophane insulin, neutral protamine Hagedorn (NPH) (Humulin N, Novolin N), Insulin zinc (Lente), extended insulin zinc insulin (Ultralente), insulin glargine (Lantus), insulin detemir (Levemir), and insulin degludec (Tresiba); biguanides, metformin (Glucophage) phenformin, buformin; thiazolidinediones, rosiglitazone (Avandia), pioglitazone (Actos), and troglitazone (Rezulin): lyn kinase activators; sulfonylureas, tolbutamide, acetohexamide, tolazamide, chlorpropamide, glipizide, glyburide or glibenclamide, glimepiride, gliclazide, glyclopyramide, and gliquidone; meglitinides, repaglinide, nateglinide; alpha-glucosidase inhibitors, miglitol, acarbose, and voglibose; glucagon-like peptide (GLP) agonists, exenatide (Exendin-4, Byetta), liraglutide (Victoza), taspoglutide, lixisenatide (Lyxumia), semaglutide (Ozempic), and dulaglutide (Trulicity); dipeptidyl peptidase-4 (DPP-4) inhibitors vildagliptin (Galvus), sitagliptin (Januvia), saxagliptin (Onglyza). linagliptin (Tradjenta), alogliptin, septagliptin, tenegliptin, gemigliptin, Zemiglo; and SGLT-2 inhibitors, dapagliflozin, canagliflozin, empagliflozin, and remogliflozin.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, for example, U.S. Pat. Nos. 5,323,907, 5,052, 558, and 5,033,252. Examples of pharmaceutical packaging materials include, but are not limited to blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of menin or in which menin is a mediator or contributor to the symptoms or cause.

For example, the container(s) can include one or more compounds described herein, optionally in a composition or in combination with another agent as disclosed herein. The container(s) optionally have a sterile access port (e.g., the container can be an intravenous solution bag or a vial having a stopper pierceable by a hypodermic injection needle). Such kits optionally comprise a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to buffers, diluents, filters, needles, syringes, carrier, package, container, vial, and/or tube labels listing contents and/or instructions for use and package inserts with instructions for use. A set of instructions will also typically be included.

A label can be on or associated with the container. A label can be on a container when letters, numbers, or other characters forming the label are attached, molded, or etched into the container itself. A label can be associated with a container when it is present within a receptacle or carrier that also holds the container, for example, as a package insert. A label can be used to indicate that the contents are to be used for a specific therapeutic application. The label can also indicate directions for use of the contents such as in the methods described herein.

In certain embodiments, the pharmaceutical compositions can be presented in a pack or dispenser device which can contain one or more unit dosage forms containing a compound provided herein. The pack can, for example, contain metal or plastic foil such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals which notice is reflective of approval by the agency of the form of the drug for human or veterinary administration. Such notice, for example, can be the labeling approved by the U.S. Food and Drug Administration for prescription drugs or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or internet address, it is understood that such identifiers can change and the particular information on the internet can come and go, but equivalent information can be found by searching the internet. Reference thereto evidences the availability and public dissemination of such information.

Compounds described herein have been or can be prepared according to the synthetic methods, or some variations thereof, described in U.S. Pat. No. 11,084,825 or WO 2022/133064, the contents of which are hereby incorporated herein by reference in their entireties.

Additional Exemplary Compounds

Other compounds described herein have been or can be prepared according to the synthetic methods, or some variations thereof, described herein. The compounds can be prepared from readily available starting materials using the following general methods and procedures. It will be appreciated that where typical or recommended process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The following compounds were prepared or can be prepared from readily available starting materials using the general methods and procedures described herein and are depicted in Table 1.

TABLE 1

Representative Compounds

| Compound ID | Structure | MW |
|---|---|---|
| 1 | 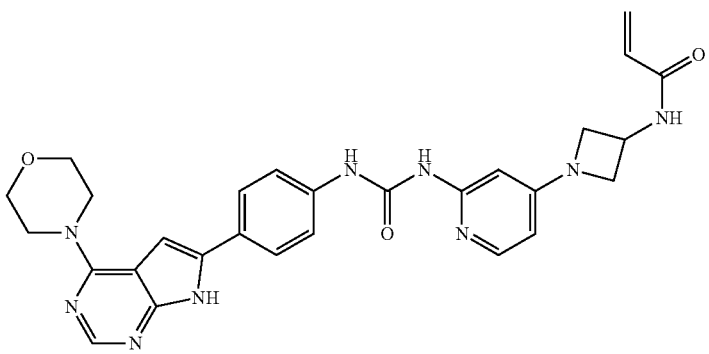 [SMILES: C=CC(=O)NC1CN(c2ccnc(NC(=O)Nc3ccc(-c4cc5c(N6CCOCC6)ncnc5[nH]4)cc3)c2)C1] | 539.59 |

TABLE 1-continued

Representative Compounds

| Compound ID | Structure | MW |
|---|---|---|
| 2 | 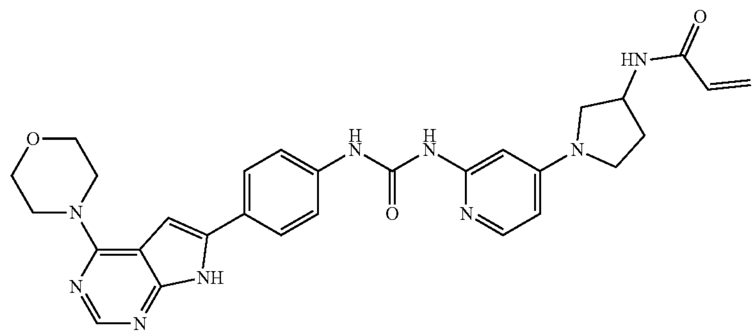 [SMILES: C=CC(=O)NC1CCN(c2ccnc(NC(=O)Nc3ccc(-c4cc5c(N6CCOCC6)ncnc5[nH]4)cc3)c2)C1] | 553.63 |
| 3 | 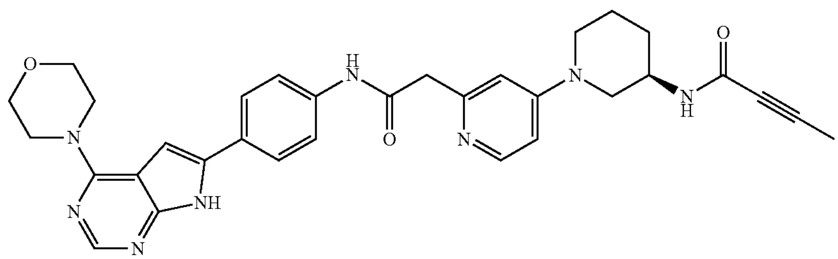 [SMILES: CC#CC(=O)N[C@@H]1CCCN(c2ccnc(CC(=O)Nc3ccc(-c4cc5c(N6CCOCC6)ncnc5[nH]4)cc3)c2)C1] | 578.66 |
| 4 | 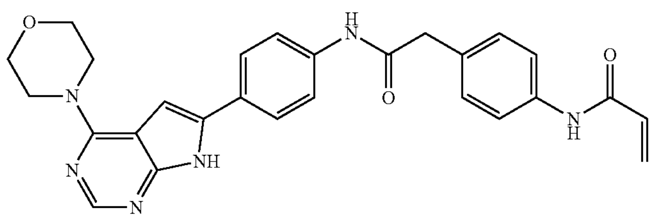 [SMILES: C=CC(=O)Nc1ccc(CC(=O)Nc2ccc(-c3cc4c(N5CCOCC5)ncnc4[nH]3)cc2)cc1] | 482.53 |
| 5 | 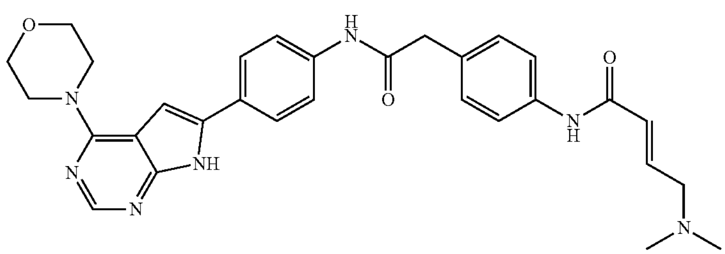 [SMILES: CN(C)C/C=C/C(=O)Nc1ccc(CC(=O)Nc2ccc(-c3cc4c(N5CCOCC5)ncnc4[nH]3)cc2)cc1] | 539.63 |
| 6 | 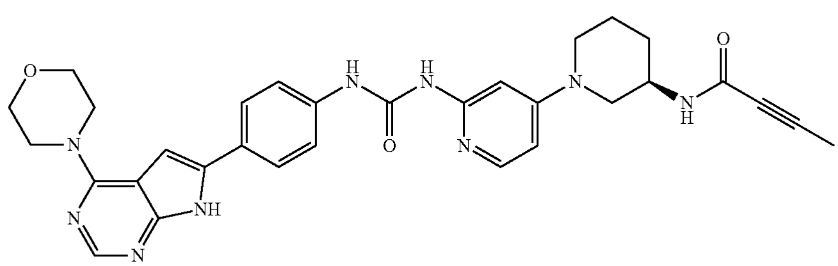 [SMILES: CC#CC(=O)N[C@@H]1CCCN(c2ccnc(NC(=O)Nc3ccc(-c4cc5c(N6CCOCC6)ncnc5[nH]4)cc3)c2)C1] | 579.65 |

TABLE 1-continued

Representative Compounds

| Compound ID | Structure | MW |
|---|---|---|
| 7 | 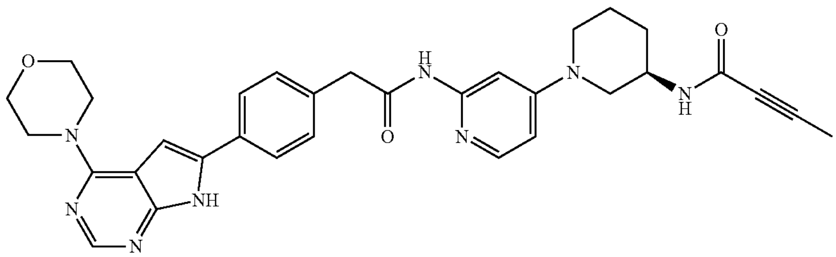 [SMILES: CC#CC(=O)N[C@@H]1CCCN(c2ccnc(NC(=O)Cc3ccc(-c4cc5c(N6CCOCC6)ncnc5[nH]4)cc3)c2)C1] | 578.66 |
| 8 | 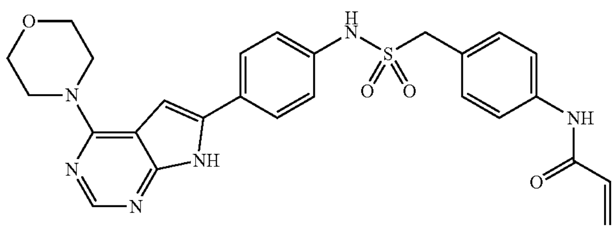 [SMILES: C=CC(=O)Nc1ccc(CS(=O)(=O)Nc2ccc(-c3cc4c(N5CCOCC5)ncnc4[nH]3)cc2)cc1] | 518.59 |
| 9 | 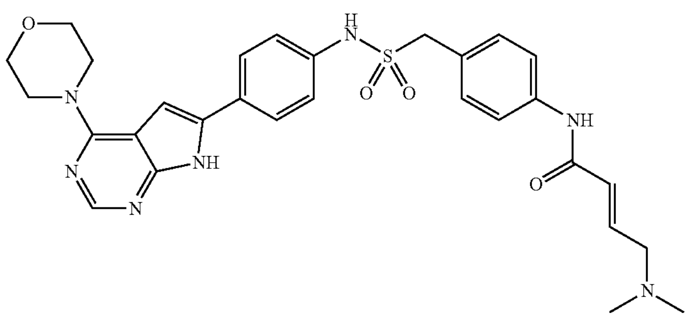 [SMILES: CN(C)C/C=C/C(=O)Nc1ccc(CS(=O)(=O)Nc2ccc(-c3cc4c(N5CCOCC5)ncnc4[nH]3)cc2)cc1] | 575.68 |
| 10 | Compound 10 | 566.67 |
| 11 | 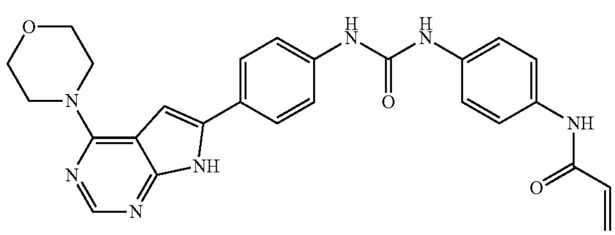 [SMILES: C=CC(=O)Nc1ccc(NC(=O)Nc2ccc(-c3cc4c(N5CCOCC5)ncnc4[nH]3)cc2)cc1] | 483.52 |

TABLE 1-continued

Representative Compounds

| Compound ID | Structure | MW |
|---|---|---|
| 12 | 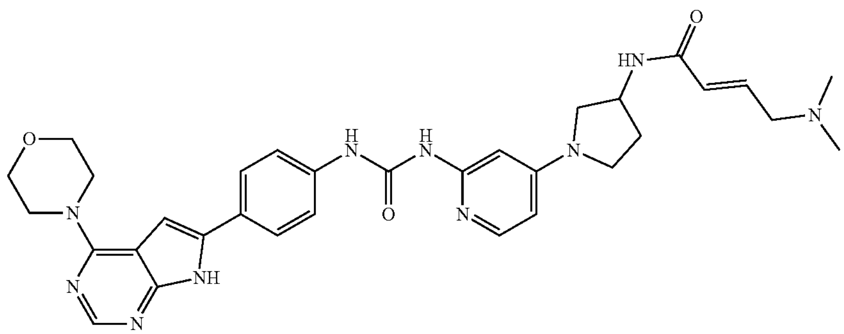 [SMILES: CN(C)C/C=C/C(=O)NC1CCN(c2ccnc(NC(=O)Nc3ccc(-c4cc5c(N6CCOCC6)ncnc5[nH]4)cc3)c2)C1] | 610.72 |
| 13 | 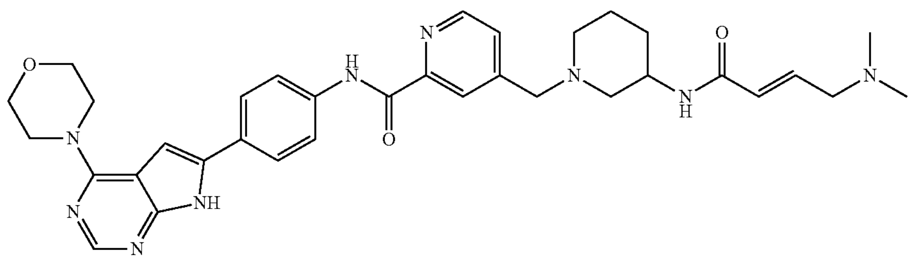 [SMILES: CN(C)C/C=C/C(=O)NC1CCCN(Cc2ccnc(C(=O)Nc3ccc(-c4cc5c(N6CCOCC6)ncnc5[nH]4)cc3)c2)C1] | 623.76 |
| 14 | 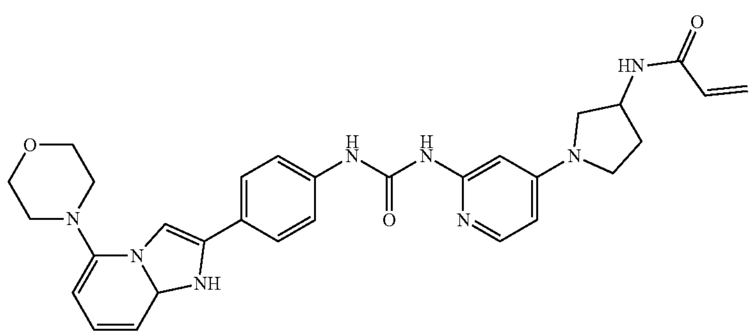 [SMILES: C=CC(=O)NC1CCN(c2ccnc(NC(=O)Nc3ccc(C4=CN5C(N6CCOCC6)=CC=CC5N4)cc3)c2)C1] | 554.65 |
| 15 | 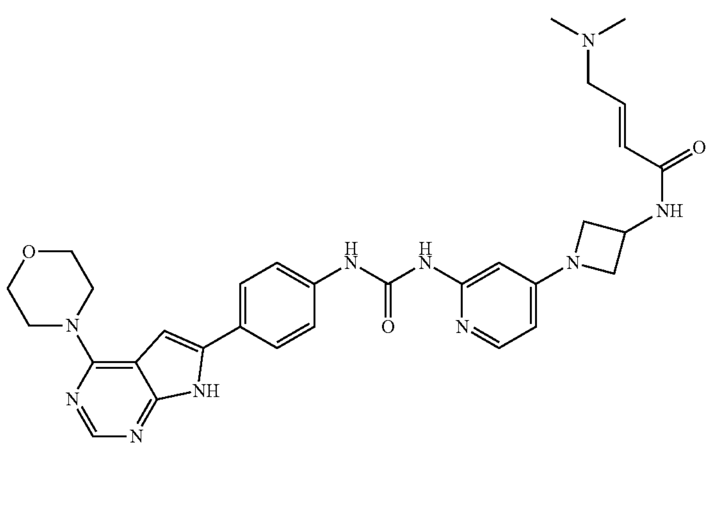 [SMILES: CN(C)C/C=C/C(=O)NC1CN(c2ccnc(NC(=O)Nc3ccc(-c4cc5c(N6CCOCC6)ncnc5[nH]4)cc3)c2)C1] | 596.70 |

TABLE 1-continued

Representative Compounds

| Compound ID | Structure | MW |
|---|---|---|
| 16 | 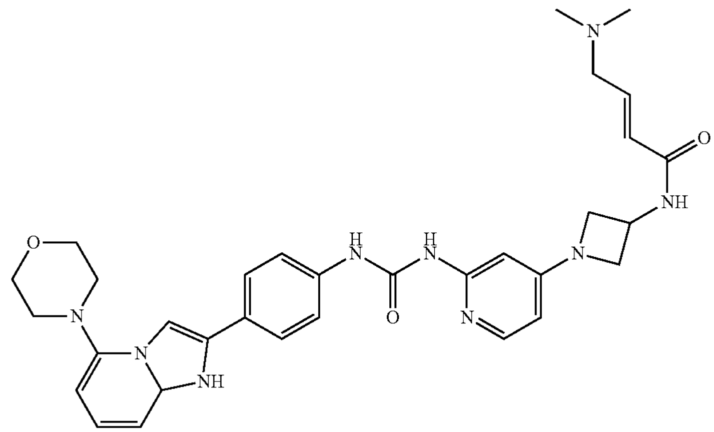 [SMILES: CN(C)C/C=C/C(=O)NC1CN(c2ccnc(NC(=O)Nc3ccc(C4=CN5C(N6CCOCC6)=CC=CC5N4)cc3)c2)C1] | 597.72 |
| 17 | 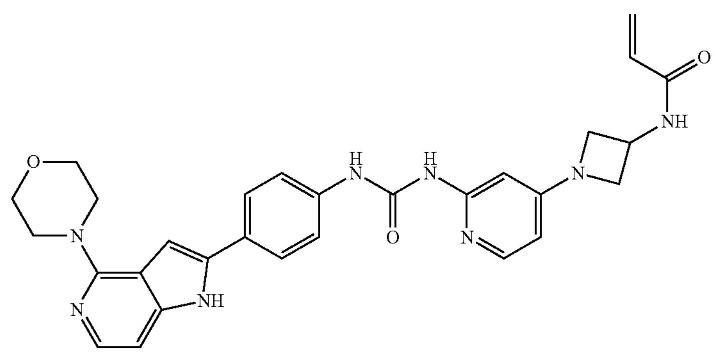 [SMILES: C=CC(=O)NC1CN(c2ccnc(NC(=O)Nc3ccc(-c4cc5c(N6CCOCC6)nccc5[nH]4)cc3)c2)C1] | 538.61 |
| 18 | 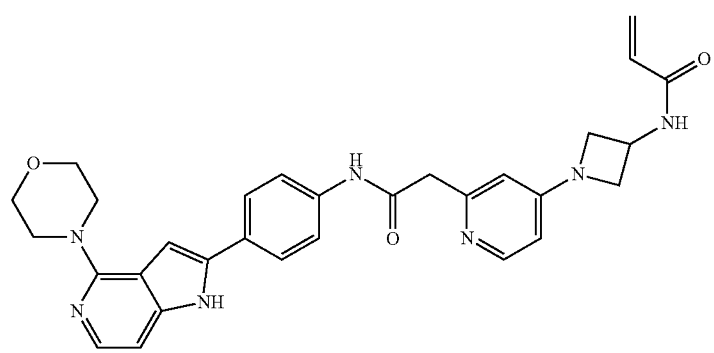 [SMILES: C=CC(=O)NC1CN(c2ccnc(CC(=O)Nc3ccc(-c4cc5c(N6CCOCC6)nccc5[nH]4)cc3)c2)C1] | 537.61 |
| 19 | 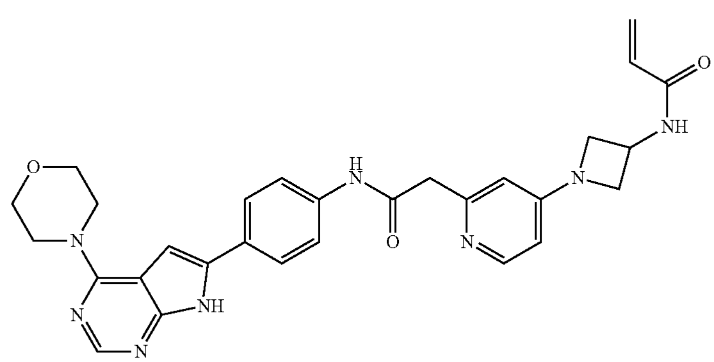 [SMILES: C=CC(=O)NC1CN(c2ccnc(CC(=O)Nc3ccc(-c4cc5c(N6CCOCC6)ncnc5[nH]4)cc3)c2)C1] | 538.60 |

TABLE 1-continued
Representative Compounds
| Compound ID | Structure | MW |
|---|---|---|
| 20 | 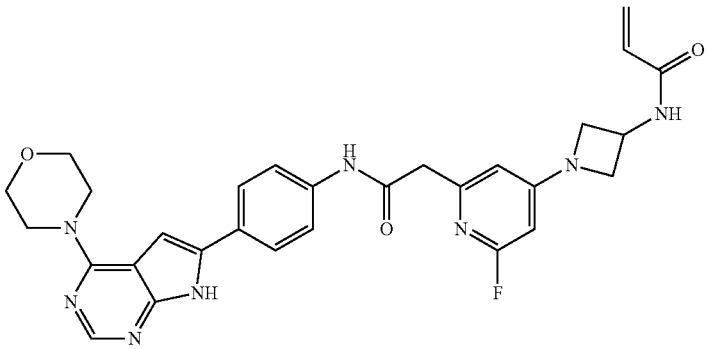 [SMILES: C=CC(=O)NC1CN(c2cc(F)nc(CC(=O)Nc3ccc(-c4cc5c(N6CCOCC6)ncnc5[nH]4)cc3)c2)C1] | 556.59 |
| 21 | 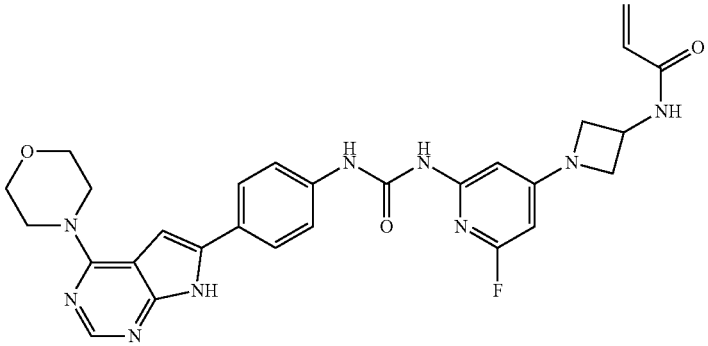 [SMILES: C=CC(=O)NC1CN(c2cc(F)nc(NC(=O)Nc3ccc(-c4cc5c(N6CCOCC6)ncnc5[nH]4)cc3)c2)C1] | 557.58 |
| 22 | 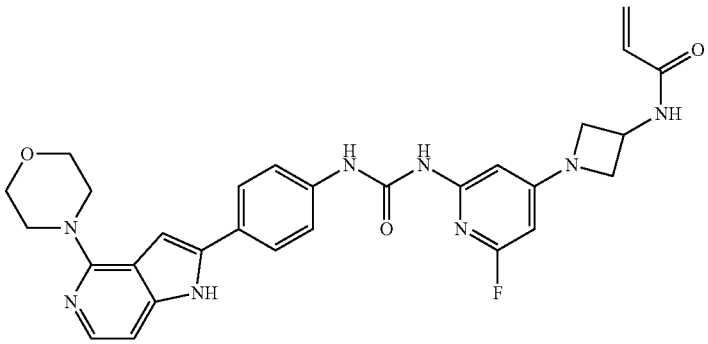 [SMILES: C=CC(=O)NC1CN(c2cc(F)nc(NC(=O)Nc3ccc(-c4cc5c(N6CCOCC6)nccc5[nH]4)cc3)c2)C1] | 556.59 |
| 23 | 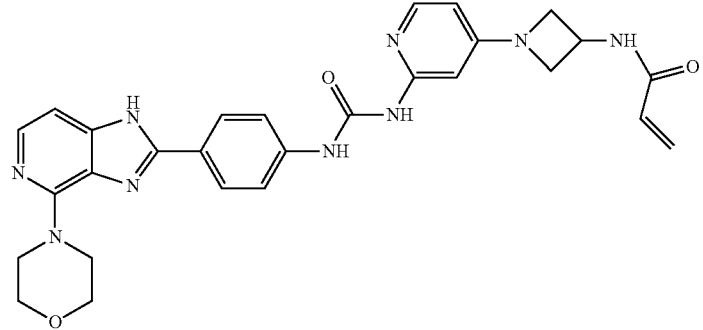 [SMILES: C=CC(=O)NC1CN(c2ccnc(NC(=O)Nc3ccc(-c4nc5c(N6CCOCC6)nccc5[nH]4)cc3)c2)C1] | 539.24 |

TABLE 1-continued

Representative Compounds

| Compound ID | Structure | MW |
|---|---|---|
| 24 | 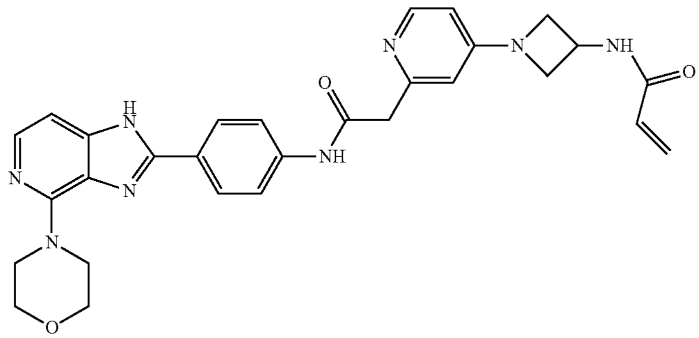 [SMILES: C=CC(=O)NC1CN(c2ccnc(CC(=O)Nc3ccc(-c4nc5c(N6CCOCC6)nccc5[nH]4)cc3)c2)C1] | 538.24 |
| 25 | 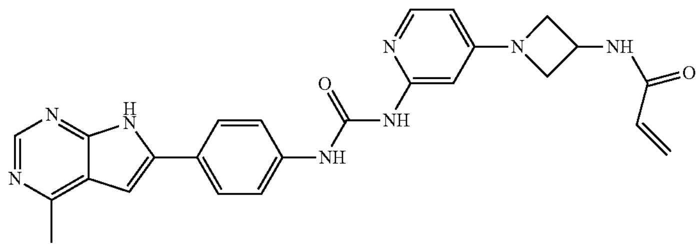 [SMILES: C=CC(=O)NC1CN(c2ccnc(NC(=O)Nc3ccc(-c4cc5c(C)ncnc5[nH]4)cc3)c2)C1] | 468.20 |
| 26 | 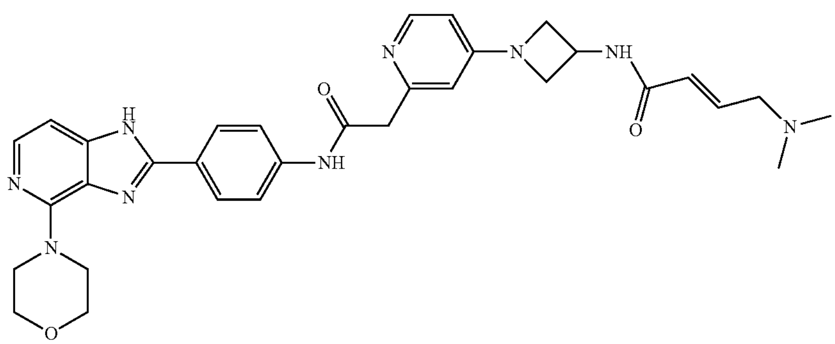 [SMILES: CN(C)C/C=C/C(=O)NC1CN(c2ccnc(CC(=O)Nc3ccc(-c4nc5c(N6CCOCC6)nccc5[nH]4)cc3)c2)C1] | 595.30 |

The following additional compounds were made or can be prepared from readily available starting materials using the general methods and procedures described herein and are depicted below in Table 2.

TABLE 2

Representative Compounds

| Compound ID | Structure | MW |
|---|---|---|
| 101 | 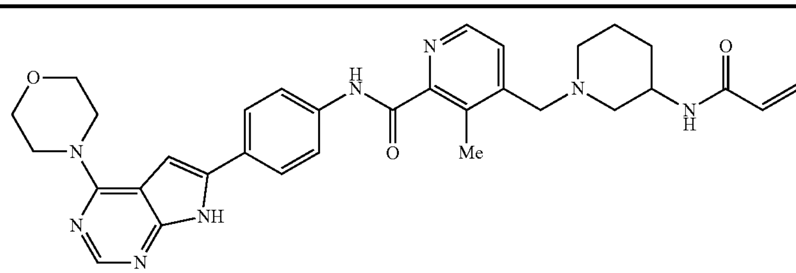 | 580.69 |

TABLE 2-continued

Representative Compounds

| Compound ID | Structure | MW |
|---|---|---|
| 102 | 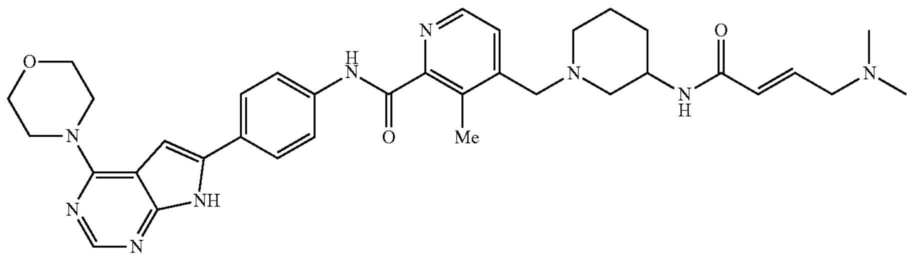 [SMILES: Cc1c(CN2CCCC(NC(=O)/C=C/CN(C)C)C2)ccnc1C(=O)Nc1ccc(-c2cc3c(N4CCOCC4)ncnc3[nH]2)cc1] | 637.79 |
| 103 | 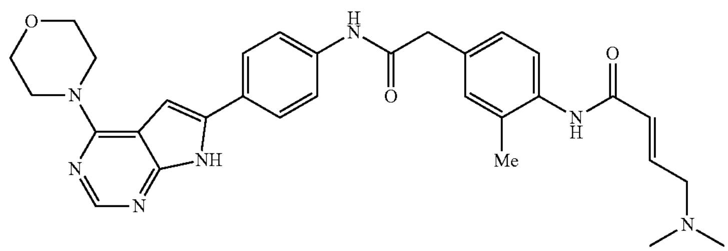 [SMILES: Cc1cc(CC(=O)Nc2ccc(-c3cc4c(N5CCOCC5)ncnc4[nH]3)cc2)ccc1NC(=O)/C=C/CN(C)C] | 553.67 |
| 104 | 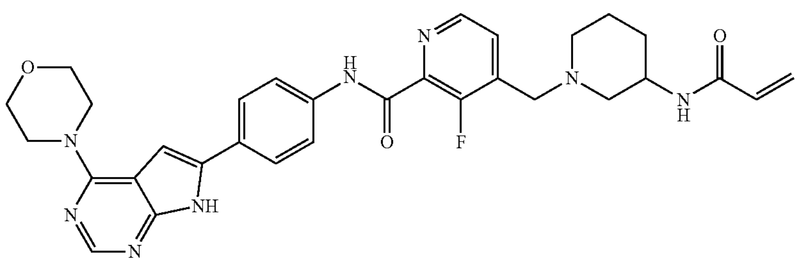 [SMILES: C=CC(=O)NC1CCCN(Cc2ccnc(C(=O)Nc3ccc(-c4cc5c(N6CCOCC6)ncnc5[nH]4)cc3)c2F)C1] | 584.66 |
| 105 | 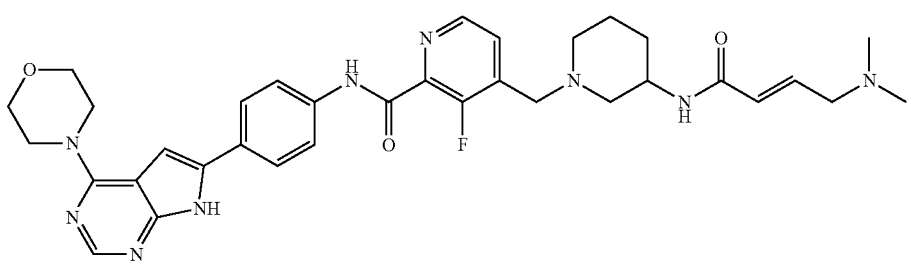 [SMILES: CN(C)C/C=C/C(=O)NC1CCCN(Cc2ccnc(C(=O)Nc3ccc(-c4cc5c(N6CCOCC6)ncnc5[nH]4)cc3)c2F)C1] | 641.75 |
| 106 | 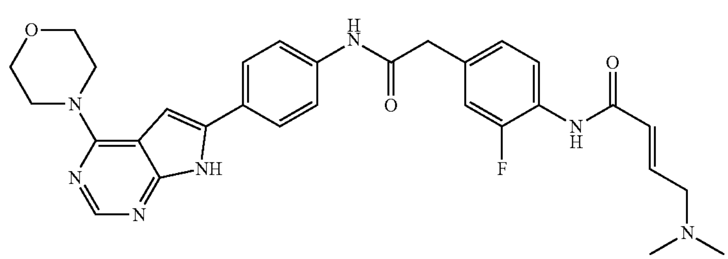 [SMILES: CN(C)C/C=C/C(=O)Nc1ccc(CC(=O)Nc2ccc(-c3cc4c(N5CCOCC5)ncnc4[nH]3)cc2)cc1F] | 557.67 |

TABLE 2-continued

Representative Compounds

| Compound ID | Structure | MW |
|---|---|---|
| 107 | 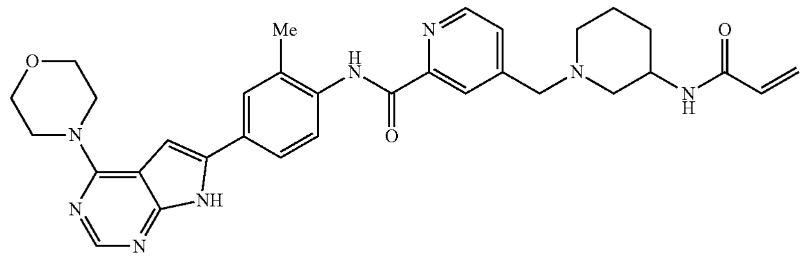 [SMILES: C=CC(=O)NC1CCCN(Cc2ccnc(C(=O)Nc3ccc(-c4cc5c(N6CCOCC6)ncnc5[nH]4)cc3C)c2)C1] | 580.69 |
| 108 | 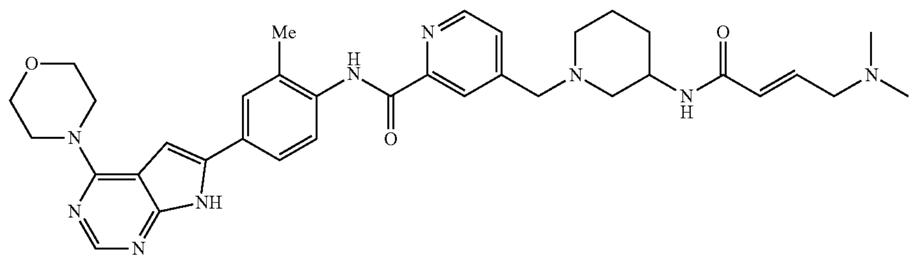 [SMILES: Cc1cc(-c2cc3c(N4CCOCC4)ncnc3[nH]2)ccc1NC(=O)c1cc(CN2CCCC(NC(=O)/C=C/CN(C)C)C2)ccn1] | 637.79 |
| 109 | 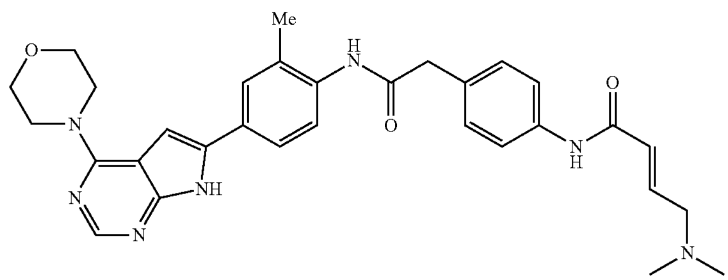 [SMILES: Cc1cc(-c2cc3c(N4CCOCC4)ncnc3[nH]2)ccc1NC(=O)Cc1ccc(NC(=O)/C=C/CN(C)C)cc1] | 553.67 |
| 110 | 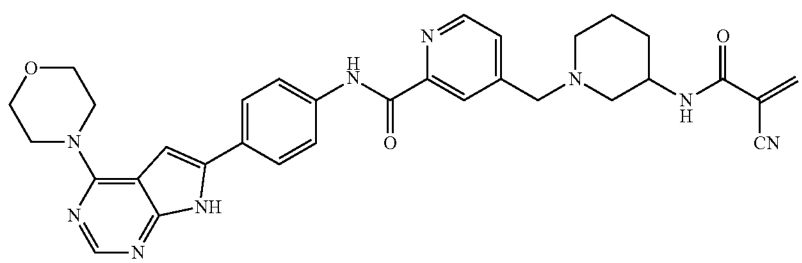 [SMILES: C=C(C#N)C(=O)NC1CCCN(Cc2ccnc(C(=O)Nc3ccc(-c4cc5c(N6CCOCC6)ncnc5[nH]4)cc3)c2)C1] | 591.68 |
| 111 | 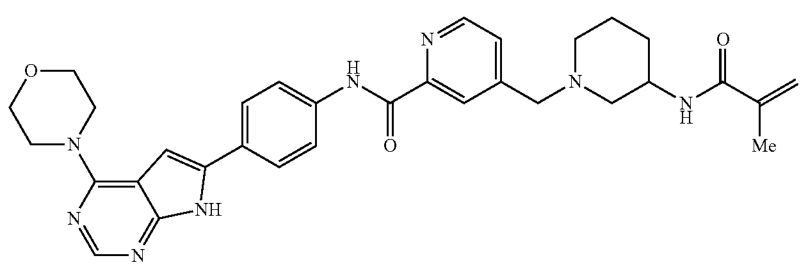 [SMILES: C=C(C)C(=O)NC1CCCN(Cc2ccnc(C(=O)Nc3ccc(-c4cc5c(N6CCOCC6)ncnc5[nH]4)cc3)c2)C1] | 580.69 |

TABLE 2-continued
Representative Compounds
| Compound ID | Structure | MW |
|---|---|---|
| 112 | 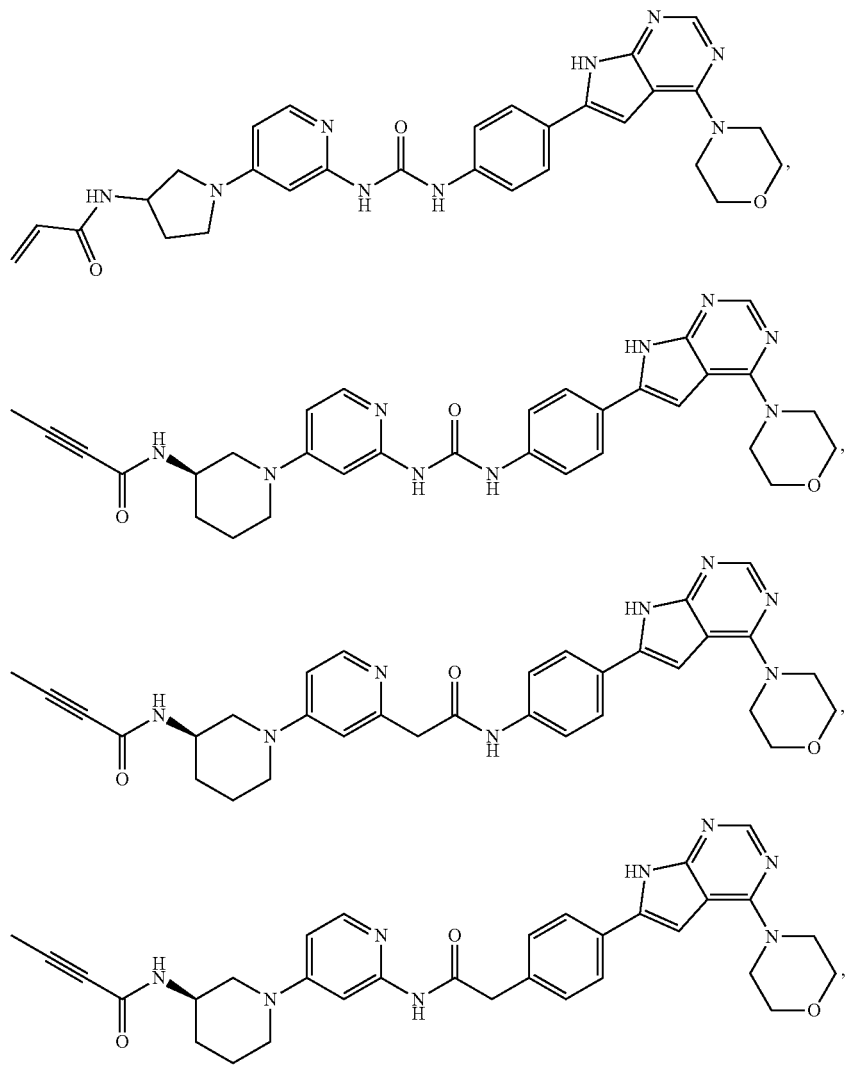 | 507.20 |
The following additional compounds were made or can be prepared from readily available starting materials using the general methods and procedures described herein and are depicted below:
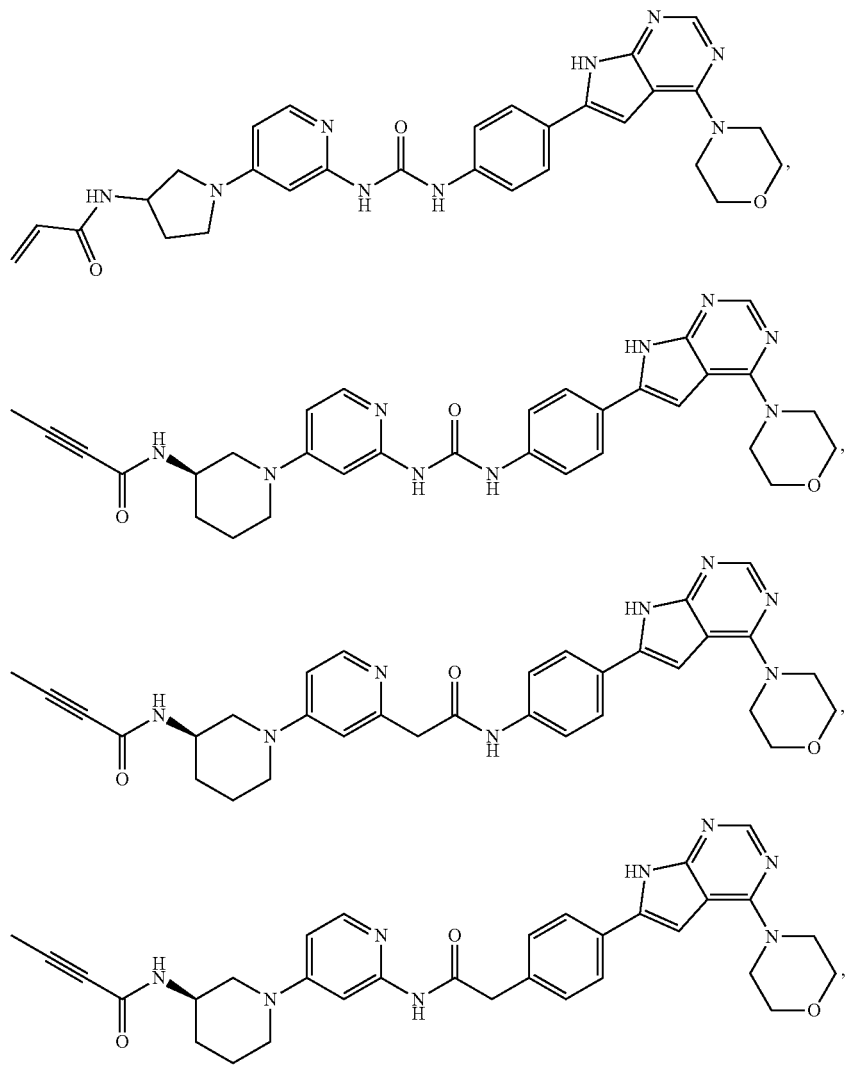

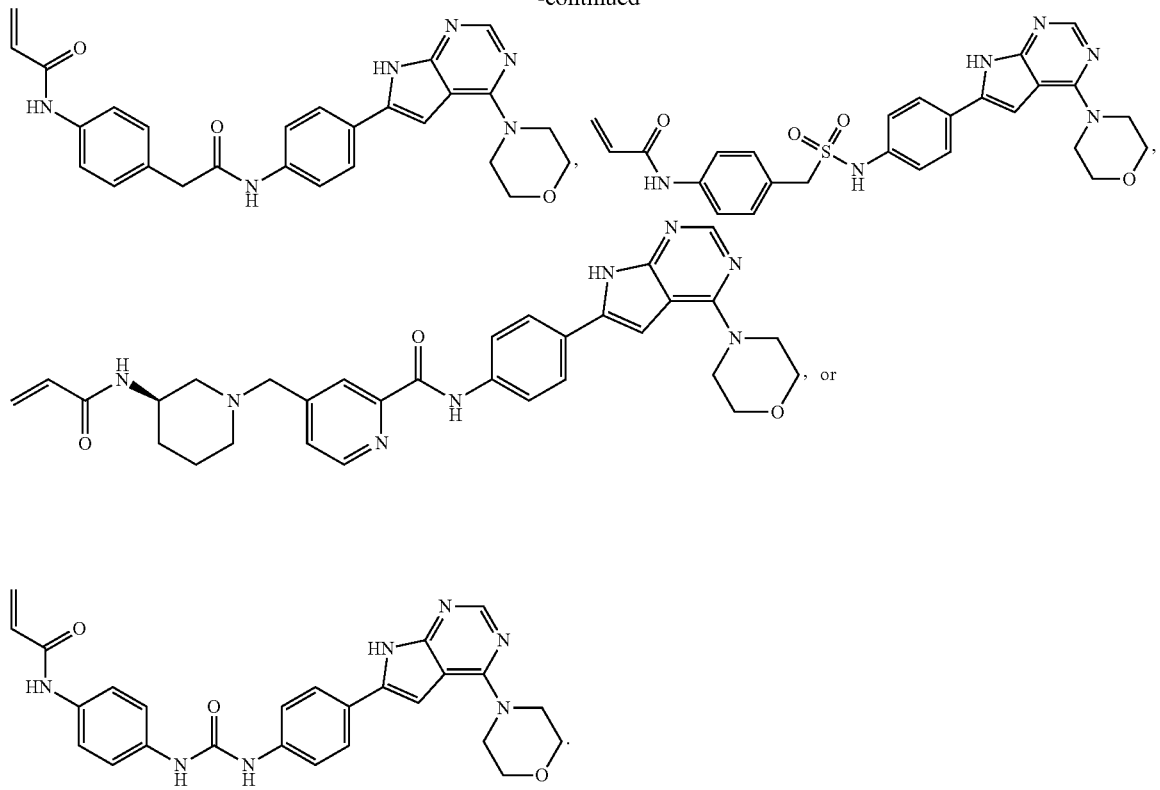

Example 101: Menin-MLL In Vitro Inhibitory Activity

The menin-MLL IC$_{50}$s of compounds disclosed herein are determined as described below.

Cell Preparation

The MLL-rearranged MOLM13 cell line and the MLL-germline cell line HL60 growing in log phase cultures was counted and re-suspended at a concentration of 10,000 cells/100 μL (100,000 cell s/mL) in RPMI 10% FBS containing medium with Pen/Strep. A total of 100 μLs were plated in each well of a round-bottom 96-well non-tissue treated plate (Corning). Thus, each well had 10,000 MOLM13 or HL60 cells on Day 1.

Compound Dilution

Each compound was diluted to a final concentration of 5 mM in DMSO. 15 mL Falcon tubes were used for making the dilution. These 5 mM stocks were stored in 2 mL light-protective Eppendorf tubes in multiple 50 μL aliquots to prevent repeated freeze-thaw cycles of the entire stock.

The following concentrations were decided for each compound: 0.01 μM, 0.03 μM, 0.1 μM, 0.3 μM, 0.5 μM, 1 μM, 3 μM, and 5 μM.

First, 2× working stocks for each desired concentration were made using the standard RPMI 10% FBS medium as the diluent.

Specifically, working stocks of 0.02 μM, 0.06 μM, 0.2 μM, 0.6 μM, 1 μM, 2 μM, 6 μM, and 10 μM (i.e., 2× the desired concentrations mentioned above) were made from the 5 mM stock.

100 μL of each working stock dilution was added to the respective well containing 100 of plated cells, thereby achieving a 1× drug concentration. A similar strategy was used for the DMSO control arm.

The IC$_{50}$s for menin-MLL inhibition were determined using methods known to one skilled in the art.

Example 102: Restoration of Glycemic Control in Diabetic Fatty Rats

The present examples provides the ability of Compound 10 to restore glycemic control to diabetic Zucker diabetic fatty rats (ZDF rats, genotype ZDF-Lepr$^{fa}$/Crl; Charles River). Cornicelli et al., 2005, Charles River.

Control and test compounds were stored at 4° C. and prepared weekly as needed. The vehicle for positive control pioglitazone was 0.25% carboxymethylcellulose and 1% Tween® 80 in reverse osmosis deionized water. The vehicle for Compound 10 was 10% DMSO, 10% Solutol HS 15, and 80% (10% hydroxypropyl-β-cyclodextrin in 50 mM citrate buffer at pH 3.0).

On Day −3, twenty-four ZDF rats (plus eight spare ZDF rats) were measured for body weight and non-fasting glucose. LabDiet 5008 was provided ad libitum throughout the study, except during designated procedures, as was water. In order to minimize the effects of stress on blood glucose and body, all animals including the spares received daily sham doses with phosphate buffered saline pH 7.2 (dose volume 5 mL/kg) via gavage beginning on Study Day −5 to Day −1.

Vehicle, control, and test compound were administered via oral gavage according to the following design on Days 1-16.

| Group No. | Test Material | Dose Level (mg/kg/day) | Dose Volume (mL/kg) | Dose Concentration (mg/mL) | Dose Regimen | Route | Number of animals |
|---|---|---|---|---|---|---|---|
| 1 | Vehicle | 0 | 10 | 0 | QD | PO | 8 |
| 2 | Pioglitazone | 30 | 10 | 3 | QD | PO | 8 |
| 3 | Compound 10 | 175 | 10 | 17.5 | QD | PO | 8 |

No. = Number;
PO = per os (oral gavage)

On Days −3, 1, 8, and 14 non-fasting blood glucose was measured. On Day 15, an oral glucose tolerance test was administered. The animals were weighed, and the animals were placed in clean cages without food. Access to water was provided throughout the procedure. The animals were fasted for five hours and a blood glucose measurement was determined. The animals were dosed via oral gavage with 2 g/kg glucose (10 mL/kg). Blood glucose was determined via tail snip. The second drop of blood from the animal was placed on a hand-held glucometer (Abbott Alpha Trak) at the following times relative to the glucose dose: zero (just prior to glucose dose), 15, 30, 60, 90, and 120 min. Following the final blood glucose measurement, food was returned to the cages. On Day 17, 4-hour fasting glucose was measured. Serum samples were used to measure insulin by ELISA. Analysis was performed in one to three days of each collections. On Day 17, terminal blood collection was obtained at about 8 mL per animal and measured for blood glucose.

Figure 1B:
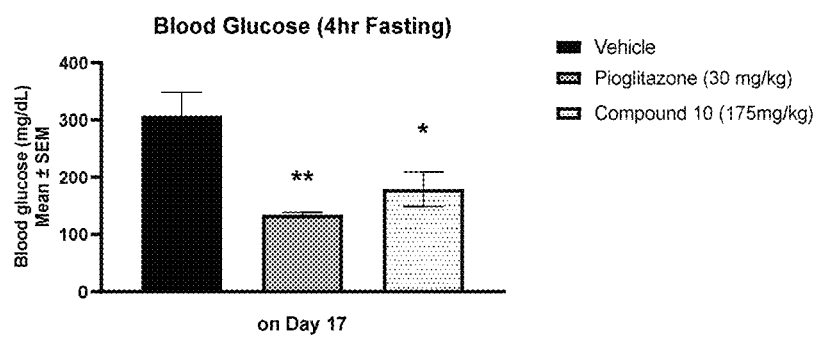
Figure 2A:
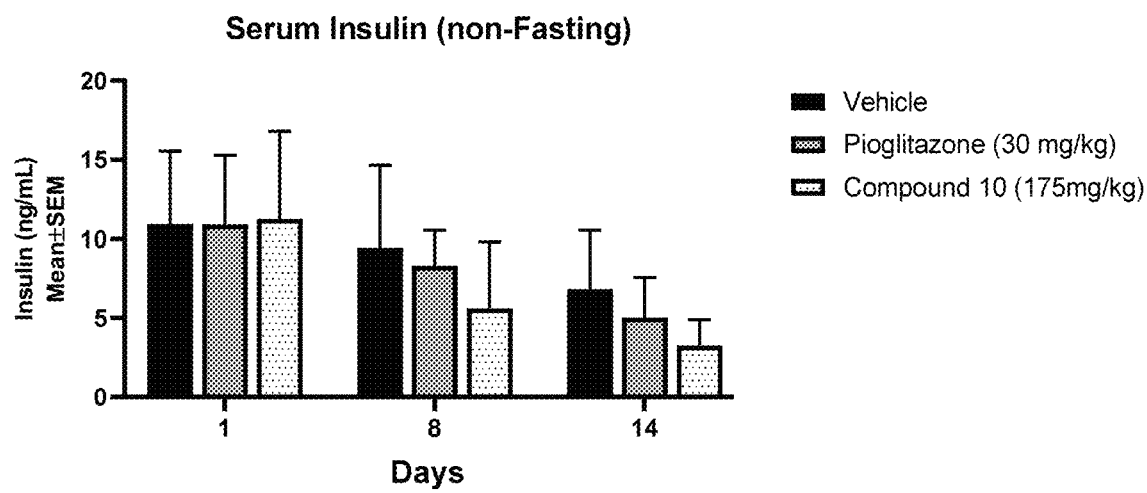
FIGS. 2A and 2B provide insulin in the non-fasting (FIG. 2A) and fasting (FIG. 2B) states following administration of Compound 10, vehicle, and control, on Days 1, 8, and 14 in ZDF rats.
Figure 2B:
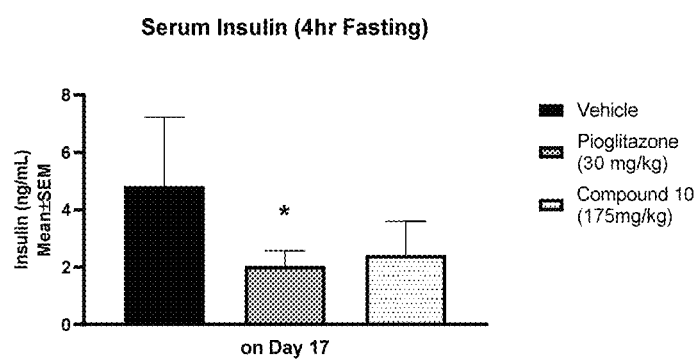
Figure 3A:
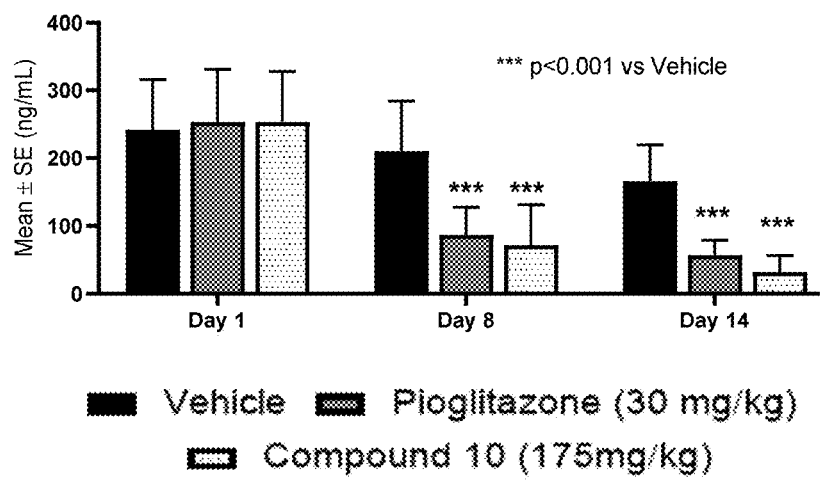
FIGS. 3A and 3B show Compound 10 in a HOMA-IR or homeostatic model assessment of insulin resistance, with results in the non-fasting (FIG. 3A) and fasting (FIG. 3B) states following administration of Compound 10, vehicle, and control, on Days 1, 8, and 14 in ZDF rats.
Figure 3B:
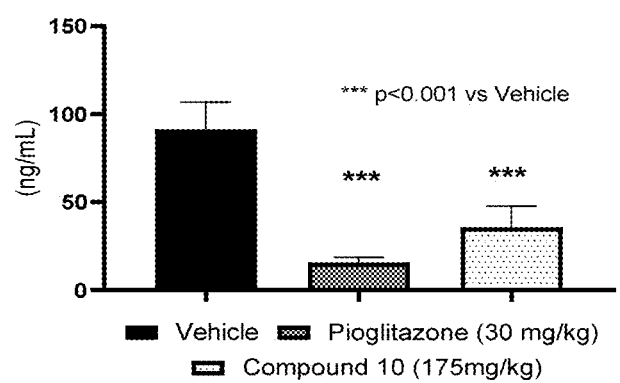

As shown in FIGS. 1A and 1B, Compound 10 provided significant reduction of glucose in the non-fasting (FIG. 1A) and fasting (FIG. 1B) states, compared to vehicle and control. As shown in FIGS. 2A and 2B, Compound 10 provided significant reduction of insulin in the non-fasting (FIG. 2A) and fasting (FIG. 2B) states, compared to vehicle and control. As shown in FIGS. 3A and 3B, Compound 10 provided significant reduction of insulin resistance (HOMA, homeostatic model assessment of insulin resistance; Turner et al., 1993, *Current Topics in Diabetes Research* 12: 66-75; Turner et al., 1979, *Metabolism.* 28(11): 1086-96) in the non-fasting (FIG. 3A) and fasting (FIG. 3B) states, compared to vehicle and control.

Figure 4A:
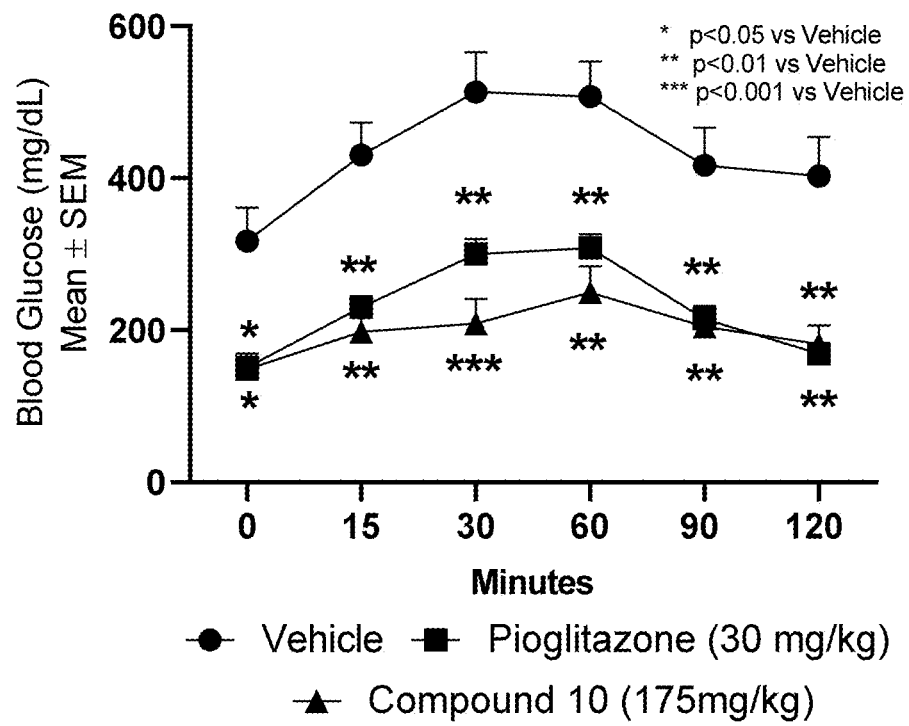
FIGS. 4A and 4B provide oral glucose tolerance test results after fourteen days of treatment with Compound 10, vehicle, and control in ZDF rats.
Figure 4B:
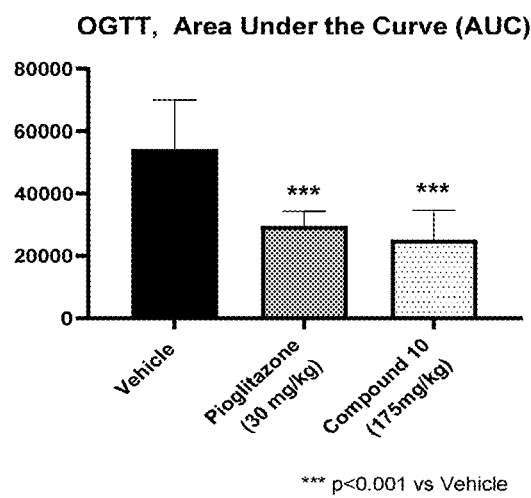
Figure 5A:
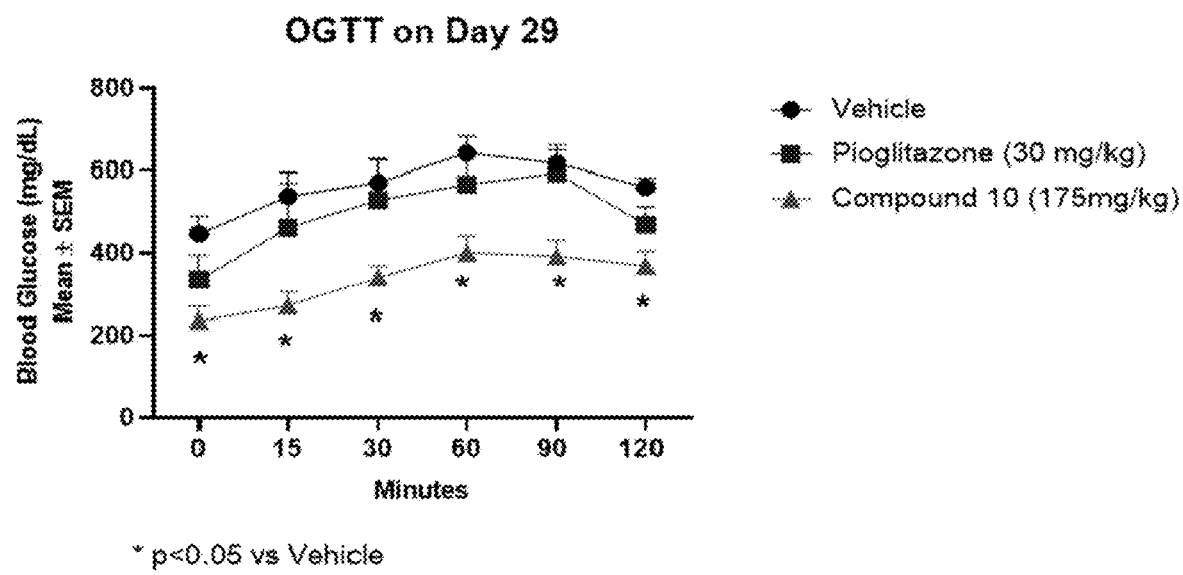
FIGS. 5A and 5B provide oral glucose tolerance test results fifteen days after fourteen days of treatment with Compound 10, vehicle, and control in ZDF rats.
Figure 5B:
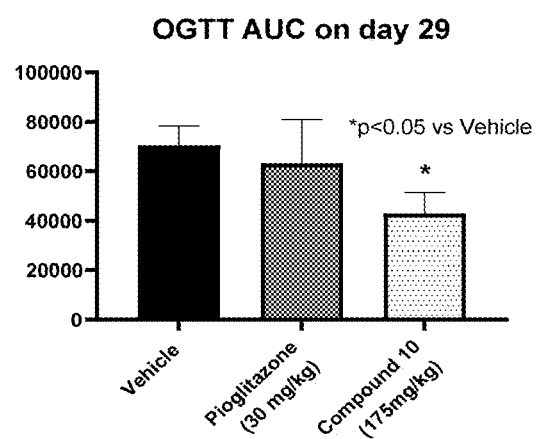
Figure 6A:
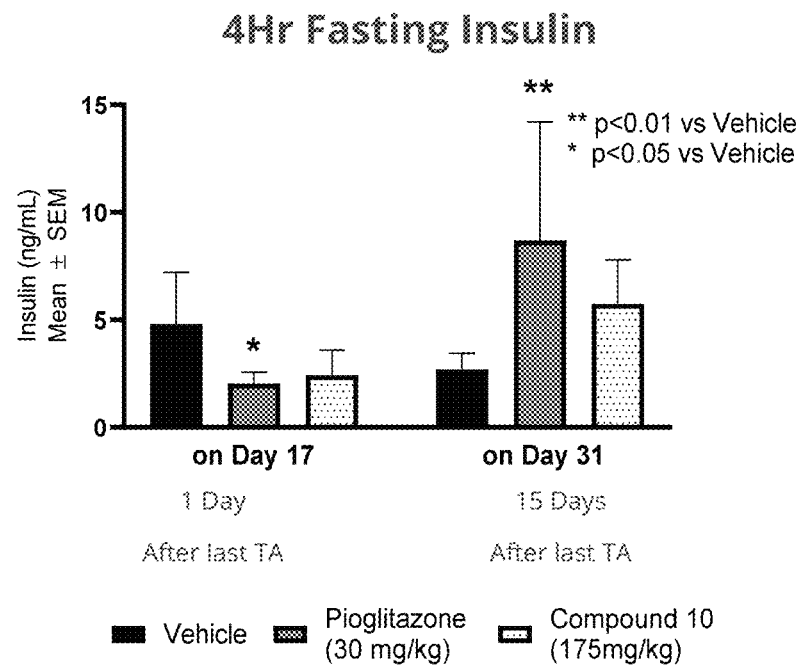
FIGS. 6A and 6B provide 4-hour fasting insulin (FIG. 6A) and 4-hour fasting glucose (FIG. 6B) at Day 17 and Day 31 (~two weeks after treatment) with Compound 10, vehicle, and control in ZDF rats.
Figure 6B:
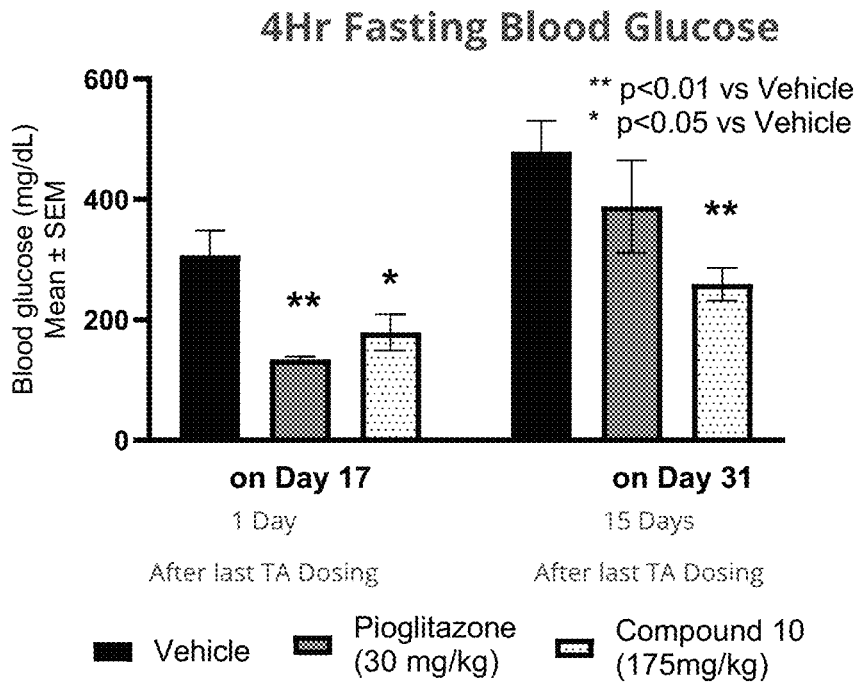
Figure 7:
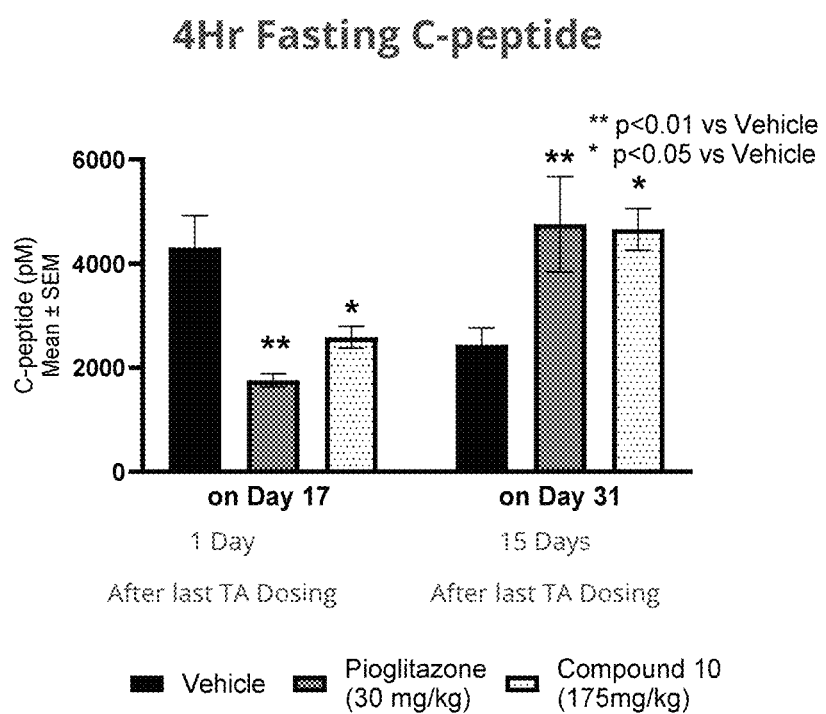
FIG. 7 provides C-peptide levels at Day 17 and Day 31 (~two weeks after treatment) treatment with Compound 10, vehicle, and control in ZDF rats.

In the oral glucose tolerance test of FIGS. 4A and 4B, Compound 10 provided significant glucose control after fifteen days of treatment. FIG. 4A provides blood glucose, and FIG. 4B provides blood glucose area under the curve data. On Day 29, even after fourteen days of no treatment, Compound 10 provided significant glucose control after fifteen days of treatment as shown in FIGS. 5A-5B. FIG. 5A provides blood glucose, and FIG. 5B provides blood glucose area under the curve data. Also on Day 29, Compound 10 showed increasing insulin and glucose lowering despite no therapy for two weeks in FIGS. 6A and 6B. The results were statistically superior to the control. FIG. 6A provides 4-hour fasting insulin, and FIG. 6B provides 4-hour fasting glucose. In FIG. 7, Compound 10 shows increasing C-peptide two weeks after therapy. C-peptide is a product of insulin synthesis indicating insulin levels.

Example 103: Restoration of Glycemic Control in Streptozotocin-Induced Rats

The present example provides the ability of Compound 10 to restore glycemic control to streptozotocin (STZ) induced type II diabetes in Wistar Han rats. Fahmy et al., 2017, World J. Pharm. Med. Res. 3(3):37-39.

Control and test compounds were stored at 4° C. and prepared weekly as needed. The vehicle for positive control pioglitazone was 0.25% carboxymethylcellulose and 1% Tween® 80 in reverse osmosis deionized water. The vehicle for Compound 10 was 10% DMSO, 10% Solutol HS 15, and 80% (10% hydroxypropyl-β-cyclodextrin in 50 mM citrate buffer at pH 3.0). The vehicle for streptozotocin pretreatment was 0.1 M sodium citrate pH 4.5.

On Day −3, twenty-four Wistar Han rats (plus eight spare Wistar Han rats) were measured for body weight and non-fasting glucose. Starting on Day −42, D12451 Research Diet was provided ad libitum throughout the study, except during designated procedures, as was water. In order to minimize the effects of stress on blood glucose and body, all animals including the spares received daily sham doses with phosphate buffered saline pH 7.2 (dose volume 5 mL/kg) via gavage beginning on Study Day −5 to Day −1. 20% Glucose in drinking water (200 g/L) was provided ad libitum for 24 hr after streptozotocin injection on Day −14 and Day −7.

On Days −14 and −7, streptozotocin was administered at 30 mg/kg/day QD intraperitoneally. Starting on Day 1, control and test compound were administered on the following schedule.

| Group No. | Test Material | Dose Level (mg/kg/day) | Dose Volume (mL/kg) | Dose Concentration (mg/mL) | Dose Regimen | Route | Number of animals |
|---|---|---|---|---|---|---|---|
| 1 | Vehicle | 0 | 10 | 0 | QD | PO | 8 |
| 2 | Pioglitazone | 30 | 10 | 3 | QD | PO | 8 |
| 3 | Compound 10 | 175 | 10 | 17.5 | QD | PO | 8 |

No. = Number;
PO = per os (oral gavage);
QD = Once a Day

On Days −7 to −1 and on Days 1, 8, and 14 non-fasting blood glucose was measured. On Day 15, an oral glucose tolerance test was administered. The animals were weighed and the animals were placed in clean cages without food. Access to water was provided throughout the procedure. The animals were fasted for five hours and a blood glucose measurement was determined. The animals were dosed via oral gavage with 2 g/kg glucose (10 mL/kg). Blood glucose was determined via venipuncture. The second drop of blood from the animal was placed on a hand-held glucometer (Abbott Alpha Trak) at the following times relative to the glucose dose: zero (just prior to glucose dose), 15, 30, 60, 90, and 120 min. Following the final blood glucose measurement, food was returned to the cages. On Day 17, 4-hour fasting glucose was measured. Serum samples were used to measure insulin by ELISA. Analysis was performed in one to three days of each collection. On Day 17, terminal blood collection was obtained at about 8 mL per animal and measured for blood glucose.

Figure 8:
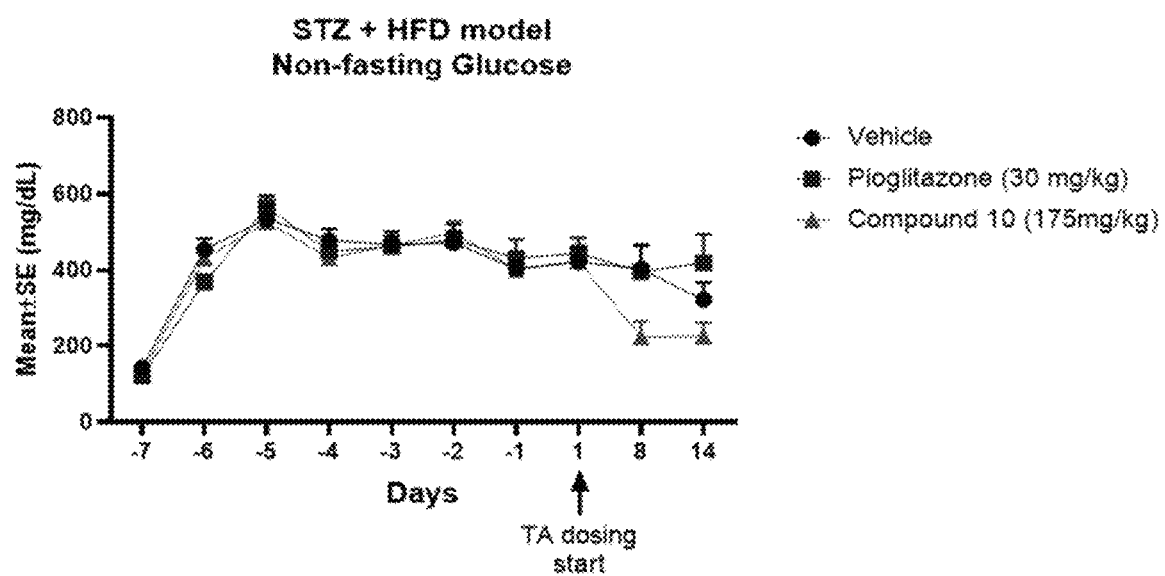
FIG. 8 provides non-fasting blood glucose levels in a streptozotocin-induced diabetes model before and after treatment with Compound 10, vehicle, and control.
Figure 9:
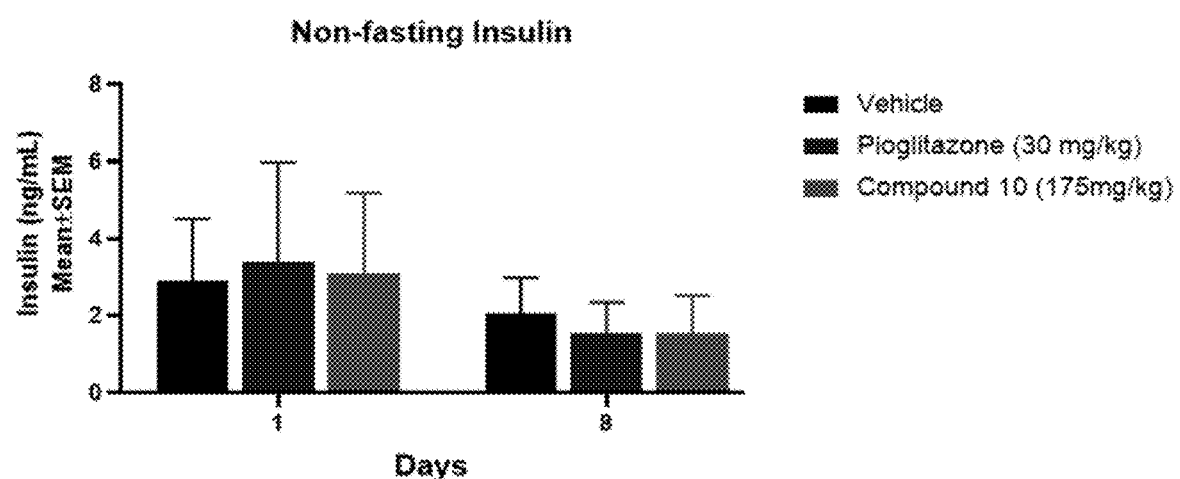
FIG. 9 provides non-fasting insulin levels in a streptozotocin-induced diabetes model after treatment with Compound 10, vehicle, and control, on Days 1 and 8.
Figure 10A:
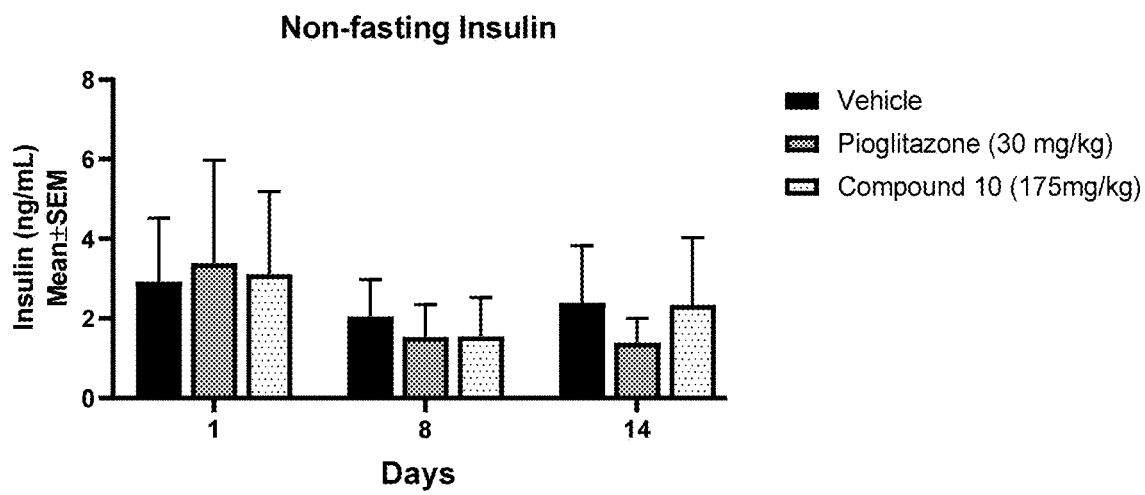
FIG. 10A provides non-fasting insulin levels in a streptozotocin-induced diabetes model after treatment with Compound 10, vehicle, and control, on Days 1, 8, and 14.
Figure 10B:
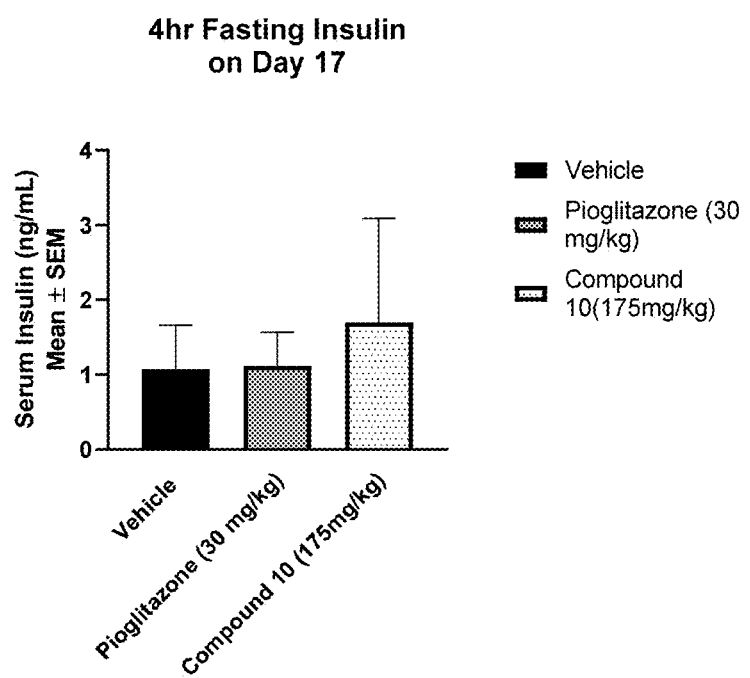
FIG. 10B provides 4-hour fasting insulin levels in a streptozotocin-induced diabetes model after treatment with Compound 10, vehicle, and control, on Day 17.

In the streptozotocin-induced diabetes model, Compound 10 provided a sharp reduction in non-fasting glucose on dosing compared to vehicle and control, as shown in FIG. 8. As shown in FIG. 9, Compound 10 provided significant reduction of insulin in the non-fasting state. As shown in FIGS. 10A and 10B, Compound 10 provided maintenance or reduction of insulin in the non-fasting (FIG. 10A) and fasting (FIG. 10B) states.

Figure 11A:
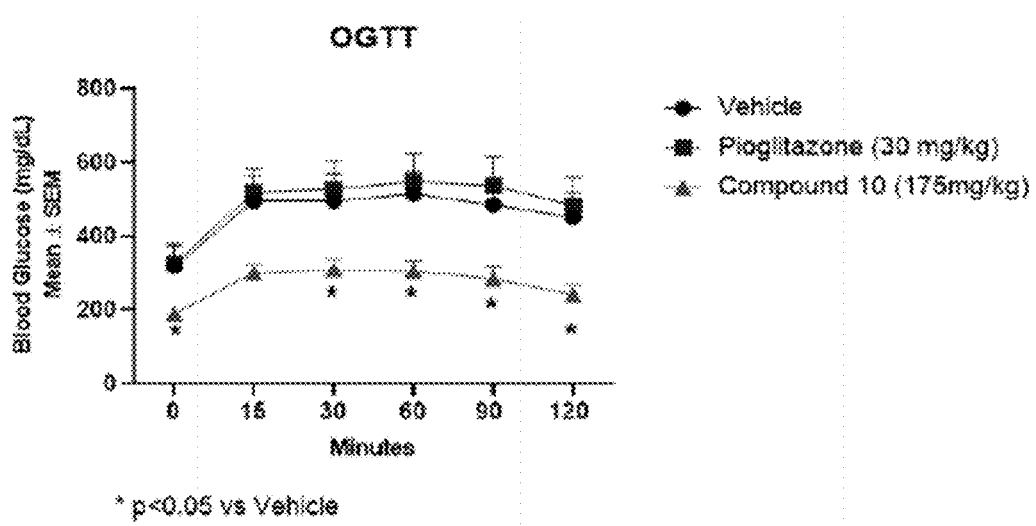
FIGS. 11A and 11B provide oral glucose tolerance test results after treatment with Compound 10, vehicle, and control, on Day 15 in streptozotocin-induced diabetic rats.
Figure 11B:
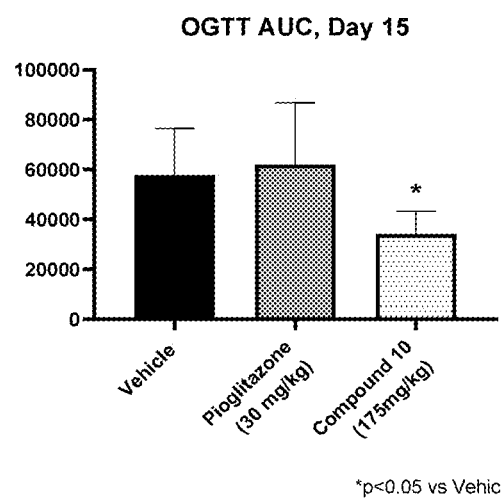

In the oral glucose tolerance test of FIGS. 11A and 1B, Compound 10 provided significant glucose control after fifteen days of treatment. FIG. 11A provides blood glucose, and FIG. 11B provides blood glucose area under the curve data. The reduction was statistically significant relative to vehicle and to control.

Example 104: Restoration of Glycemic Control in Zucker Diabetic Fatty Rats

The present example demonstrates that Compound 10 provides long-acting maintenance of glycemic control following a short course of treatment in a Type 2 Diabetes Mellitus (T2DM) Zucker Diabetic Fatty Rat model.

Rats were treated daily with Compound 10, liraglutide, or vehicle for twenty-eight days and monitored for an additional twenty-eight days post-treatment. All animals tolerated Compound 10 well throughout the study.

Figure 12:
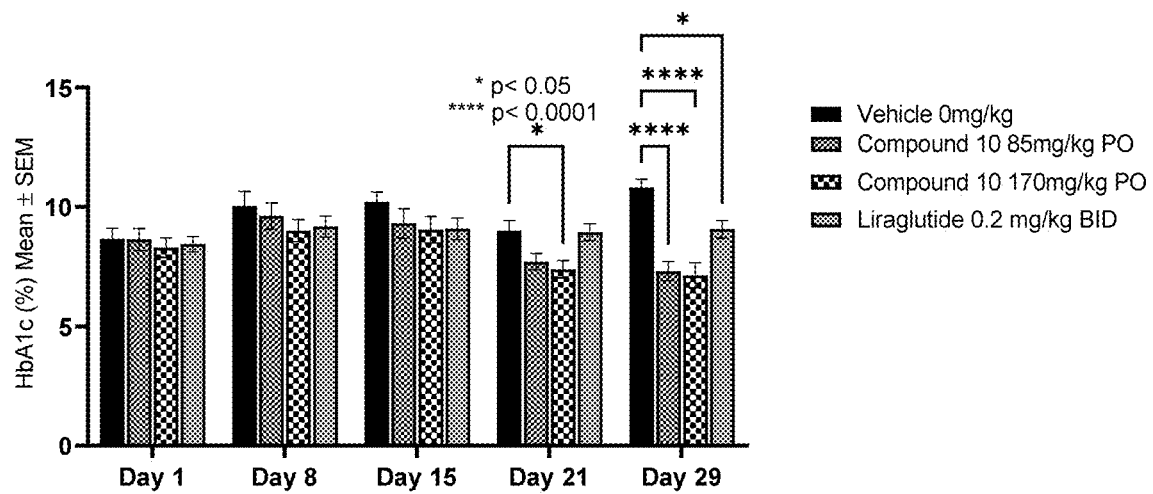
FIG. 12 provides HbA1c levels in ZDF rats on administration of vehicle, Compound 10, and liraglutide for twenty-eight days. Levels are reported on Days 1, 8, 15, 21, 29, and 43.

As shown in FIG. 12, Compound 10 treatment resulted in a significant reduction in HbA1C at Day 21, which reached 3.5% absolute reduction in HbA1C versus vehicle, compared to liraglutide (1.7% at Day 29) and remained reduced throughout the entire study, including post-treatment. The high-dose arm of Compound 10 showed a strong reduction in 4-hour fasting blood glucose during the treatment up to Day 29. Both Compound 10 dose groups showed improved glycemic control by oral glucose tolerance test (OGTT) on Day 25, in contrast to vehicle and liraglutide-treated animals. Additionally, insulin levels, HOMA-IR, HOMA-B, OGTT, HbA1C, and C-peptide levels are measured at Day 57 across all groups. Collectively, these data demonstrate the novel long-acting potential of Compound 10 as an oral treatment for T2DM in maintaining glycemic control after short-term dosing.

Example 105: Restoration of Glycemic Control in Streptozotocin-Induced Rats and Zucker Diabetic Fatty Rats The present example demonstrates that Compound 10 restores glycemic control in Zucker Diabetic Fatty (ZDF) Rat and Streptozotocin-induced Rat (STZ) models of T2DM, with prolonged glycemic control two weeks after dosing in ZDF rats.

ZDF rats were treated daily with Compound 10, vehicle, or pioglitazone for sixteen days and monitored for an additional two weeks post-treatment until Day 29. STZ rat models were induced through pre-treatment of animals on a high-fat diet with low doses of streptozotocin at Day −14 and Day −7 prior to starting treatment at Day Zero until Day 16. ZDF and STZ rats were monitored for fasting blood glucose levels, oral glucose tolerance test (OGTT), insulin and C-peptide levels, HOMA-IR (Homeostatic Model Assessment of Insulin Resistance), blood lipemic levels, and body weight according to the schematic for each model below. ZDF rats were analyzed for indicated readouts for fifteen days post-treatment for OGTT at Day 29, and serum insulin and C-peptide at Day 31.

ZDF Rat Model—three treatment groups 1. Vehicle; 2. Compound 10 at 175 mg/kg; and 3. Pioglitazone at 30 mg/kg; n=10 per group. Daily dosing zero to sixteen days QD 4 drug wash out at sixteen to twenty-nine days. Rats were monitored for the following parameters through dosing and wash out phases—body weight, fasting blood sugar, blood insulin, C-peptide, and OGTT.

STZ Rat Model—three treatment groups 1. Vehicle; 2. Compound 10 at 175 mg/kg; and 3. Pioglitazone at 30 mg/kg; n=10 per group. Fourteen-day STZ pretreatment prior to dosing. Daily dosing zero to sixteen days QD. Rats were monitored for the following parameters through dosing—body weight, blood glucose levels, and OGTT.

Figure 13A:
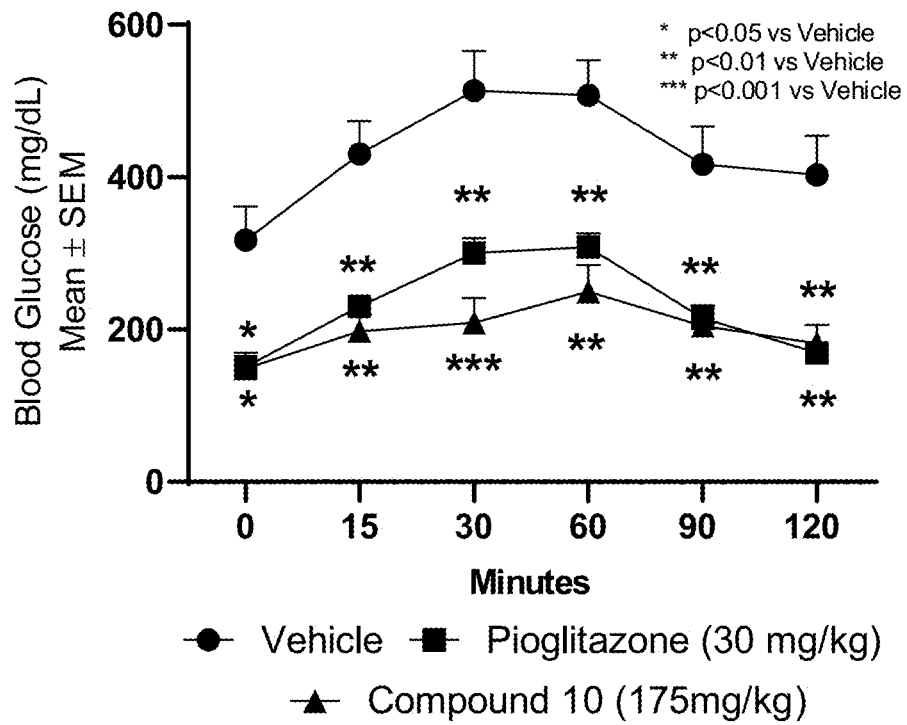
Figure 13A:
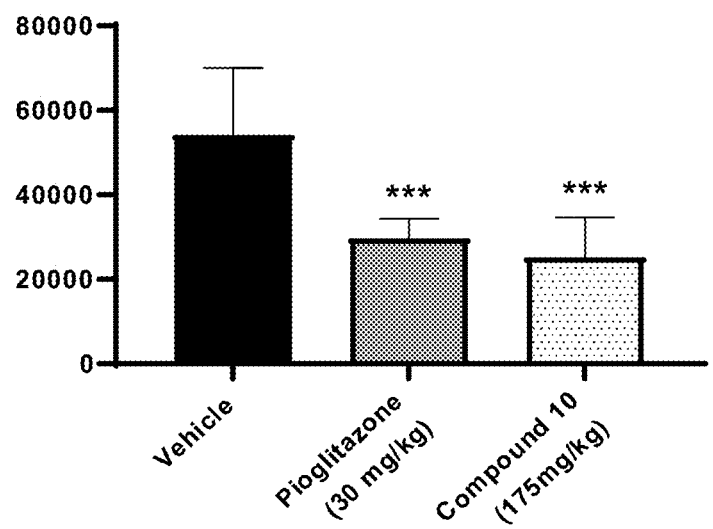
Figure 14A:
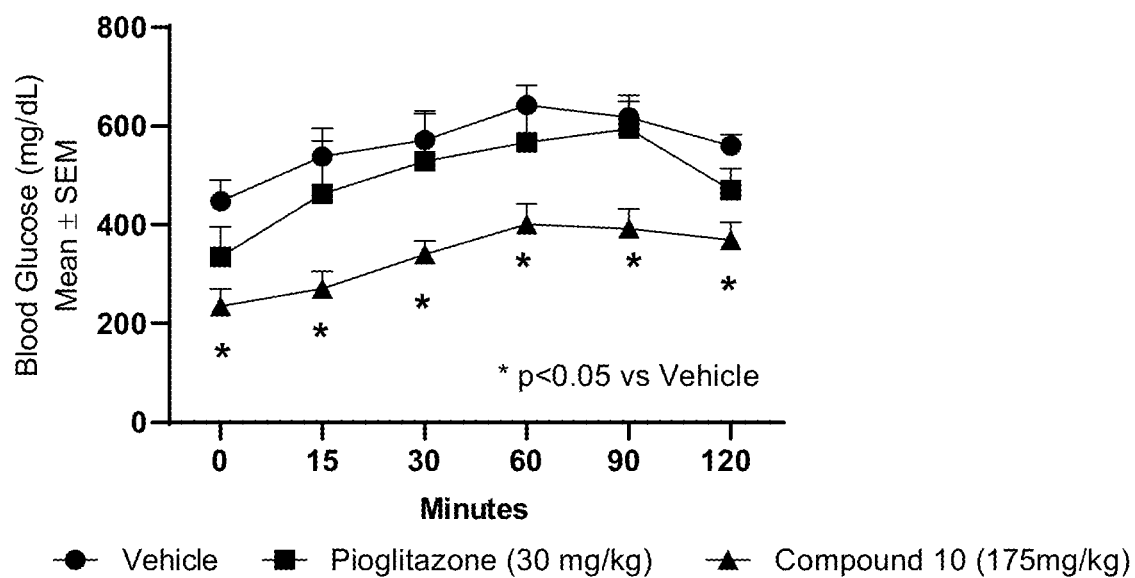
FIGS. 14A-14D show Compound 10 maintains significant impact on blood glucose, insulin, and C-peptide levels during drug washout (two weeks after last dose). ZDF rats treated with Compound 10, pioglitazone, or vehicle control for sixteen days were monitored for blood glucose levels by OGTT on Day 29, ~two weeks after administration of the last dose, displaying an AUC reduction of 40%, ($p<0.05$) (FIG. 14A), and on Day 31 monitored for 4-hour fasting blood glucose (FIG. 14B), fasting serum insulin (FIG. 14C), and fasting C-peptide levels (FIG. 14D). Statistical significance was calculated for treatment groups in comparison to vehicle control.
Figure 14A:
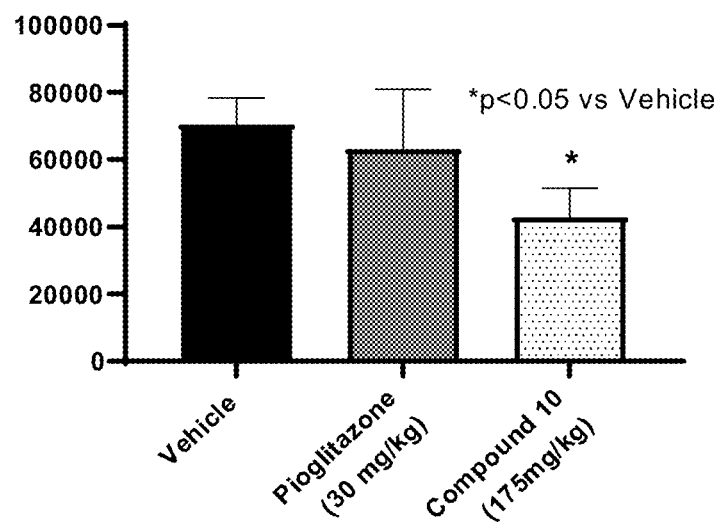
Figure 14B:
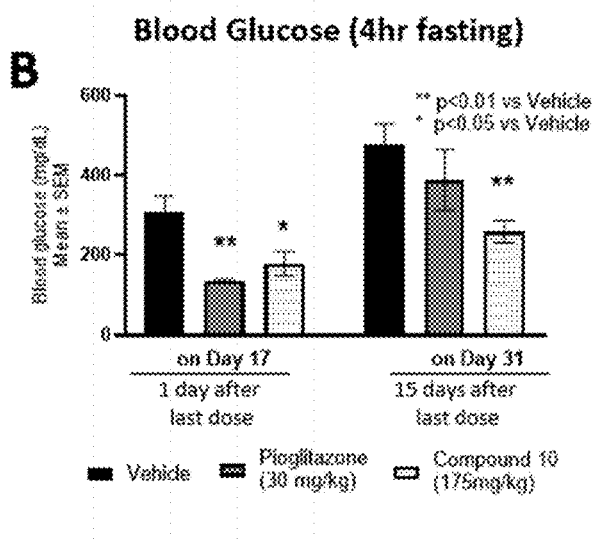
Figure 14C:
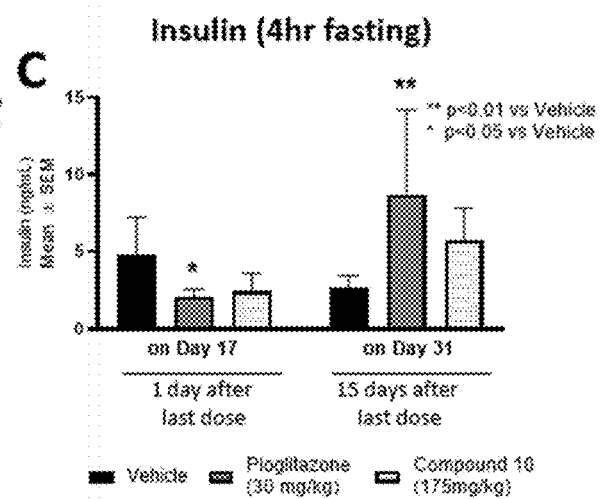
Figure 14D:
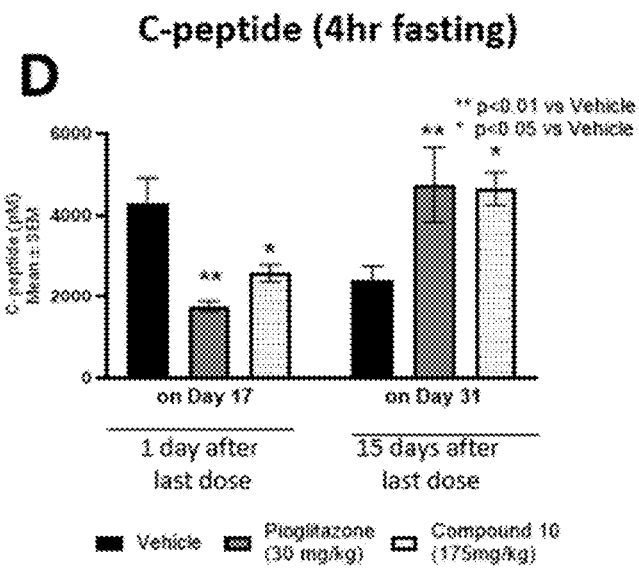

As shown in FIG. 13, Compound 10 significantly reduces blood glucose levels and alters serum insulin and C-peptide levels in ZDF rats.

As shown in FIG. 14, Compound 10 maintains significant impact on blood glucose, insulin, and C-peptide levels during drug washout (i.e., two weeks after the last dose).

Figure 15A:
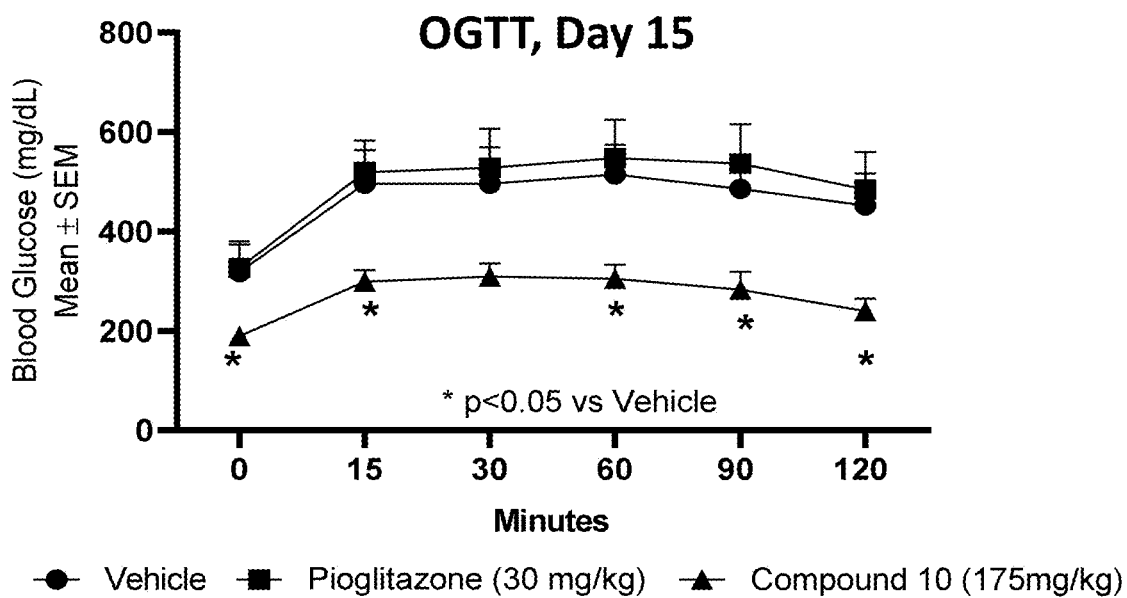
FIGS. 15A and 15B show Compound 10 strongly reduces blood glucose levels in STZ-induced rats. STZ rats pre-treated with streptozotocin for fourteen days (see methods) were treated with Compound 10, pioglitazone, or vehicle control for sixteen days. Blood glucose was measured by OGTT on Day 15 and displayed an AUC reduction of 41%, ($p<0.05$) in Compound 10 treated rats only with no change to the pioglitazone treated group (FIG. 15A). Non-fasting glucose levels were measured daily during model establishment (STZ treatment) and weekly during treatment with Compound 10, pioglitazone, or vehicle control, displaying reduction of glucose levels in Compound 10 treated rats throughout the duration of treatment (FIG. 15B).
Figure 15A:
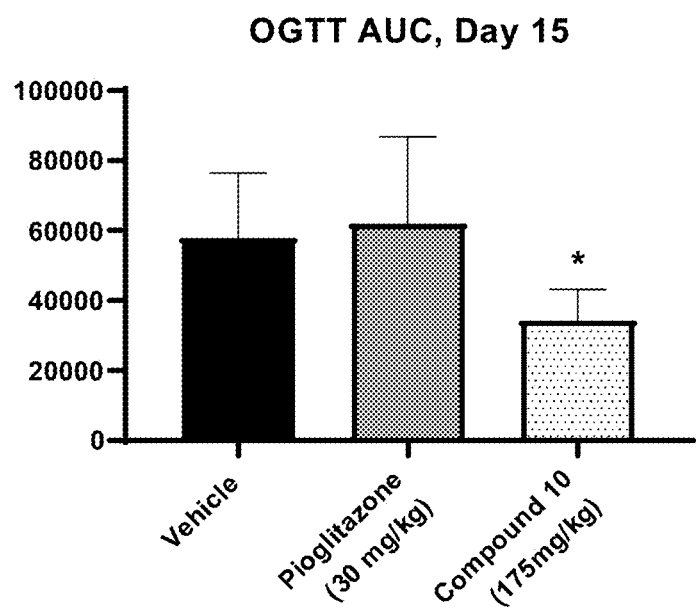
Figure 15B:
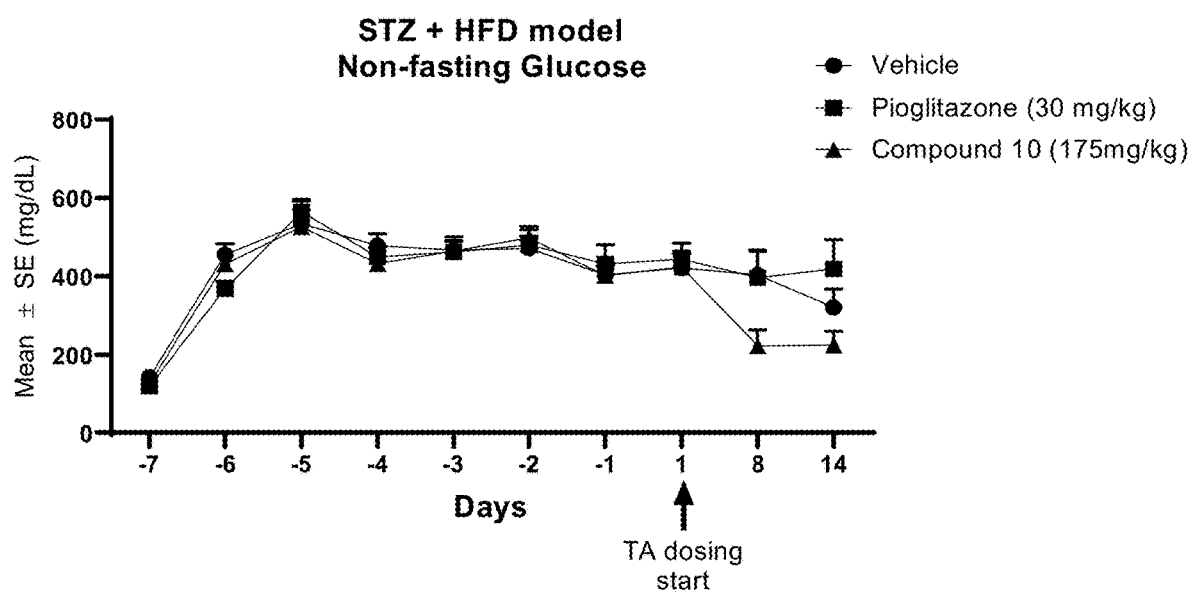

As shown in FIG. 15, Compound 10 strongly reduces blood glucose levels in STZ-induced rats.

Figure 16A:
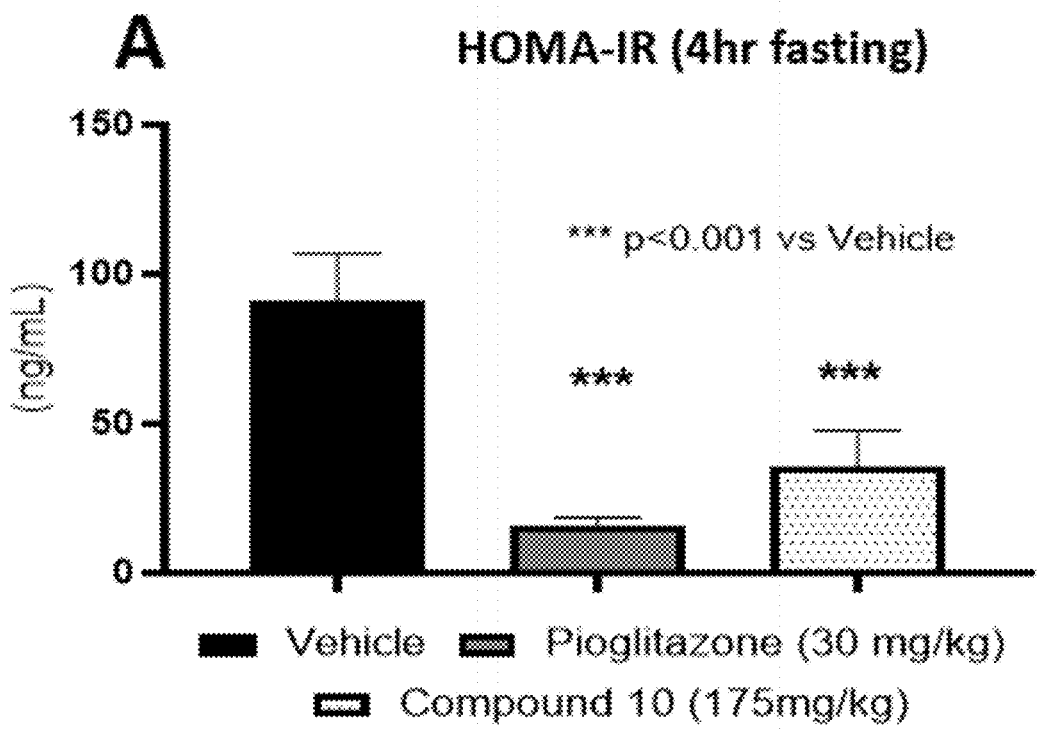
FIGS. 16A and 16B provide measurement of HOMA-IR in rats treated with Compound 10 for sixteen days. ZDF rats treated with Compound 10, pioglitazone, or vehicle were analyzed for HOMA-IR fasting at Day 17 (FIG. 16A) or non-fasting (FIG. 16B) and values were compared to vehicle control to calculate statistical significance.
Figure 16B:
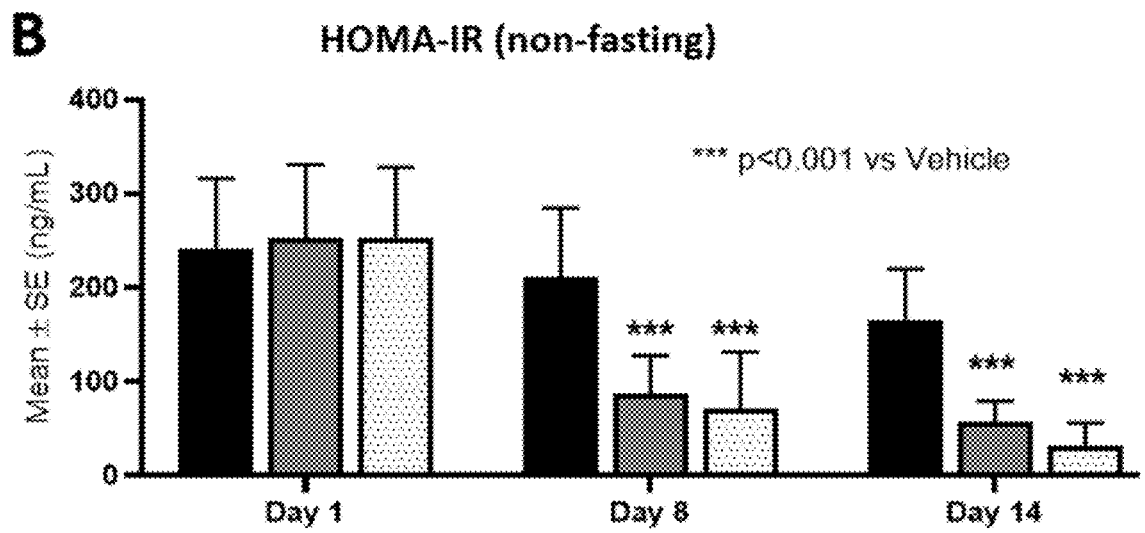

As shown in FIG. 16, Compound 10 increases insulin sensitivity in ZDF rats.

Figure 17A:
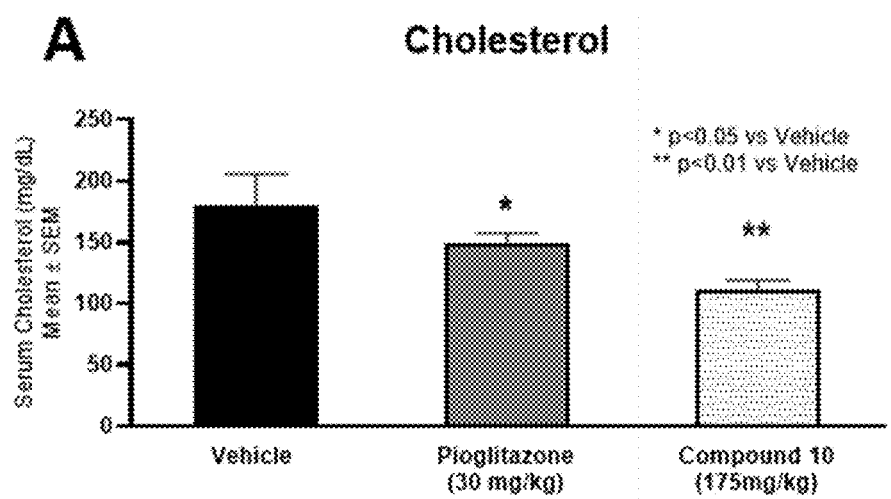
FIGS. 17A-17C provide measurement of cholesterol, triglycerides, and body weight in Compound 10 treated ZDF rats for sixteen days. Cholesterol (FIG. 17A) and triglycerides (FIG. 17B) were measured at Day 17. Body weight was measured daily during treatment and continually monitored two weeks after treatment (FIG. 17C). All groups were treated with vehicle, Compound 10, or pioglitazone and compared to vehicle for statistical analyses. Animals continued to eat a high fat diet until Day 29.
Figure 17B:
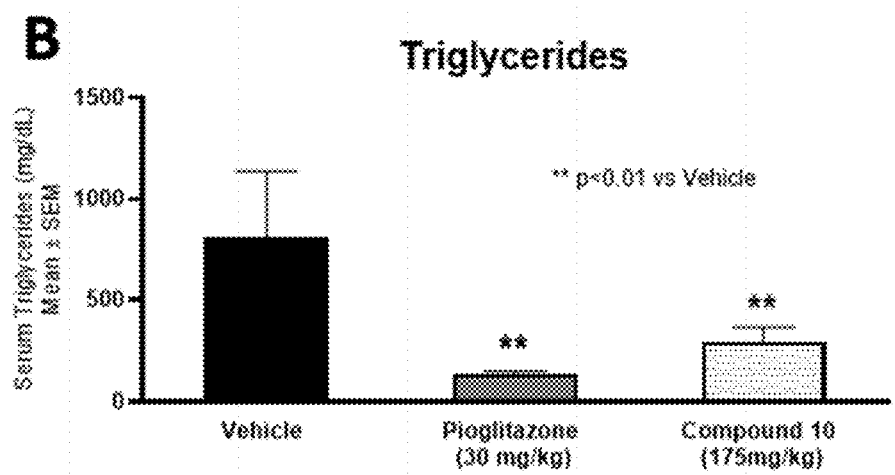
Figure 17C:
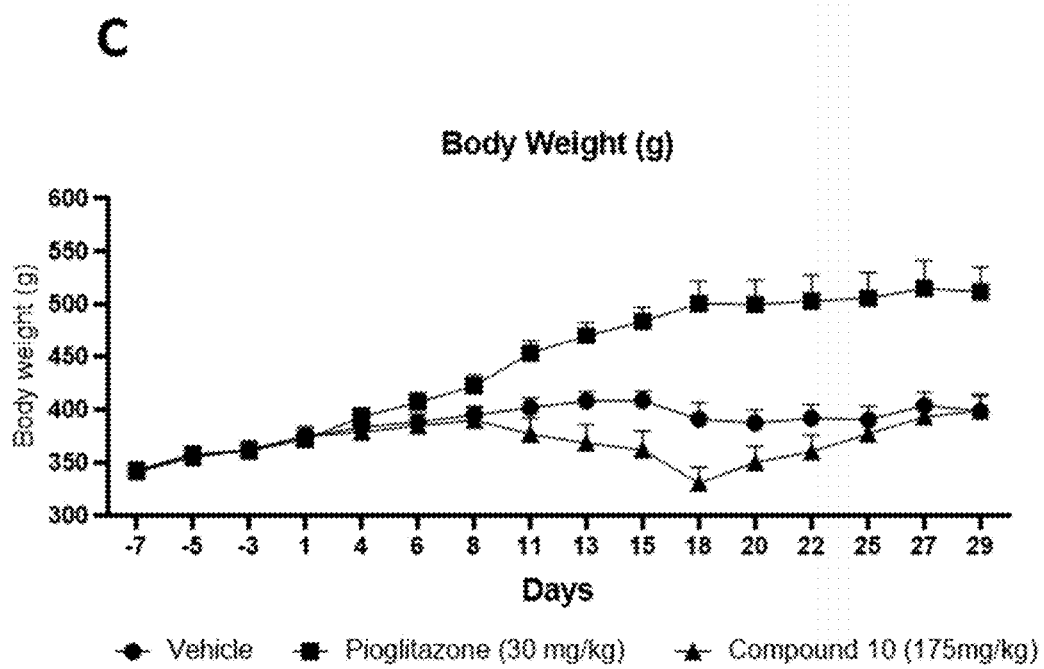

As shown in FIG. 17. Compound 10 significantly reduces blood lipemic levels and reduces body weight in treated ZDF rats.

In conclusion, Compound 10 treatment resulted in a significant reduction (~50%) in fasting and non-fasting blood glucose levels, significantly reduced serum insulin and C-peptide levels ($p<0.05$), and reduced HOMA-IR ($p<0.001$) after two weeks of treatment in ZDF rats. Additionally, Compound 10 showed prolonged glycemic control as evidenced by decreased glucose levels during an oral glucose tolerance test on Day 15 (AUC reduction of 54%, $p<0.001$) and on Day 29 during the drug washout period (AUC reduction of 40%, $p<0.05$, ~two weeks after the last dose) in the ZDF model, indicating durable glycemic control. Strikingly, Compound 10, but not pioglitazone, reduced blood glucose levels by OGTT in STZ animals (AUC reduction of 41%, $p<0.05$). Significant reductions in blood lipemic levels ($p<0.01$) and body weight were observed in both models. Collectively, the data indicate the novel and marked potential of Compound 10 as an oral, long-acting treatment for T2DM.

Example 106: Reduction in HbA1c in Zucker Diabetic Fatty Rats

The present example demonstrates that Compound 10 achieves durable glycemic control following a short course treatment in a Type 2 Diabetes Mellitus (T2DM) Zucker Diabetic Fatty Rat model.

Zucker Diabetic Fatty (ZDF) rats were dosed daily with Compound 10, liraglutide, or vehicle for twenty-eight days (n=10 per group) and monitored for an additional twenty-eight days post last dose. Fasting blood glucose, insulin, C-peptide levels, HbA1c, oral glucose tolerance test (OGTT), and body weight were monitored during and post-treatment.

ZDF Rat Model—five treatment groups 1. Vehicle; 2. Compound 10 at 40 mg/kg; 3. Compound 10 at 85 mg/kg; 4. Compound 10 at 170 mg/kg; and 5. Liraglutide at 0.2 mg/kg; n=10 per group. Group 2 dose (40 mg/kg) was increased to 200 mg/kg on Day 17 for rest of the dosing phase. Daily dosing zero to twenty-eight days days QD 4 drug wash out twenty-eight to fifty-six days. Rats were monitored for the following parameters through dosing and wash out phases—body weight, fasting blood sugar, blood insulin, C-peptide, OGTT, and HbA1C.

Figure 18:
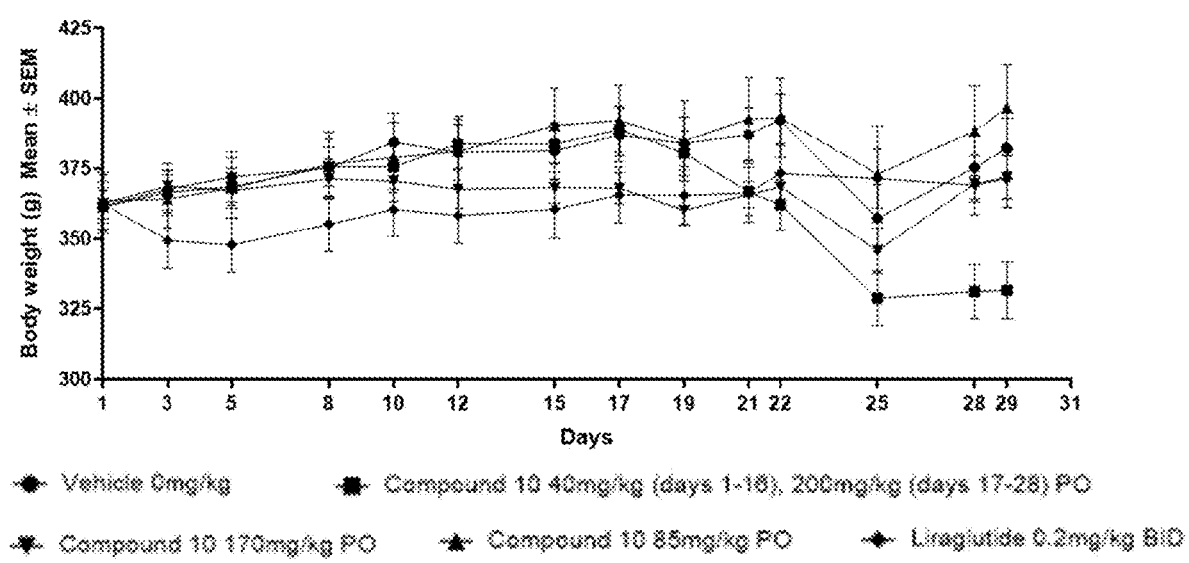
FIG. 18 provides body weight of ZDF rats during the twenty-eight days of treatment with Compound 10, liraglutide, or vehicle control. Data represents mean SEM for the dose group.

As shown in FIG. 18, Compound 10 displays progressive increase in body weight and fasting blood glucose levels over time, likely from very high food intake.

Figure 19A:
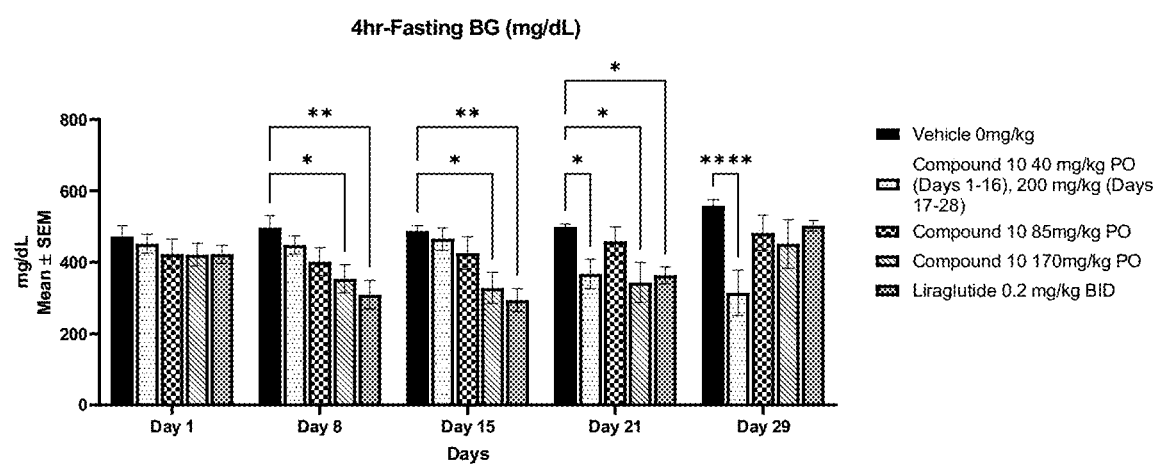
FIGS. 19A and 19B provide reduction in fasting blood glucose and HbA1c levels in Compound 10 treated ZDF rats. Rats treated with Compound 10 at indicated doses, liraglutide, or vehicle control were monitored for 4-hour fasting glucose (FIG. 19A) and HbA1c (FIG. 19B) was calculated for treated animals weekly over a 28-day treatment. Changes in blood glucose or HbA1c were compared to vehicle control to calculate statistical significance.
Figure 19B:
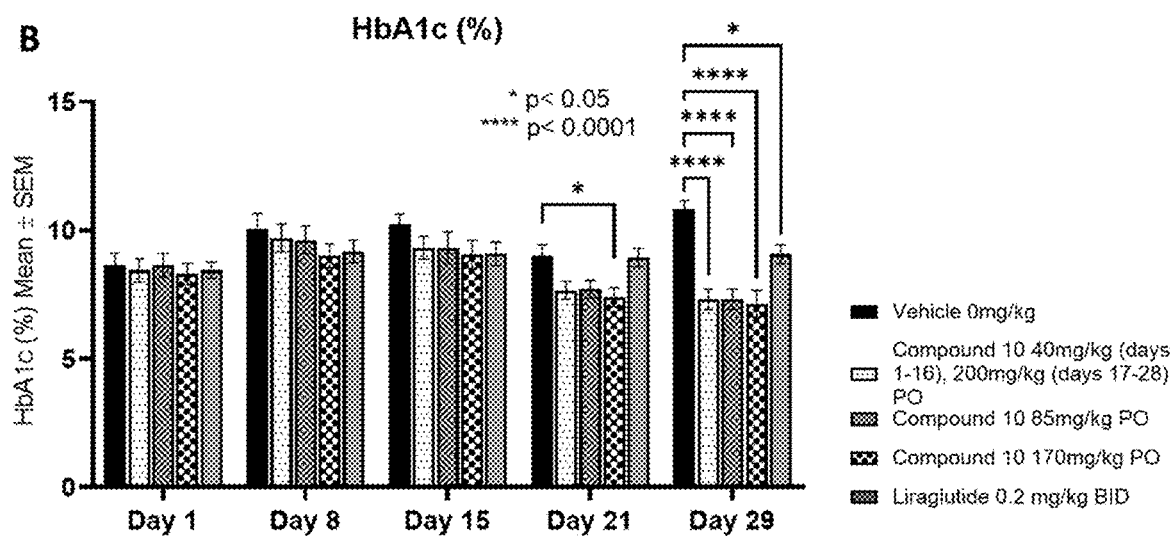

As shown in FIG. 19, Compound 10 significantly reduces HbA1c and controls blood glucose levels in a 4-week dosing study in ZDF rats.

Figure 20A:
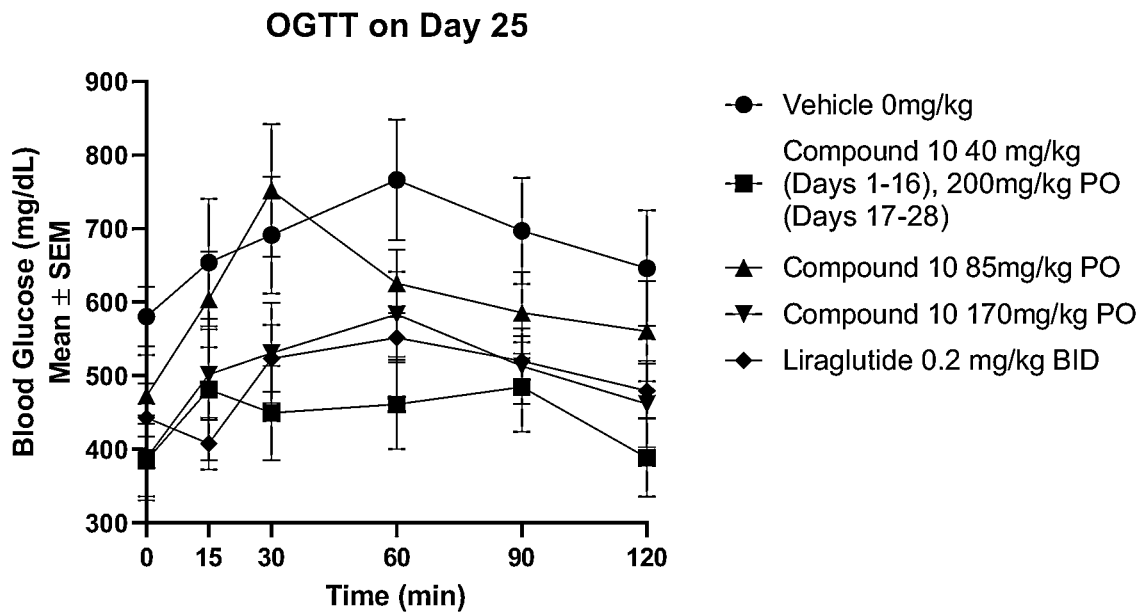
FIGS. 20A-20C show Compound 10 exerts strong glycemic control over 28-days of treatment in ZDF rats. OGTT was conducted on Day 25 on rats treated with Compound 10 at indicated doses, liraglutide, or vehicle control by measurement of blood glucose at fifteen and thirty minute intervals up to two hours (FIG. 20A). Fasting insulin (FIG. 20B) and C-peptide (FIG. 20C) levels were measured weekly over twenty-eight days in rats treated with Compound 10 at indicated doses, liraglutide, or vehicle control. Insulin and C-peptide levels were also measured on Day 43 (fifteen days after the last dose was administered).
Figure 20B:
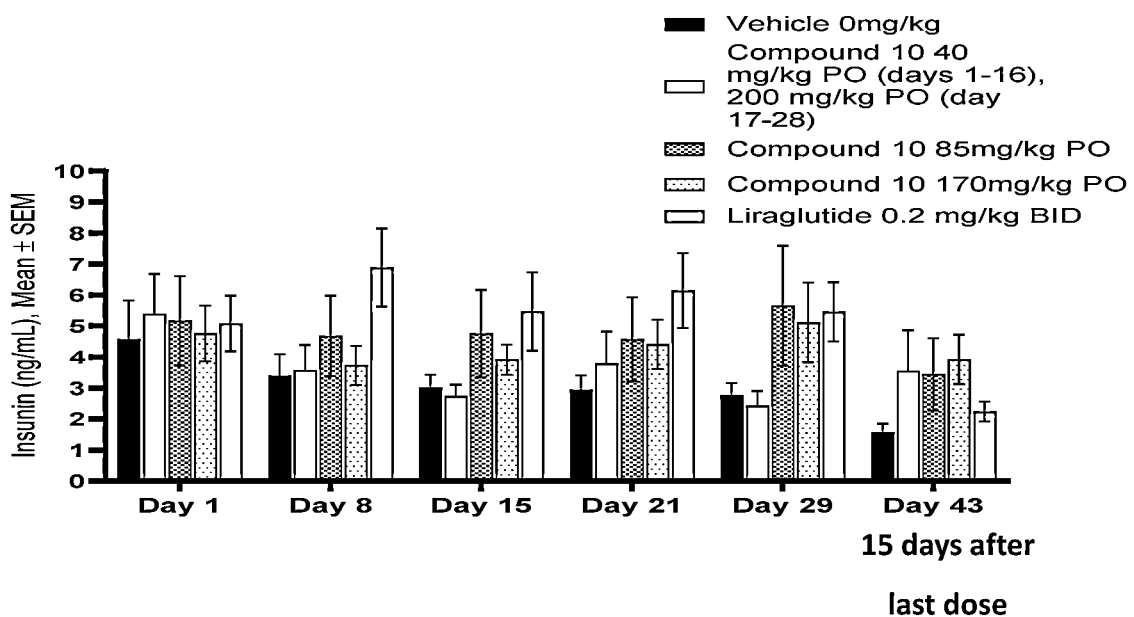
Figure 20C:
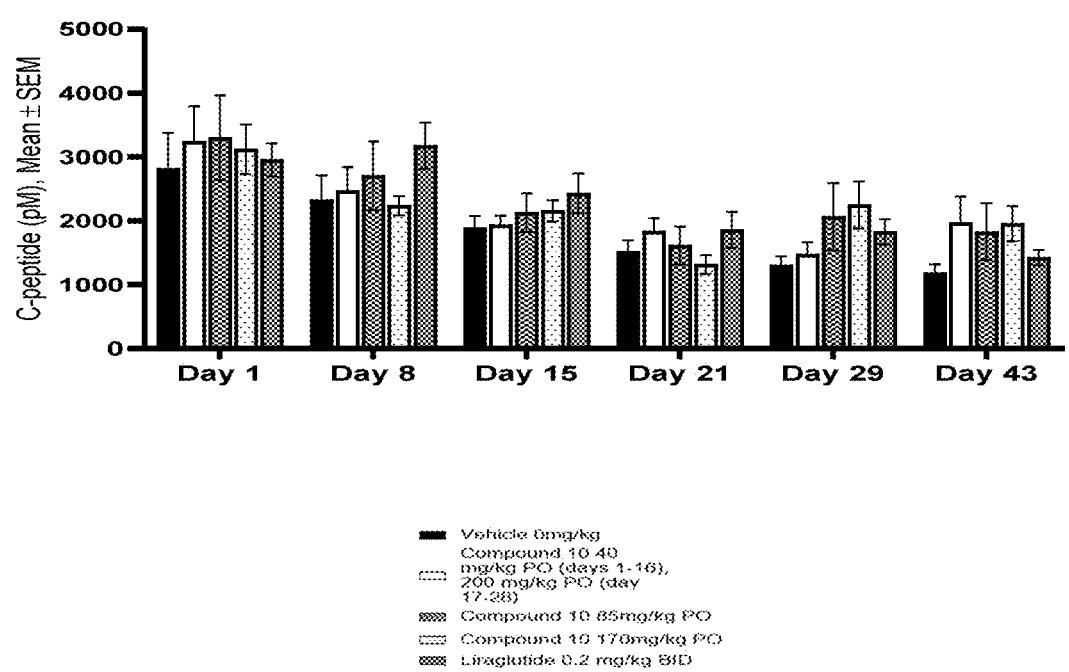
Figure 21:
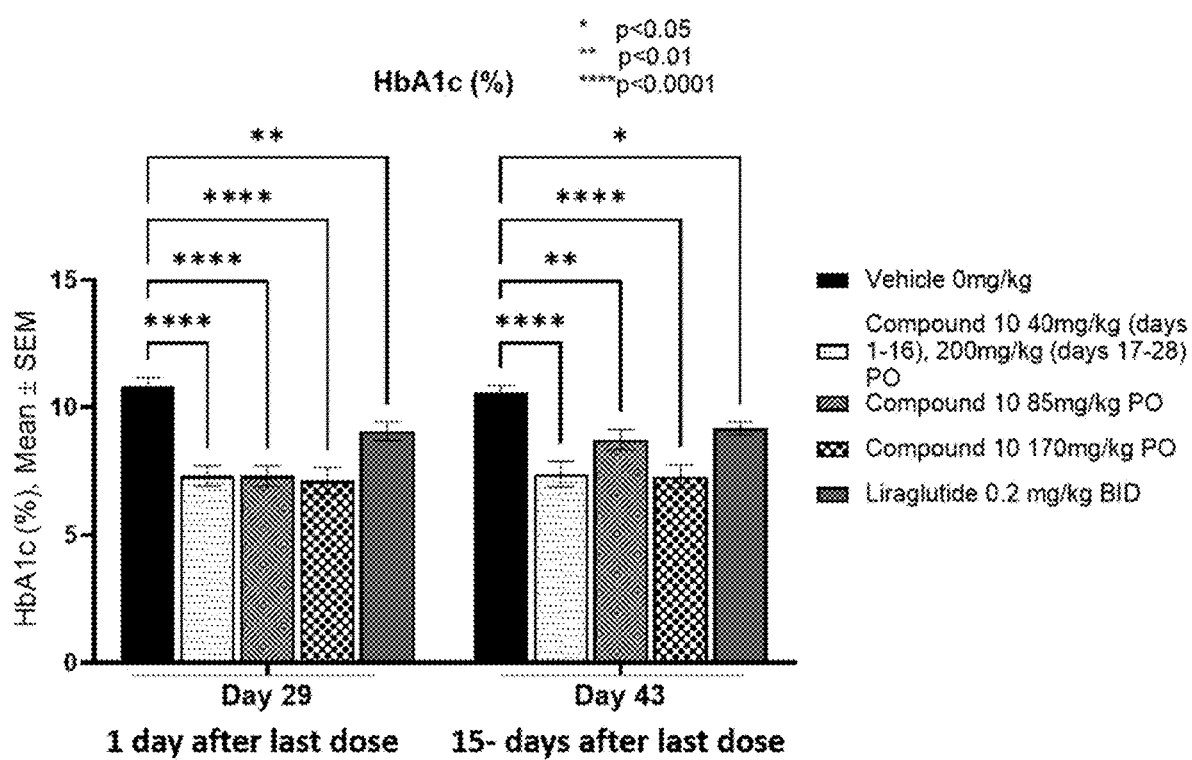
FIG. 21 provides HbA1c levels measured two weeks after administration of a last dose in ZDF rats. Rats treated for twenty-eight days with Compound 10 at indicated doses, liraglutide, or vehicle control were monitored for HbA1c levels on Day 1 and Day 15 post-dosing. Drug-treated groups are compared to vehicle control to calculate statistical significance by two-way ANOVA.

As shown in FIG. 20, Compound 10 displays durable glycemic control over four weeks of dosing As shown in FIG. 21, Compound 10 maintains a significant reduction of HbA1c two weeks after the last dose In conclusion, Compound 10 mid- and high-dose arms showed reduction in fasting blood glucose levels similar to liraglutide. On Day 29 (i.e., one day after treatment stopped), Compound 10 high-dose group showed sustained and significant reduction in fasting blood glucose. Compound 10 treatment reduced HbA1c levels by Day 21 of treatment. Absolute amounts were lower than the vehicle group by 3.5% (i.e., 33% reduced from vehicle) and lower than the liraglutide group by 1.8% (i.e., 20% reduced from vehicle) on Day 29, and remained reduced throughout the study, including post-treatment. All Compound 10 dose groups showed improved glycemic control by oral glucose tolerance test (OGTT) on Day 25, in comparison to the vehicle-treated group, with the high-dose-treated group showing improved response versus liraglutide. Fasting insulin and c-peptide levels were elevated in Compound 10 treated animals up to the last day of dosing, with the effects lasting well into two weeks post last dose. Compound 10 induced significant reductions in HbA1c at all doses tested, with the effects lasting fifteen days after the last dose.

It is understood that the examples and embodiments described herein are for illustrative purposes only and that various modifications or changes in light thereof will be suggested to persons skilled in the art and are to be included within the spirit and purview of this disclosure and the scope of the appended claims. All publications, patents, and patent application publications cited herein are hereby incorporated by reference herein in their entirety for all purposes.

At least some of the chemical names of compounds described herein, may have been generated on an automated basis by use of a commercially available chemical naming software program, and have not been independently verified. In the instance where the indicated chemical name and the depicted chemical structure differ, the depicted chemical structure will control. In the chemical structures where a chiral center exists in the chemical structure, but no specific stereochemistry is shown for the chiral center, both enantiomers associated with the chiral chemical structure are encompassed by the chemical structure.

What is claimed is:

1. A method for reducing HbA1c in a patient in need thereof, comprising administering to the patient a therapeutically effective amount of a compound according to Formula (I)

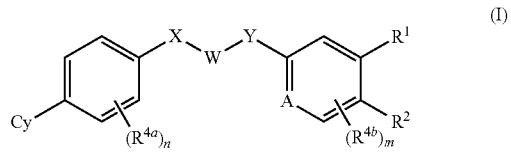

or a pharmaceutically acceptable salt thereof, wherein

A is carbon or nitrogen;

Cy is substituted or unsubstituted

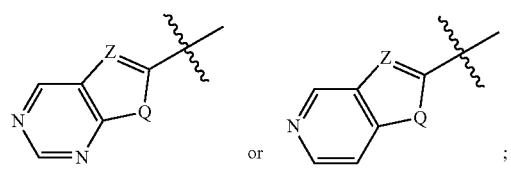

Q is —N(H)—;

Z is —$CR^{5a}$= or —N=;

X is —$NR^{3a}$— or —$C(R^{3b})_2$—;

Y is a single bond, —$NR^{3a}$—, or —$C(R^{3b})_2$—;

W is —C(O)— or —$S(O)_2$—;

one of $R^1$ and $R^2$ is $Cy^2$-N(H)C(O)—$C(R^{6a})$=$C(R^{6b})(R^{6c})$ or $CH_2$-$Cy^2$-N(H)C(O)—$C(R^{6a})$=$C(R^{6b})(R^{6c})$; and the other is hydrogen;

$Cy^2$ is an optionally substituted group selected from phenyl, pyridyl, or a 4- to 7-membered heterocycloalkyl ring having one nitrogen;

each $R^{3a}$ and $R^{3b}$ is hydrogen;

each $R^{4a}$ and $R^{4b}$ is independently hydrogen, fluoro, or methyl;

$R^{5a}$ is hydrogen;

each $R^{6a}$ and $R^{6b}$ is independently hydrogen or $C_{1-6}$ alkyl; or $R^{6a}$ and $R^{6b}$ are joined together to form a bond;

$R^{6c}$ is hydrogen or substituted or unsubstituted $C_{1-6}$ alkyl;

m is one, two, or three; and n is one, two, three, or four.

2. The method according to claim 1, wherein —X—W—Y— is —N(H)—C(O)—N(H)—, —N(H)—C(O)—$CH_2$—, —$CH_2$—C(O)—N(H)—, —N(H)—$S(O)_2$—N(H)—, —N(H)—$S(O)_2$—$CH_2$—, —$CH_2$—$S(O)_2$—N(H)—, or —N(H)—C(O)—.

3. The method according to claim 1, wherein the compound is according to Formula (XXIIIa), (XXIIIb), (IVa), or (IVb)

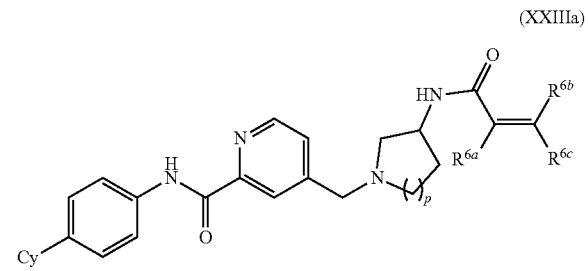

-continued

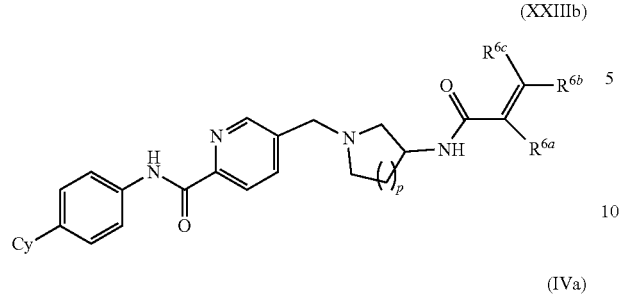

(XXIIIb)

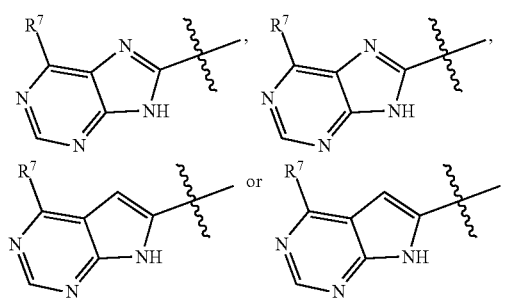

(IVa)

(IVb)

or a pharmaceutically acceptable salt thereof; and wherein p is zero, one, two, or three.

4. The method according to claim 1, wherein Cy is wherein $R^7$ is

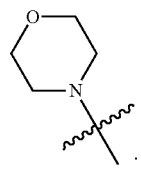 [SMILES: *N1CCOCC1]

5. The method according to claim 1, wherein the compound is according to Formula (XXIVa) or (XXIVb)

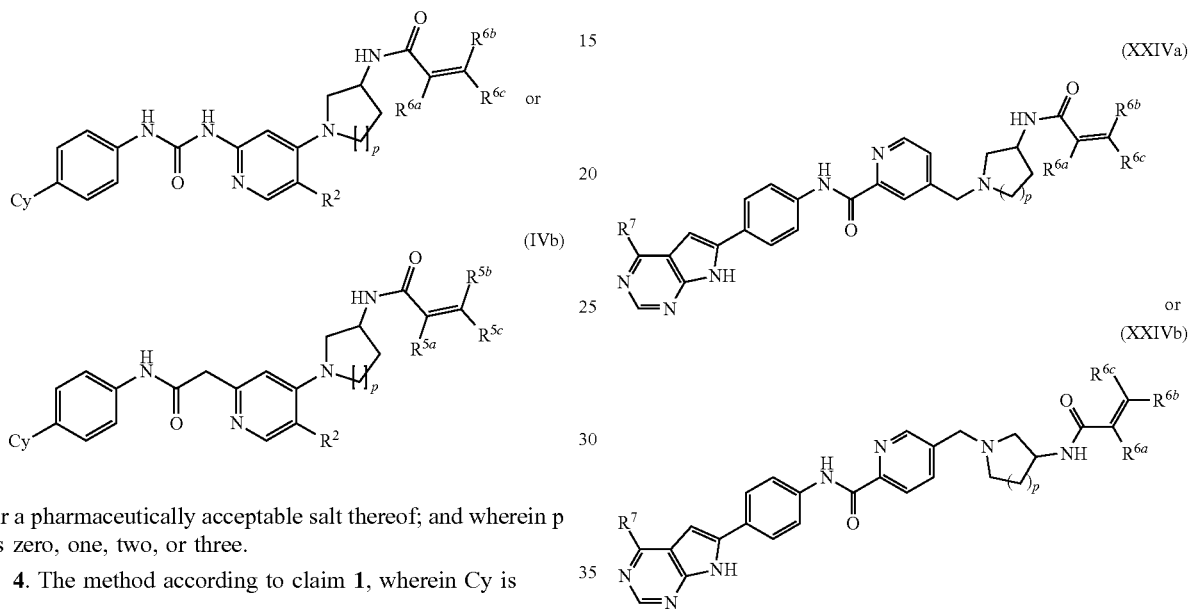

(XXIVa)

or (XXIVb)

or a pharmaceutically acceptable salt thereof; wherein p is zero, one, two, or three; and $R^7$ is

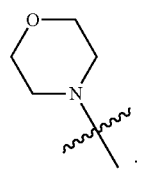 [SMILES: *N1CCOCC1]

6. The method according to claim 1, wherein the compound is according to Formula (VIIa), (VIIb), (VIIc), (VIIIa), (VIIIb), (VIIIc), (XXVIa), (XXVIb), or (XXVIc)

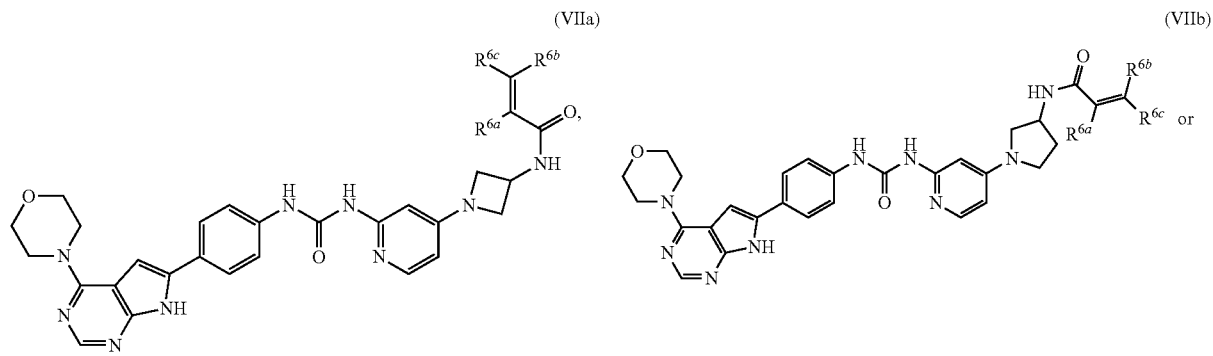

(VIIa)

(VIIb)

-continued
(VIIc)
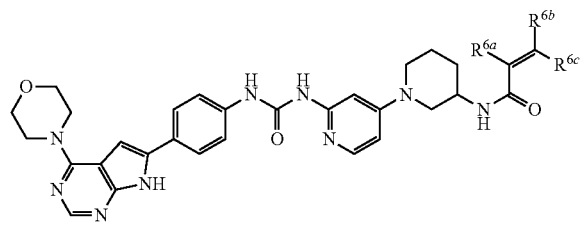
(VIIIa)
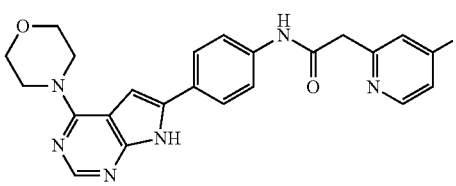
(VIIIb)
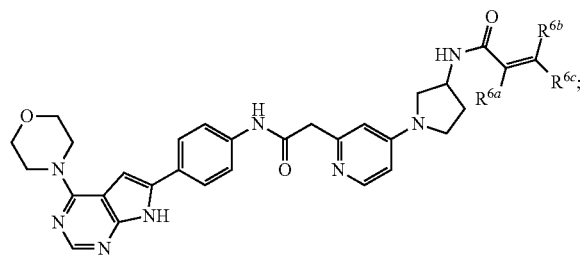
(VIIIc)
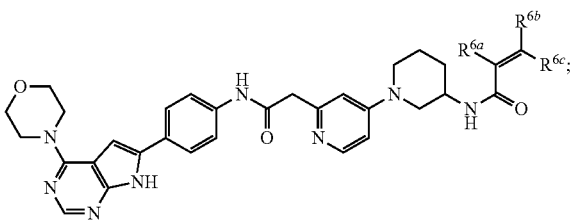
(XXVIa)
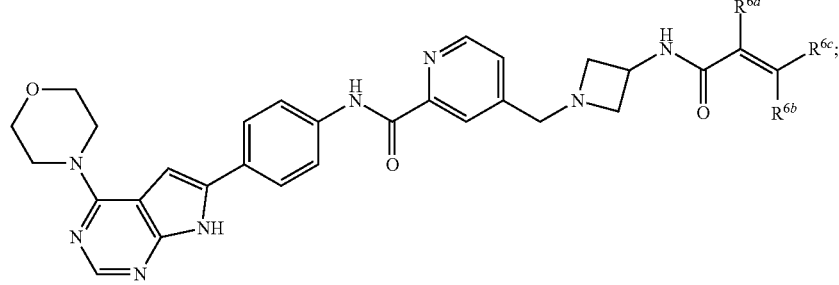
(XXVIb)
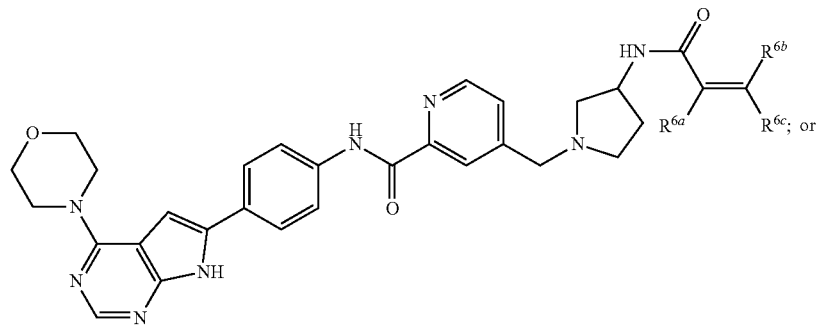
(XXVIc)
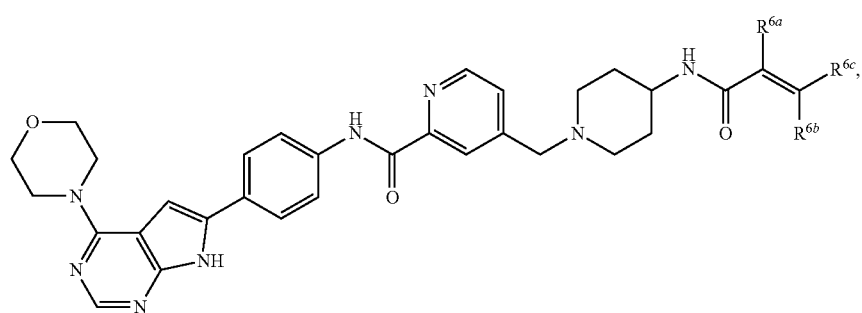
or a pharmaceutically acceptable salt thereof.

7. The method of claim 1, wherein
i) $R^{6a}$ is hydrogen;
   $R^{6b}$ is hydrogen; and
   $R^{6c}$ is hydrogen; or
ii) $R^{6a}$ is hydrogen;
   $R^{6b}$ is hydrogen; and
   $R^{6c}$ is $CH_3$ or $CH_2CH_3$; or
iii) $R^{6a}$ is hydrogen;
   $R^{6b}$ is hydrogen; and
   $R^{6c}$ is $CH_2N(CH_3)_2$; or
iv) $R^{6a}$ and $R^{6b}$, joined together, form a single bond; and
   $R^{6c}$ is $CH_3$.

8. The method of claim 1, wherein each of $R^{6a}$ and $R^{6b}$ is hydrogen; and $R^{6c}$ is substituted or unsubstituted alkyl.

9. The method according to claim 1, wherein the compound is according to Formula (IXa), (IXb), (IXc), (Xa), (Xb), (Xc), (XIa), (XIb), (XIc), (XIIa), (XIIb), (XIIc), (XIIIa), (XIIIb), (XIIIc), or (XIVa)

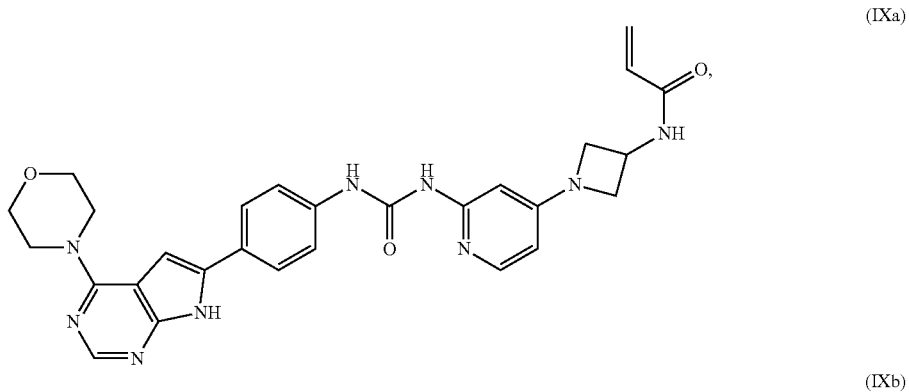

(IXa)

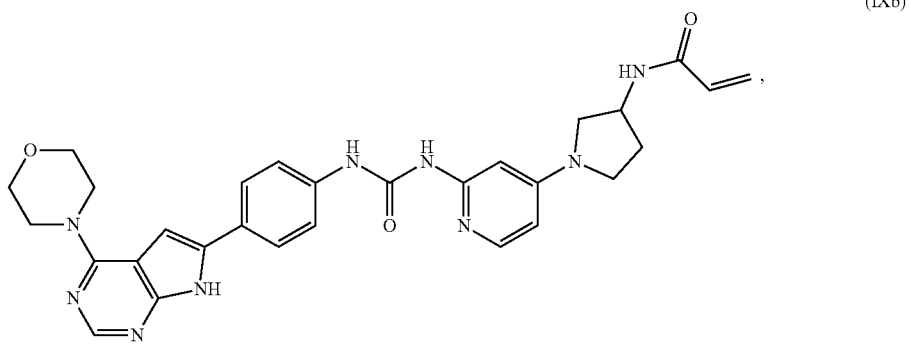

(IXb)

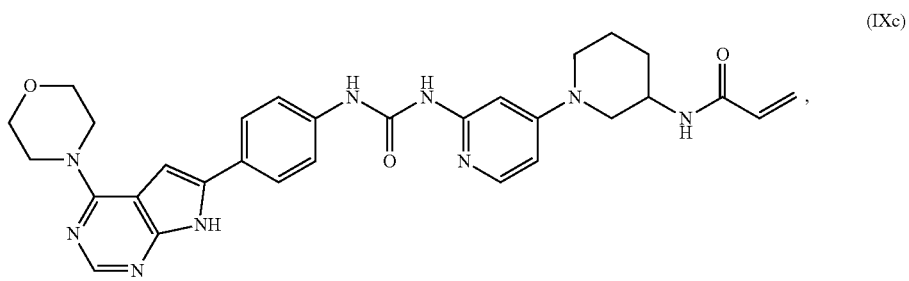

(IXc)

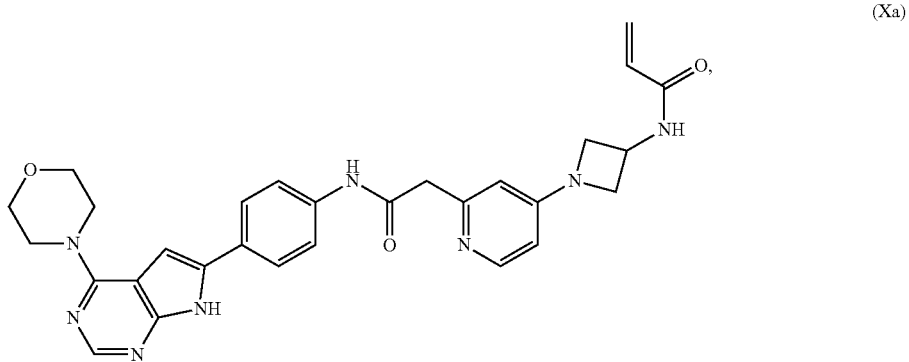

(Xa)

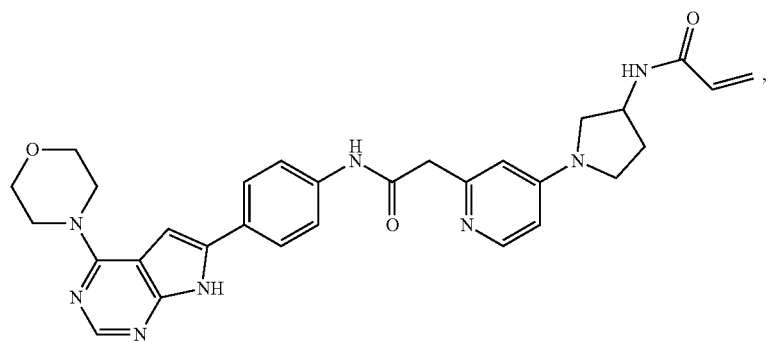
(Xb)
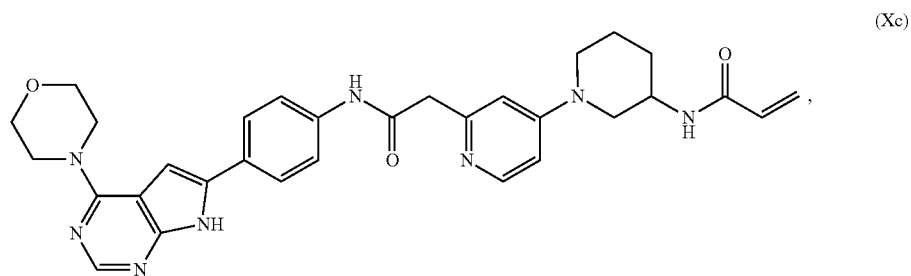
(Xc)
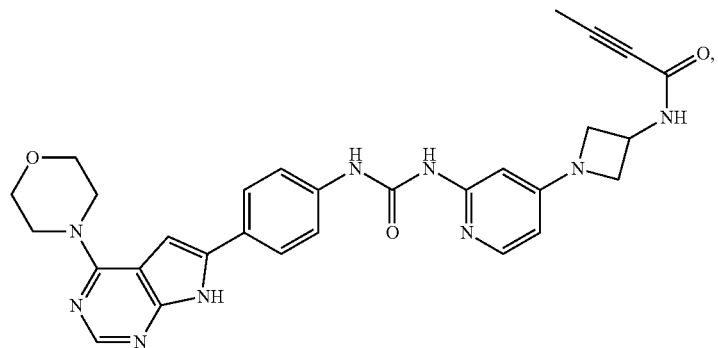
(XIa)
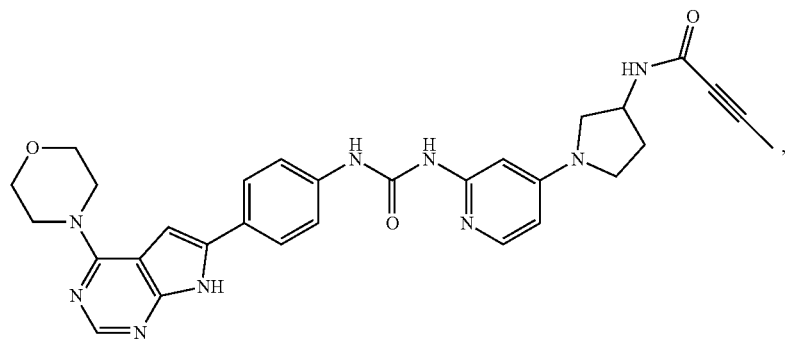
(XIb)
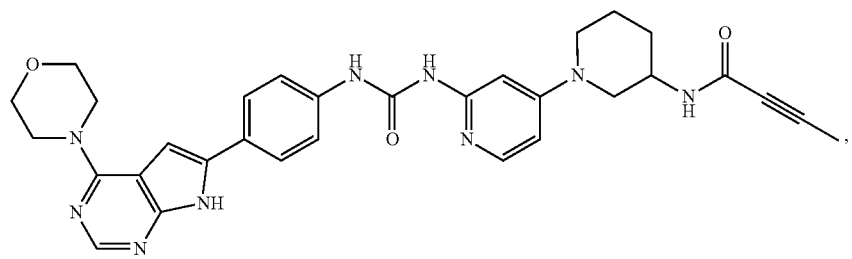
(XIc)

-continued
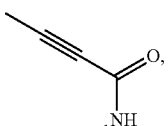
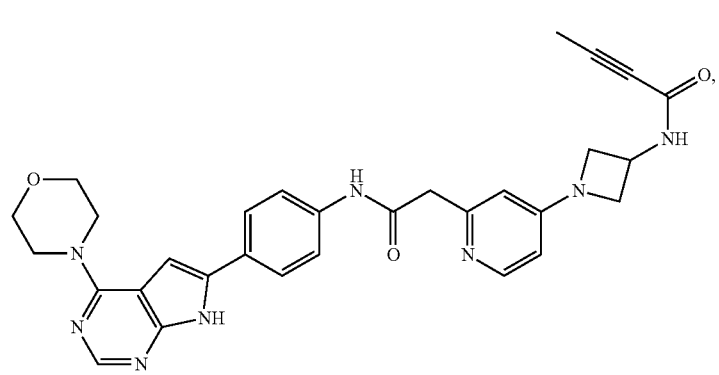
(XIIa)
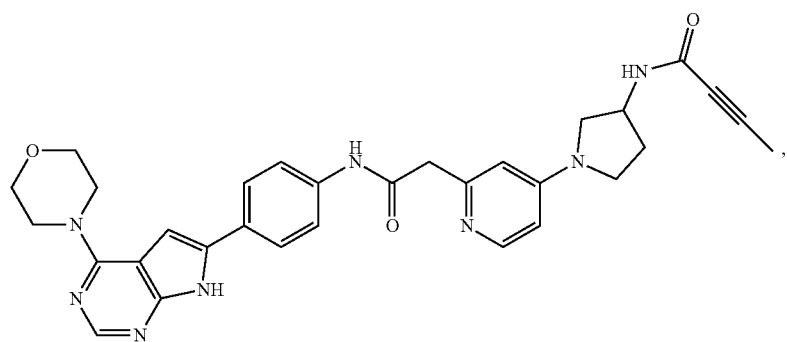
(XIIb)
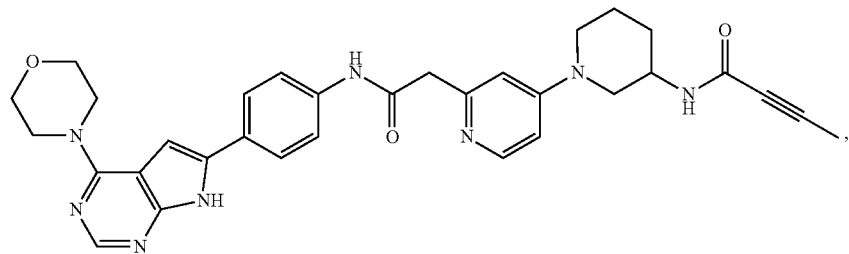
(XIIc)
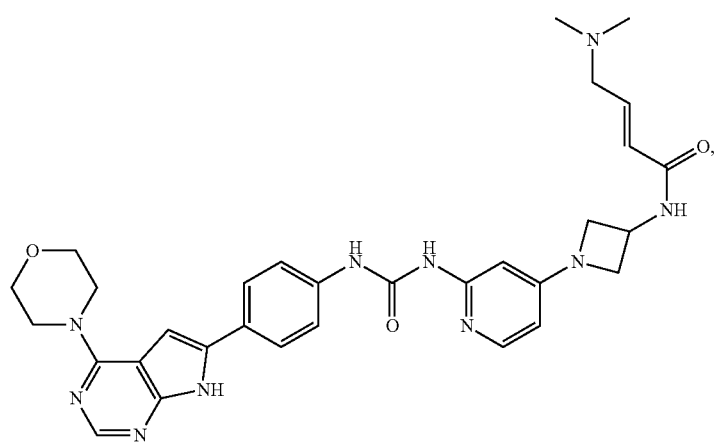
(XIIIa)

-continued
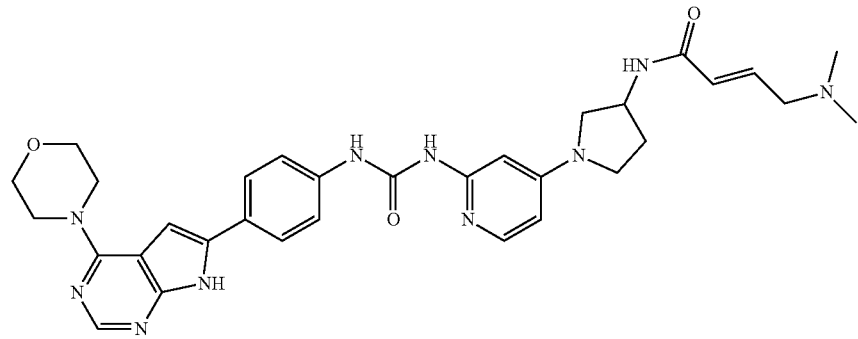
(XIIIb)
or
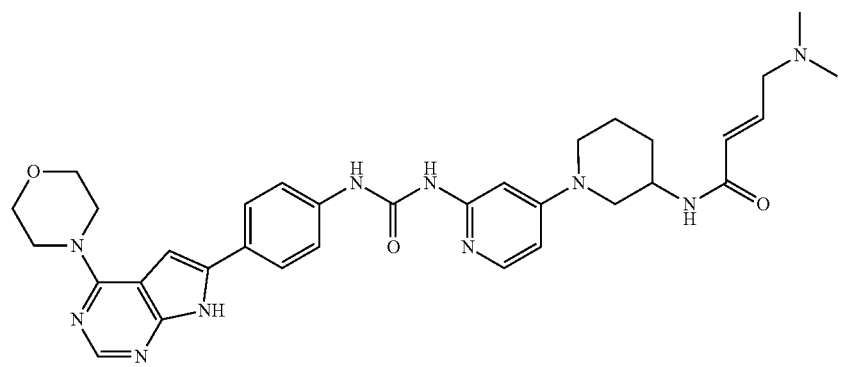
(XIIIc)
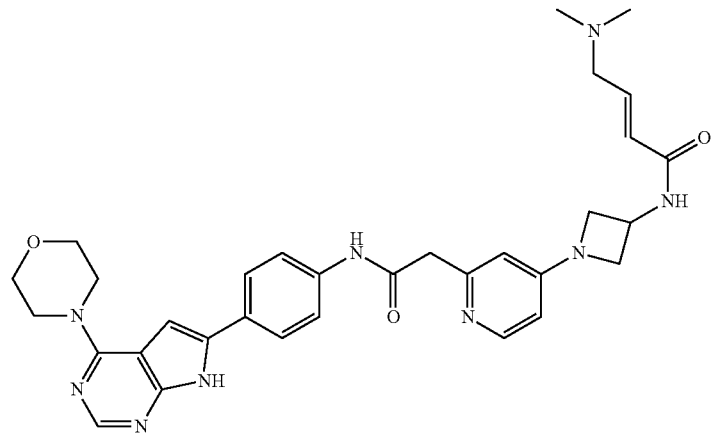
(XIVa)
or a pharmaceutically acceptable salt thereof.
10. The method according to claim 1, wherein the compound is according to Formula (XVI) or (XVII)
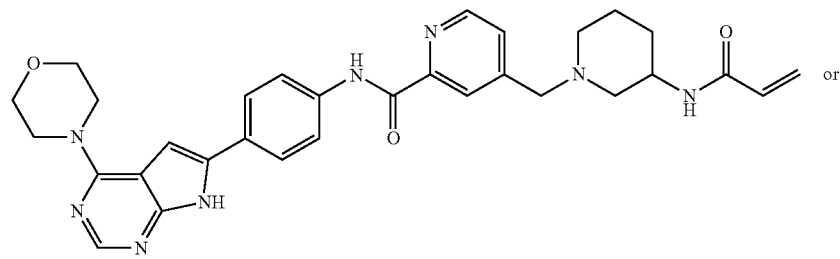
(XVI)
or -continued
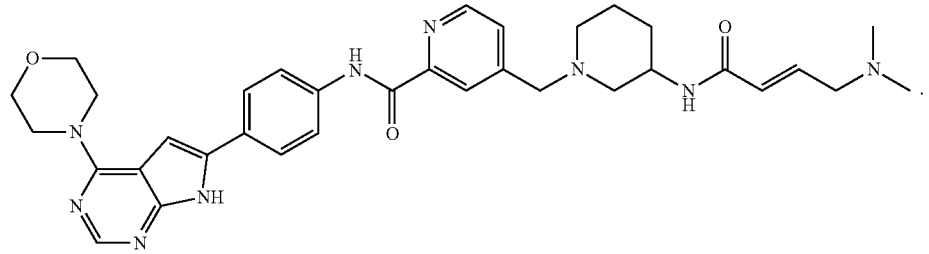
(XVII)
or a pharmaceutically acceptable salt thereof.
11. The method according to claim 1, wherein the compound is according to Formula (XXVIIa), (XXVIIb), (XXVIIc), (XXVIIIa), (XXVIIIb), (XXVIIIc), (XXIXa), (XXIXb), or (XXIXc)
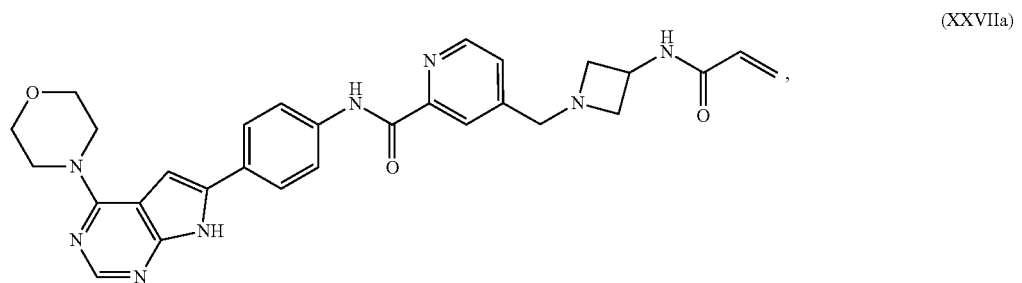
(XXVIIa)
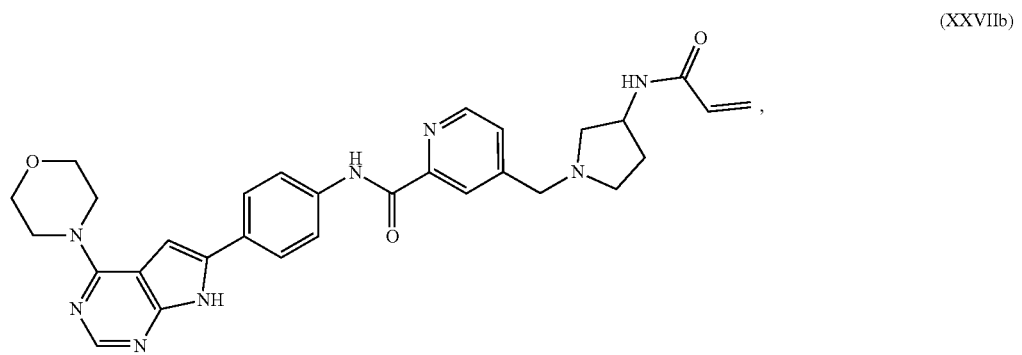
(XXVIIb)
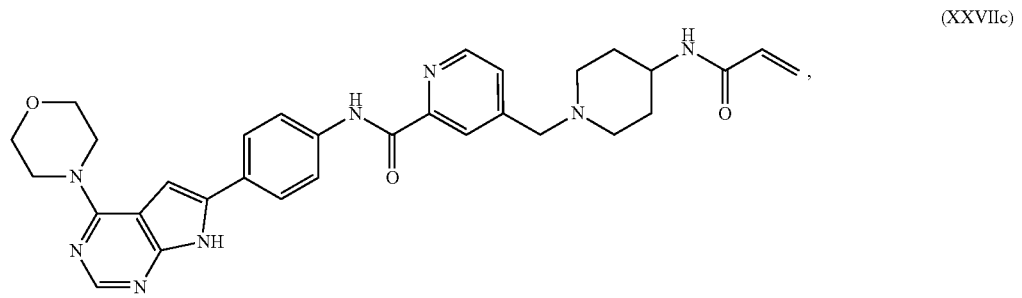
(XXVIIc)

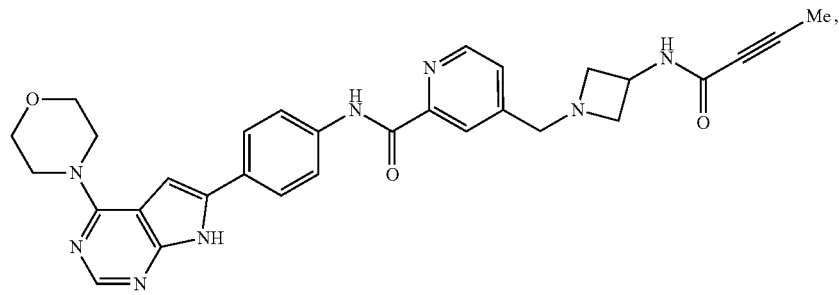
(XXVIIIa)
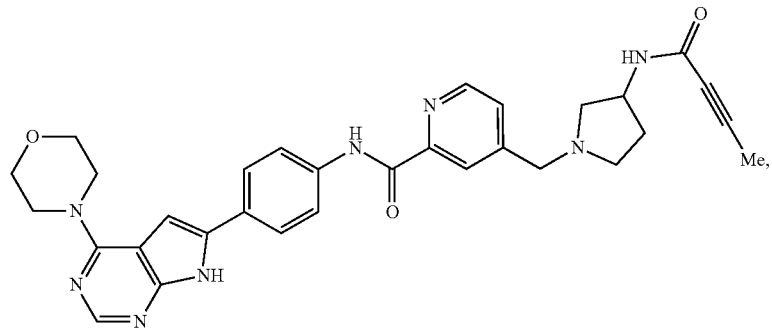
(XXVIIIb)
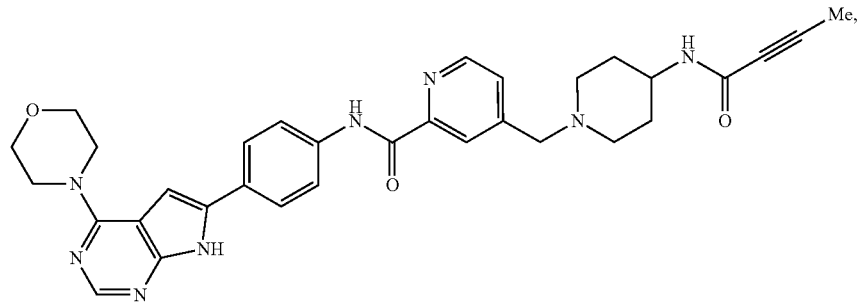
(XXVIIIc)
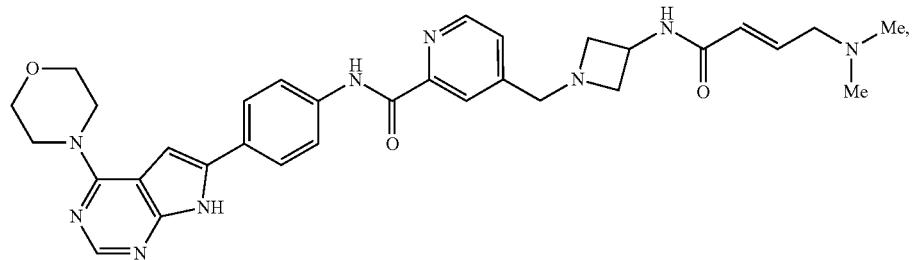
(XXIXa)

(XXIXb)
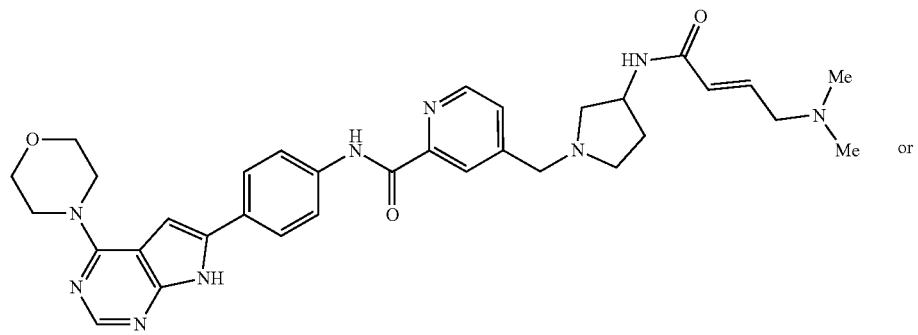
or
(XXIXc)
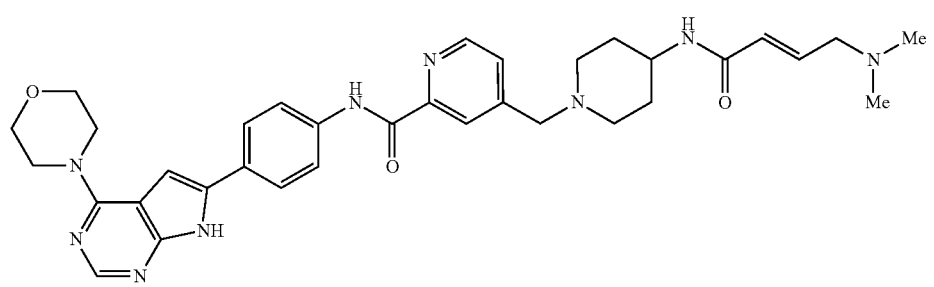
or a pharmaceutically acceptable salt thereof.
12. The method according to claim 1, wherein the compound is
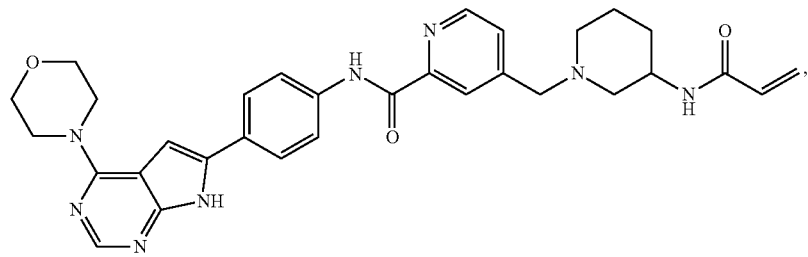 [SMILES: C=CC(=O)NC1CCCN(Cc2ccnc(C(=O)Nc3ccc(-c4cc5c(N6CCOCC6)ncnc5[nH]4)cc3)c2)C1]
or a pharmaceutically acceptable salt thereof.
13. The method according to claim 1, wherein the compound is Compound 10
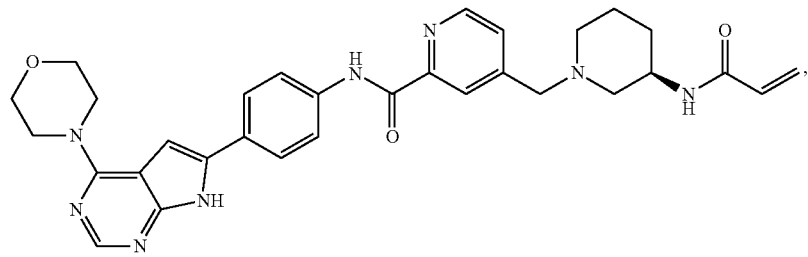 [SMILES: C=CC(=O)N[C@@H]1CCCN(Cc2ccnc(C(=O)Nc3ccc(-c4cc5c(N6CCOCC6)ncnc5[nH]4)cc3)c2)C1]
or a pharmaceutically acceptable salt thereof.
14. The method of claim 1, wherein the compound is any one of the compounds selected from

| Compound ID | Structure |
|---|---|
| 1 | 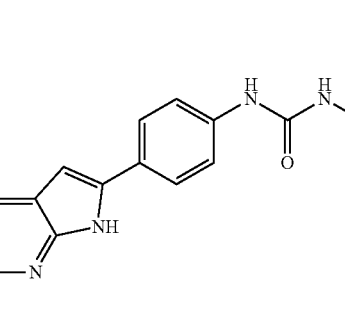 |
| 2 | 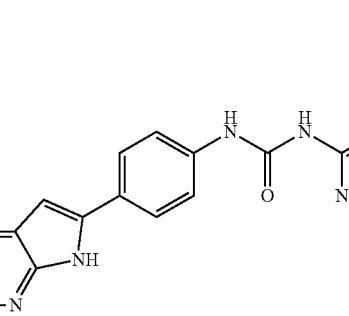 |
| 3 | 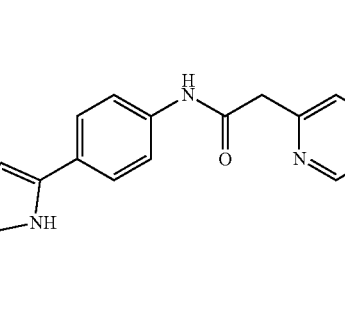 |
| 4 | 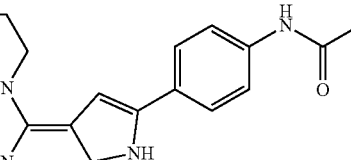 |
| 5 | 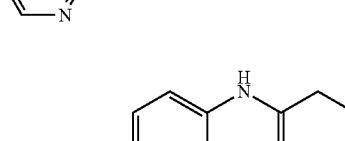 |

| Compound ID | Structure |
|---|---|
| 6 | 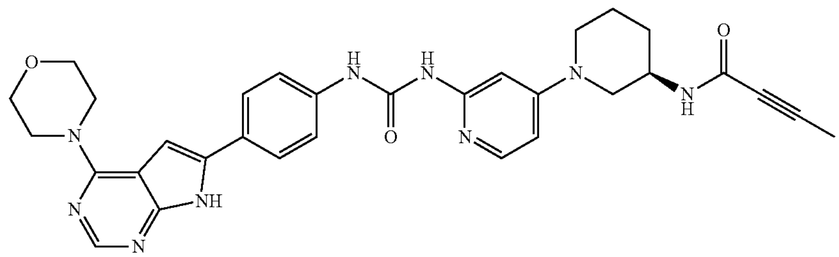 [SMILES: CC#CC(=O)N[C@@H]1CCCN(c2ccnc(NC(=O)Nc3ccc(-c4cc5c(N6CCOCC6)ncnc5[nH]4)cc3)c2)C1] |
| 7 | 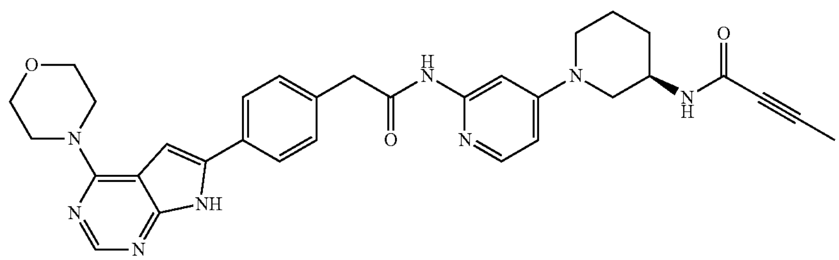 [SMILES: CC#CC(=O)N[C@@H]1CCCN(c2ccnc(NC(=O)Cc3ccc(-c4cc5c(N6CCOCC6)ncnc5[nH]4)cc3)c2)C1] |
| 8 | 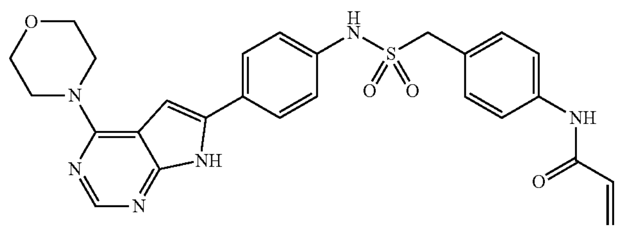 [SMILES: C=CC(=O)Nc1ccc(CS(=O)(=O)Nc2ccc(-c3cc4c(N5CCOCC5)ncnc4[nH]3)cc2)cc1] |
| 9 | 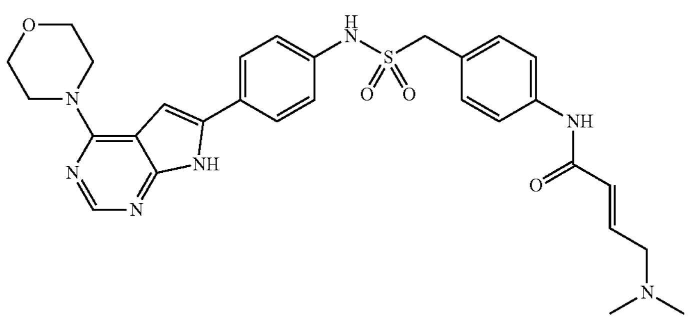 [SMILES: CN(C)C/C=C/C(=O)Nc1ccc(CS(=O)(=O)Nc2ccc(-c3cc4c(N5CCOCC5)ncnc4[nH]3)cc2)cc1] |
| 10 | 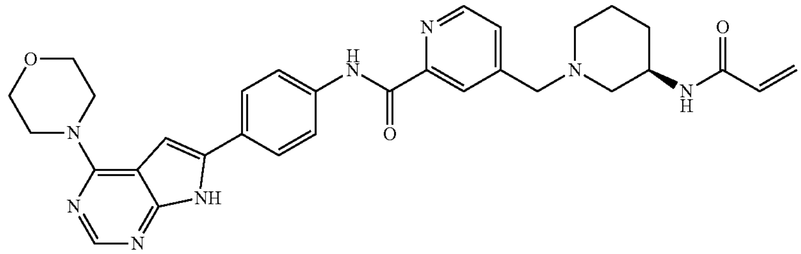 |

Compound 10

| Compound ID | Structure |
|---|---|
| 11 | 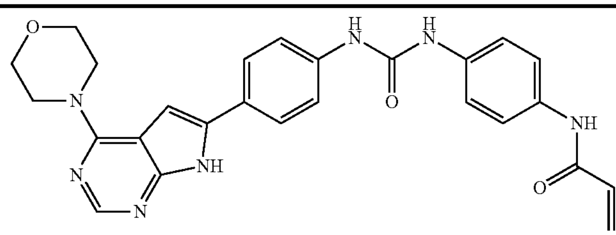 |
| 12 | 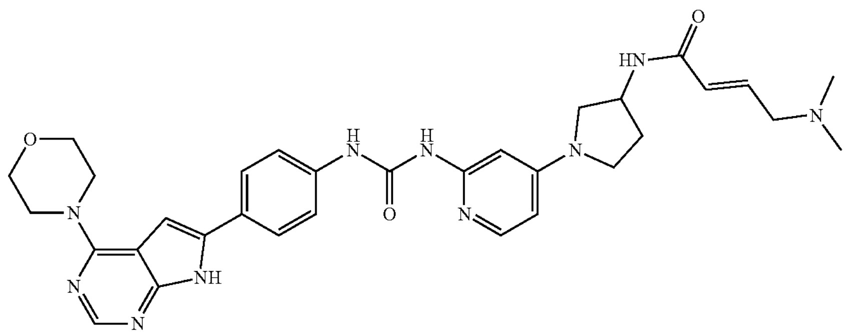 [SMILES: CN(C)C/C=C/C(=O)NC1CCN(c2ccnc(NC(=O)Nc3ccc(-c4cc5c(N6CCOCC6)ncnc5[nH]4)cc3)c2)C1] |
| 13 | 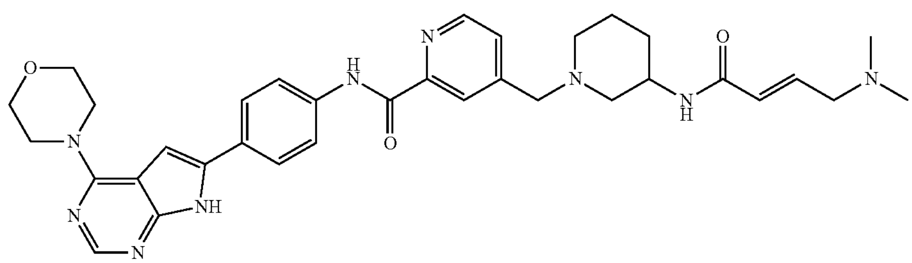 [SMILES: CN(C)C/C=C/C(=O)NC1CCCN(Cc2ccnc(C(=O)Nc3ccc(-c4cc5c(N6CCOCC6)ncnc5[nH]4)cc3)c2)C1] |
| 14 | 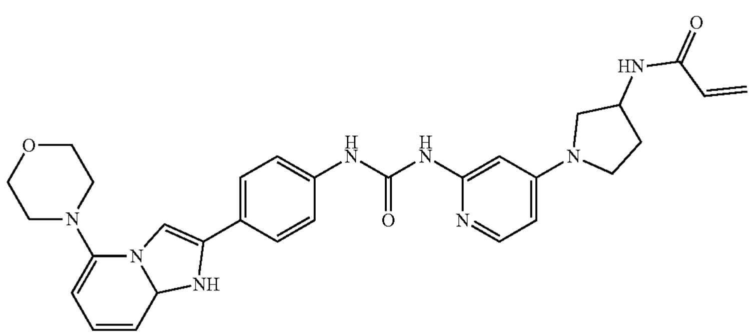 [SMILES: C=CC(=O)NC1CCN(c2ccnc(NC(=O)Nc3ccc(C4=CN5C(N6CCOCC6)=CC=CC5N4)cc3)c2)C1] |
| 15 | 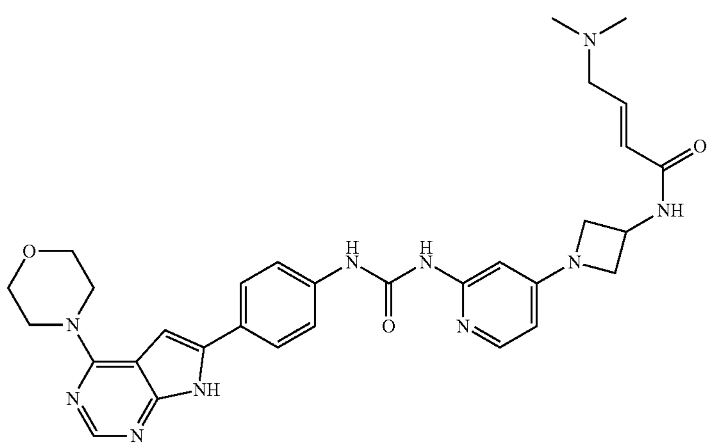 [SMILES: CN(C)C/C=C/C(=O)NC1CN(c2ccnc(NC(=O)Nc3ccc(-c4cc5c(N6CCOCC6)ncnc5[nH]4)cc3)c2)C1] |

| Compound ID | Structure |
|---|---|
| 16 | 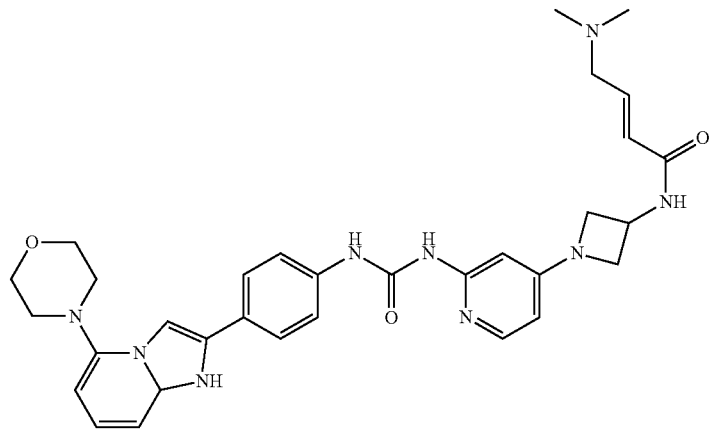 [SMILES: CN(C)C/C=C/C(=O)NC1CN(c2ccnc(NC(=O)Nc3ccc(C4=CN5C(N6CCOCC6)=CC=CC5N4)cc3)c2)C1] |
| 17 | 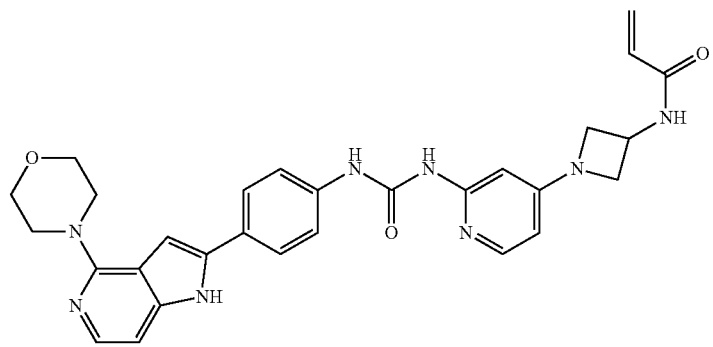 [SMILES: C=CC(=O)NC1CN(c2ccnc(NC(=O)Nc3ccc(-c4cc5c(N6CCOCC6)nccc5[nH]4)cc3)c2)C1] |
| 18 | 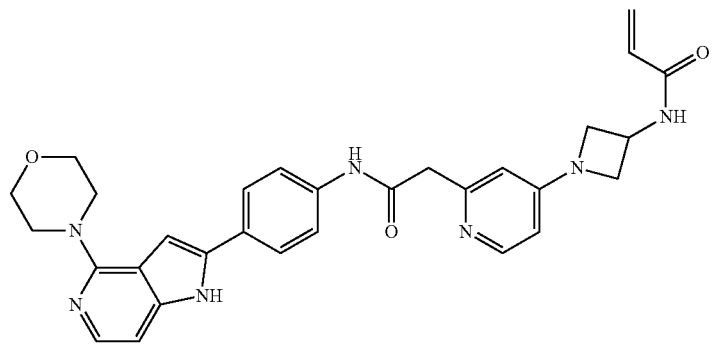 [SMILES: C=CC(=O)NC1CN(c2ccnc(CC(=O)Nc3ccc(-c4cc5c(N6CCOCC6)nccc5[nH]4)cc3)c2)C1] |
| 19 | 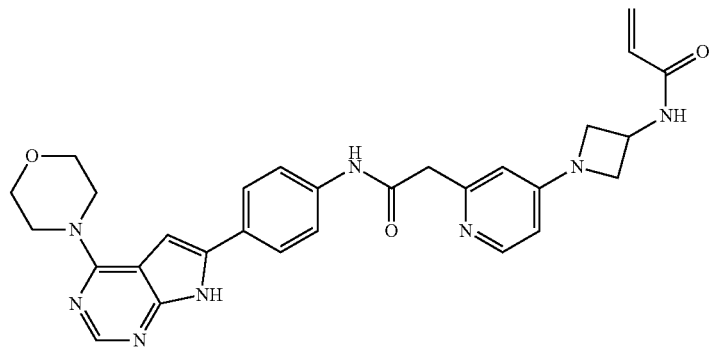 [SMILES: C=CC(=O)NC1CN(c2ccnc(CC(=O)Nc3ccc(-c4cc5c(N6CCOCC6)ncnc5[nH]4)cc3)c2)C1] |

| Compound ID | Structure |
|---|---|
| 20 | 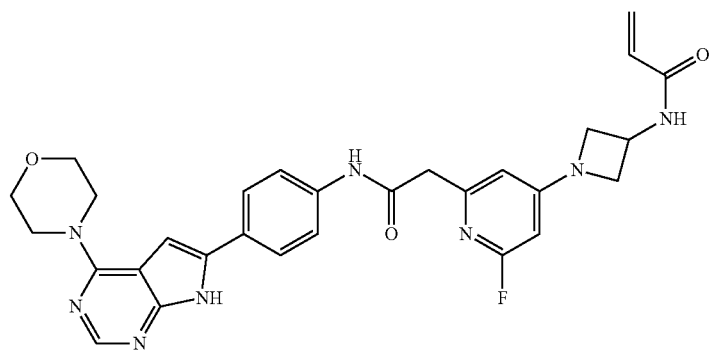 [SMILES: C=CC(=O)NC1CN(c2cc(F)nc(CC(=O)Nc3ccc(-c4cc5c(N6CCOCC6)ncnc5[nH]4)cc3)c2)C1] |
| 21 | 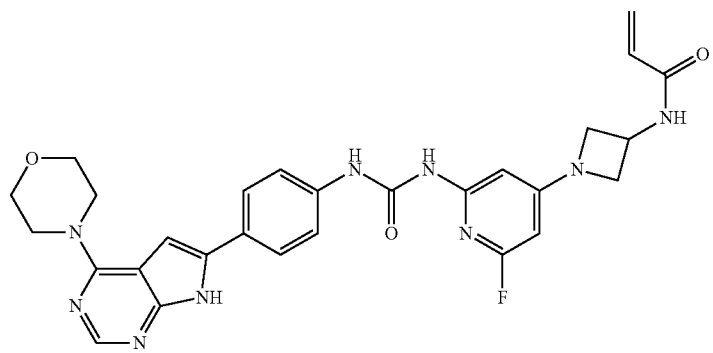 [SMILES: C=CC(=O)NC1CN(c2cc(F)nc(NC(=O)Nc3ccc(-c4cc5c(N6CCOCC6)ncnc5[nH]4)cc3)c2)C1] |
| 22 | 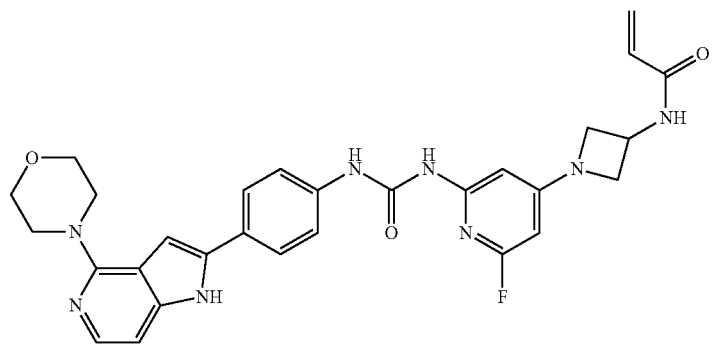 [SMILES: C=CC(=O)NC1CN(c2cc(F)nc(NC(=O)Nc3ccc(-c4cc5c(N6CCOCC6)nccc5[nH]4)cc3)c2)C1] |
| 23 | 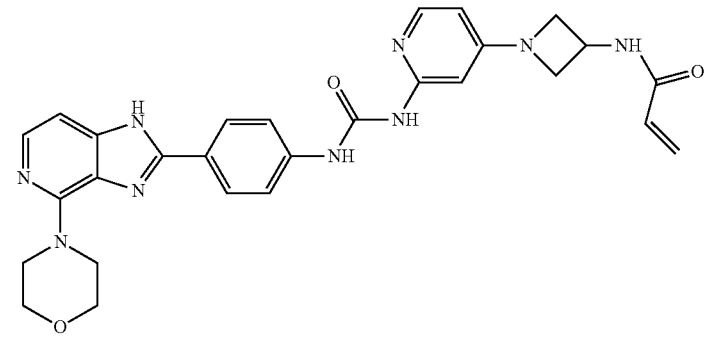 [SMILES: C=CC(=O)NC1CN(c2ccnc(NC(=O)Nc3ccc(-c4nc5c(N6CCOCC6)nccc5[nH]4)cc3)c2)C1] |

-continued

| Compound ID | Structure |
|---|---|
| 24 | 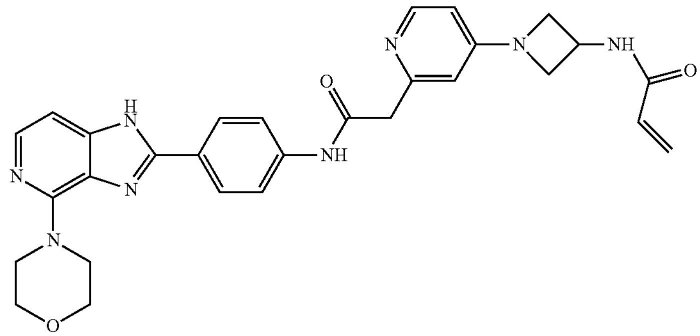 [SMILES: C=CC(=O)NC1CN(c2ccnc(CC(=O)Nc3ccc(-c4nc5c(N6CCOCC6)nccc5[nH]4)cc3)c2)C1] |
| 25 | 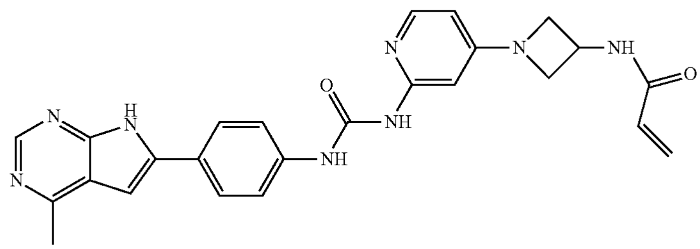 [SMILES: C=CC(=O)NC1CN(c2ccnc(NC(=O)Nc3ccc(-c4cc5c(C)ncnc5[nH]4)cc3)c2)C1] |
| 26 | | or

| Compound ID | Structure |
|---|---|
| 101 | 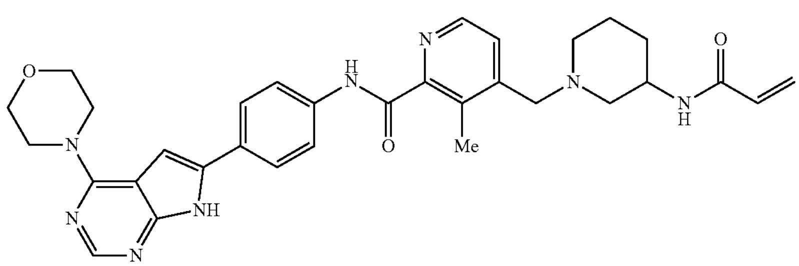 [SMILES: C=CC(=O)NC1CCCN(Cc2ccnc(C(=O)Nc3ccc(-c4cc5c(N6CCOCC6)ncnc5[nH]4)cc3)c2C)C1] |

| Compound ID | Structure |
|---|---|
| 102 | 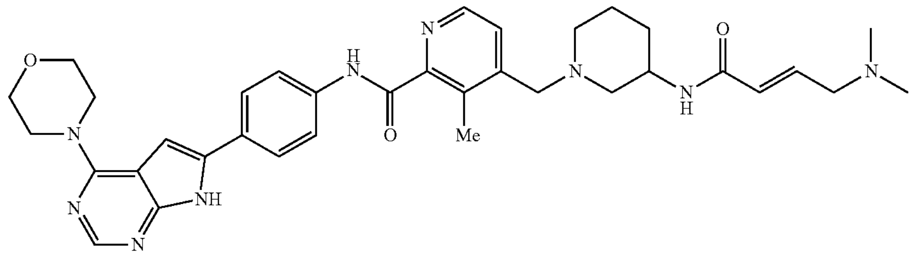 [SMILES: Cc1c(CN2CCCC(NC(=O)/C=C/CN(C)C)C2)ccnc1C(=O)Nc1ccc(-c2cc3c(N4CCOCC4)ncnc3[nH]2)cc1] |
| 103 | 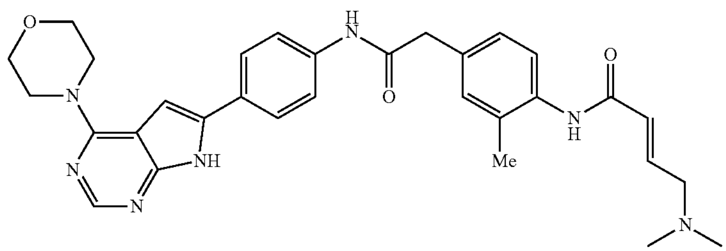 [SMILES: Cc1cc(CC(=O)Nc2ccc(-c3cc4c(N5CCOCC5)ncnc4[nH]3)cc2)ccc1NC(=O)/C=C/CN(C)C] |
| 104 | 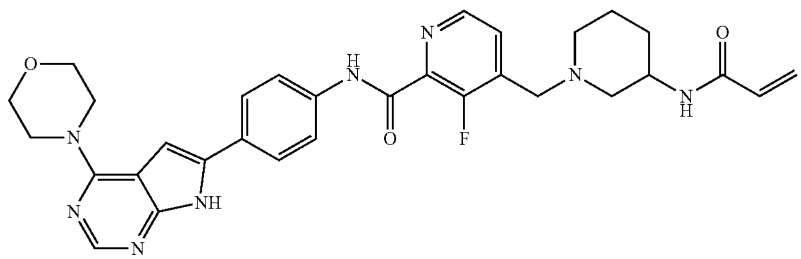 [SMILES: C=CC(=O)NC1CCCN(Cc2ccnc(C(=O)Nc3ccc(-c4cc5c(N6CCOCC6)ncnc5[nH]4)cc3)c2F)C1] |
| 105 | 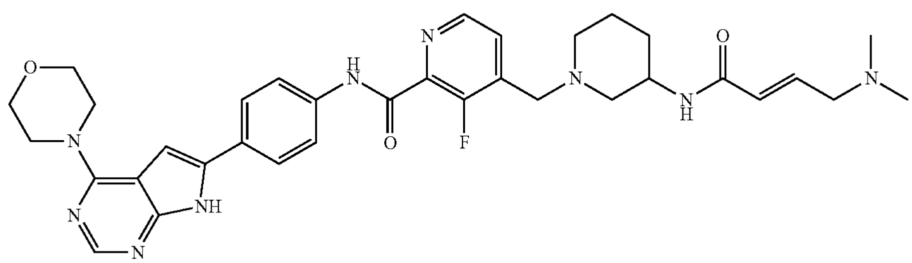 [SMILES: CN(C)C/C=C/C(=O)NC1CCCN(Cc2ccnc(C(=O)Nc3ccc(-c4cc5c(N6CCOCC6)ncnc5[nH]4)cc3)c2F)C1] |
| 106 | 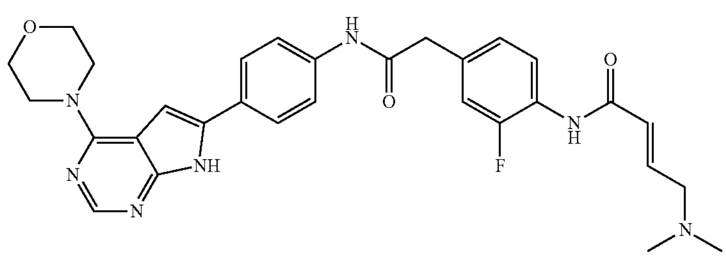 [SMILES: CN(C)C/C=C/C(=O)Nc1ccc(CC(=O)Nc2ccc(-c3cc4c(N5CCOCC5)ncnc4[nH]3)cc2)cc1F] |
| 107 | 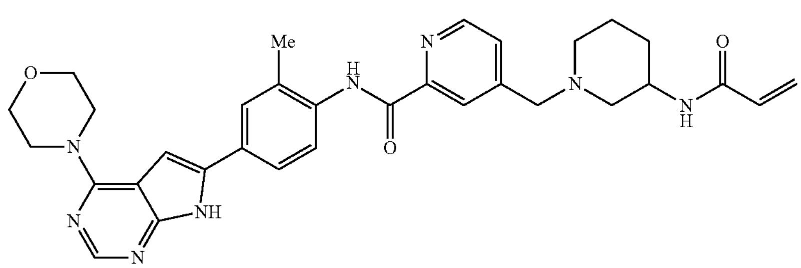 [SMILES: C=CC(=O)NC1CCCN(Cc2ccnc(C(=O)Nc3ccc(-c4cc5c(N6CCOCC6)ncnc5[nH]4)cc3C)c2)C1] |

| Compound ID | Structure |
|---|---|
| 108 | 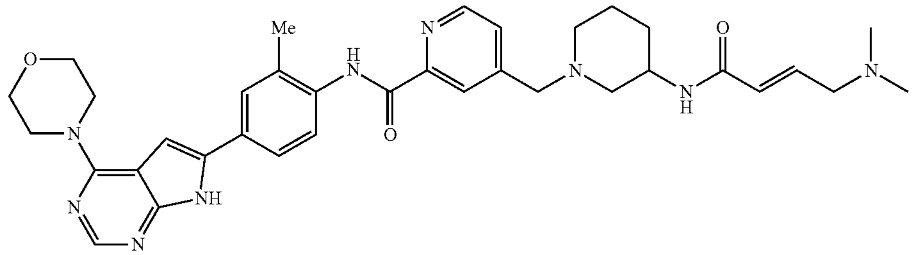 [SMILES: Cc1cc(-c2cc3c(N4CCOCC4)ncnc3[nH]2)ccc1NC(=O)c1cc(CN2CCCC(NC(=O)/C=C/CN(C)C)C2)ccn1] |
| 109 | 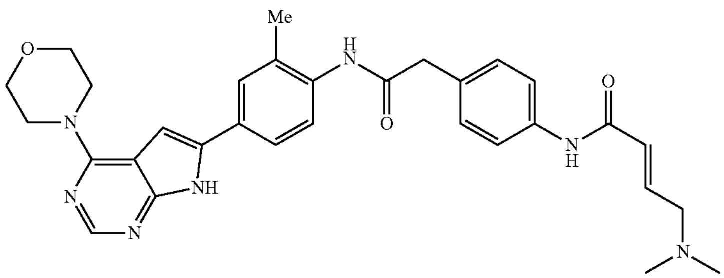 [SMILES: Cc1cc(-c2cc3c(N4CCOCC4)ncnc3[nH]2)ccc1NC(=O)Cc1ccc(NC(=O)/C=C/CN(C)C)cc1] |
| 110 | 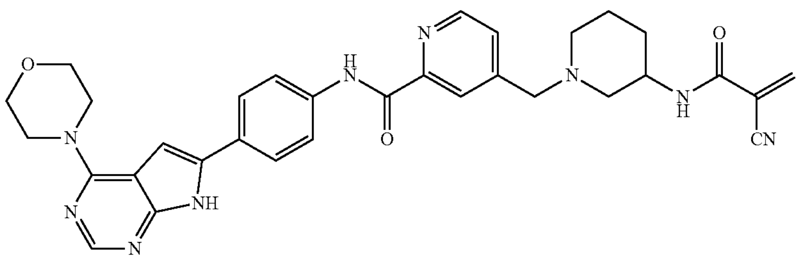 [SMILES: C=C(C#N)C(=O)NC1CCCN(Cc2ccnc(C(=O)Nc3ccc(-c4cc5c(N6CCOCC6)ncnc5[nH]4)cc3)c2)C1] |
| 111 | 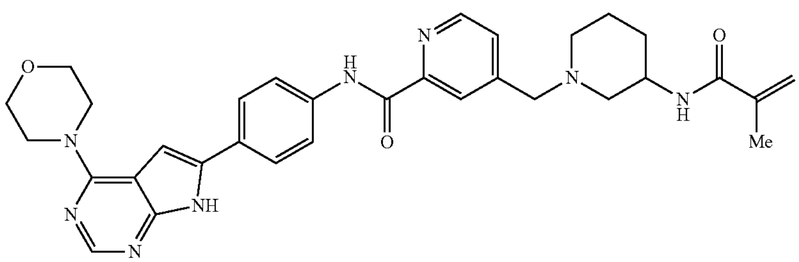 [SMILES: C=C(C)C(=O)NC1CCCN(Cc2ccnc(C(=O)Nc3ccc(-c4cc5c(N6CCOCC6)ncnc5[nH]4)cc3)c2)C1] |
| 112 | 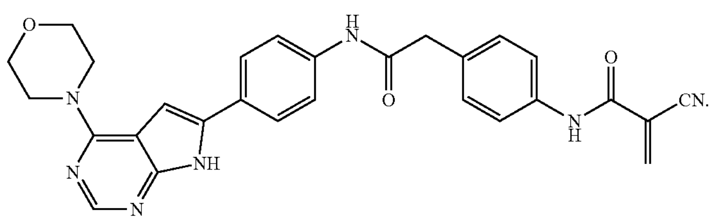 [SMILES: C=C(C#N)C(=O)Nc1ccc(CC(=O)Nc2ccc(-c3cc4c(N5CCOCC5)ncnc4[nH]3)cc2)cc1] |

15. The method of claim 1, wherein the HbA1c is lowered by at least 0.5% within one month of dosing.

16. The method of claim 1, wherein the HbA1c is lowered by 1%-3.5% between day 21 and day 29 of dosing.

17. The method of claim 1, wherein reducing HbA1c occurs within four weeks of dosing.

* * * * *